(12) United States Patent
Ellington et al.

(10) Patent No.: US 11,746,374 B2
(45) Date of Patent: Sep. 5, 2023

(54) METHODS AND PLATFORM FOR SCREENING AND SELECTING METABOLITES AND THEIR RECEPTORS

(71) Applicants: BOARD OF REGENTS, THE UNIVERSITY OF TEXAS SYSTEM, Austin, TX (US); THE TEXAS A&M UNIVERSITY SYSTEM, College Station, TX (US)

(72) Inventors: Andrew Ellington, Austin, TX (US); Jimmy Gollihar, Hewitt, TX (US); Katy Kao, College Station, TX (US); Elizabeth Gardner, Austin, TX (US)

(73) Assignees: BOARD OF REGENTS, THE UNIVERSITY OF TEXAS SYSTEM, Austin, TX (US); THE TEXAS A&M UNIVERSITY, College Station, TX (US)

( * ) Notice: Subject to any disclaimer, the term of this patent is extended or adjusted under 35 U.S.C. 154(b) by 588 days.

(21) Appl. No.: 16/622,445

(22) PCT Filed: Jun. 15, 2018

(86) PCT No.: PCT/US2018/037818
§ 371 (c)(1),
(2) Date: Dec. 13, 2019

(87) PCT Pub. No.: WO2018/232282
PCT Pub. Date: Dec. 20, 2018

(65) Prior Publication Data
US 2020/0208201 A1    Jul. 2, 2020

Related U.S. Application Data

(60) Provisional application No. 62/520,189, filed on Jun. 15, 2017.

(51) Int. Cl.
C12Q 1/68    (2018.01)
C12Q 1/6811  (2018.01)
C12Q 1/48    (2006.01)

(52) U.S. Cl.
CPC ............ C12Q 1/6811 (2013.01); C12Q 1/48 (2013.01)

(58) Field of Classification Search
None
See application file for complete search history.

(56) References Cited

U.S. PATENT DOCUMENTS 7,429,467 B2 *  9/2008  Holliger .............. C12Q 1/6844
                                                 435/68.1
7,514,210 B2 *  4/2009  Holliger ............ C12N 15/1058
                                                 435/6.16

(Continued)

FOREIGN PATENT DOCUMENTS

WO    2014/170343    10/2014

OTHER PUBLICATIONS

Goswami et al. (J Pain, 2014, 15(12):1338-1359) (Year: 2014).*

(Continued)

*Primary Examiner* — Stephanie K Mummert
(74) *Attorney, Agent, or Firm* — Meunier Carlin & Curfman LLC

(57) ABSTRACT

Disclosed herein are methods and platforms using Receptor Compartmentalized Partnered Replication (CPR), in which the partner gene is a receptor, signal transduction pathway, or metabolic pathway that leads to the production of an effector molecule for the receptor or signal transduction pathway. The signal transduction pathway or receptor is coupled to the production of a thermostable polymerase. Emulsification of libraries of organisms with primers that can amplify the partner gene led to the selective amplifica- (Continued)

tion of those partner genes that were best able to produce the thermostable polymerase during thermal cycling of the emulsion.

18 Claims, 66 Drawing Sheets

Specification includes a Sequence Listing.

(56) References Cited

U.S. PATENT DOCUMENTS

| | | | | |
|---|---|---|---|---|
| 7,622,280 | B2* | 11/2009 | Holliger | C12N 15/1075 435/6.16 |
| 2003/0166099 | A1* | 9/2003 | Sabbadini | G01N 33/60 506/10 |
| 2007/0196837 | A1 | 8/2007 | Pokholok et al. | |

OTHER PUBLICATIONS

Park et al. (PNAS, 2014, 111(16):5896-5901) (Year: 2014).*
Packer et al. (Nature Rev Genet, 2015, 16:370-394) (Year: 2015).*
Jimmy Dale Gollihar Jr (2017, University of Texas Austin, p. 1-376) (Year: 2017).*
International Search Report and Written Opinion dated Oct. 17, 2018, from International Application No. PCT/US2018/037818, 11 pages.
Ellefson, et al. "Engineering the central dogma using emulsion based directed evolution", Dissertation [online], May 2016, 180 pages.
Gollihar, et al. "Methods in protein engineering and screening: From rational design to directed evolution and beyond", Dissertation [online], Aug. 2017, 376 pages.
Abil, Z. et al. "Compartmentalized partnered replication for the directed evolution of genetic parts and circuits", Nat Protoc. Dec. 2017 ; 12(12): 2493-2512.
Coward P, Wada HG, Falk MS, Chan SD, Meng F, Akil H, Conklin BR. Controlling signaling with a specifically designed Gi-coupled receptor. Proc Natl Acad Sci U S A. 1998;95(1):352-7. PubMed PMID: 9419379; PMCID: PMC18222.
Alexander GM, Rogan SC, Abbas AI, Armbruster BN, Pei Y, Allen JA, Nonneman RJ, Hartmann J, Moy SS, Nicolelis MA, McNamara JO, Roth BL. Remote control of neuronal activity in transgenic mice expressing evolved G protein-coupled receptors. Neuron. 2009;63(1):27-39. doi: 10.1016/j.neuron.2009.06.014. PubMed PMID: 19607790; PMCID: PMC2751885.
Armbruster BN, Li X, Pausch MH, Herlitze S, Roth BL. Evolving the lock to fit the key to create a family of G protein-coupled receptors potently activated by an inert ligand. Proc Natl Acad Sci U S A. 2007;104(12):5163-8. doi: 10.1073/pnas.0700293104. PubMed PMID: 17360345; PMCID: PMC1829280.
Guettier JM, Gautam D, Scarselli M, Ruiz de Azua I, Li JH, Rosemond E, Ma X, Gonzalez FJ, Armbruster BN, Lu H, Roth BL, Wess J. A chemical-genetic approach to study G protein regulation of beta cell function in vivo. Proc Natl Acad Sci U S A. 2009;106(45):19197-202. doi: 10.1073/pnas.0906593106. PubMed PMID: 19858481; PMCID: PMC2767362.
Nakajima K, Wess J. Design and functional characterization of a novel, arrestin-biased designer G protein-coupled receptor. Mol Pharmacol. 2012;82(4):575-82. doi: 10.1124/mol.112.080358. PubMed PMID: 22821234; PMCID: PMC3463219.
Vardy E, Robinson JE, Li C, Olsen RH, DiBerto JF, Giguere PM, Sassano FM, Huang XP, Zhu H, Urban DJ, White KL, Rittiner JE, Crowley NA, Pleil KE, Mazzone CM, Mosier PD, Song J, Kash TL, Malanga CJ, Krashes MJ, Roth BL. A New DREADD Facilitates the Multiplexed Chemogenetic Interrogation of Behavior. Neuron. 2015;86(4):936-46. doi: 10.1016/j.neuron.2015.03.065. PubMed PMID: 25937170; PMCID: PMC4441592.
Ellefson JW, Meyer AJ, Hughes RA, Cannon JR, Brodbelt JS, Ellington AD. Directed evolution of genetic parts and circuits by compartmentalized partnered replication. Nature biotechnology. 2014;32(1):97-101. doi: 10.1038/nbt.2714. PubMed PMID: 24185096.
Meyer AJ, Ellefson JW, Ellington AD. Directed Evolution of a Panel of Orthogonal T7 RNA Polymerase Variants for in Vivo or in Vitro Synthetic Circuitry. ACS synthetic biology. 2015;4(10):1070-6. doi: 10.1021/sb500299c. PubMed PMID: 25279711.
Iwamura H, Suzuki H, Ueda Y, Kaya T, Inaba T. In vitro and in vivo pharmacological characterization of JTE-907, a novel selective ligand for cannabinoid CB2 receptor. J Pharmacol Exp Ther. 2001;296(2):420-5. PubMed PMID: 11160626.
Ibrahim MM, Porreca F, Lai J, Albrecht PJ, Rice FL, Khodorova A, Davar G, Makriyannis A, Vanderah TW, Mata HP, Malan TP, Jr. CB2 cannabinoid receptor activation produces antinociception by stimulating peripheral release of endogenous opioids. Proc Natl Acad Sci U S A. 2005;102(8):3093-8. doi: 10.1073/pnas.0409888102. PubMed PMID: 15705714; PMCID: PMC549497.
Dong S, Rogan SC, Roth BL. Directed molecular evolution of DREADDs: a generic approach to creating next-generation RASSLs. Nat Protoc. 2010;5(3):561-73. doi: 10.1038/nprot.2009.239. PubMed PMID: 20203671.
Hagen DC, McCaffrey G, Sprague GF, Jr. Pheromone response elements are necessary and sufficient for basal and pheromone-induced transcription of the FUS1 gene of *Saccharomyces* cerevisiae. Mol Cell Biol. 1991;11(6):2952-61. PubMed PMID: 1903837; PMCID: PMC360123.
Brown AJ, Dyos SL, Whiteway MS, White JH, Watson MA, Marzioch M, Clare JJ, Cousens DJ, Paddon C, Plumpton C, Romanos MA, Dowell SJ. Functional coupling of mammalian receptors to the yeast mating pathway using novel yeast/mammalian G protein alpha-subunit chimeras. Yeast. 2000;16(1):11-22. doi: 10.1002/(SICI)1097-0061(Jan. 15, 2000)16:1<11::AID-YEA502>3.0.CO;2-K. PubMed PMID: 10620771.
Lee ME, DeLoache WC, Cervantes B, Dueber JE. A Highly Characterized Yeast Toolkit for Modular, Multipart Assembly. ACS synthetic biology. 2015;4(9):975-86. doi: 10.1021/sb500366v. PubMed PMID: 25871405.
Tanaka S, Miyazawa-Onami M, Iida T, Araki H. iAID: an improved auxin-inducible degron system for the construction of a 'tight' conditional mutant in the budding yeast *Saccharomyces* cerevisiae. Yeast. 2015;32(8):567-81. doi: 10.1002/yea.3080. PubMed PMID: 26081484.
Gertsch J, Leonti M, Raduner S, Racz I, Chen JZ, Xie XQ, Altmann KH, Karsak M, Zimmer A. Beta-caryophyllene is a dietary cannabinoid. Proc Natl Acad Sci U S A. 2008;105(26):9099-104. doi: 10.1073/pnas.0803601105. PubMed PMID: 18574142; PMCID: PMC2449371.
Pertwee RG. The diverse CB1 and CB2 receptor pharmacology of three plant cannabinoids: delta9-tetrahydrocannabinol, cannabidiol and delta9-tetrahydrocannabivarin. Br J Pharmacol. 2008;153(2):199-215. doi: 10.1038/sj.bjp.0707442. PubMed PMID: 17828291; PMCID: PMC2219532.

\* cited by examiner

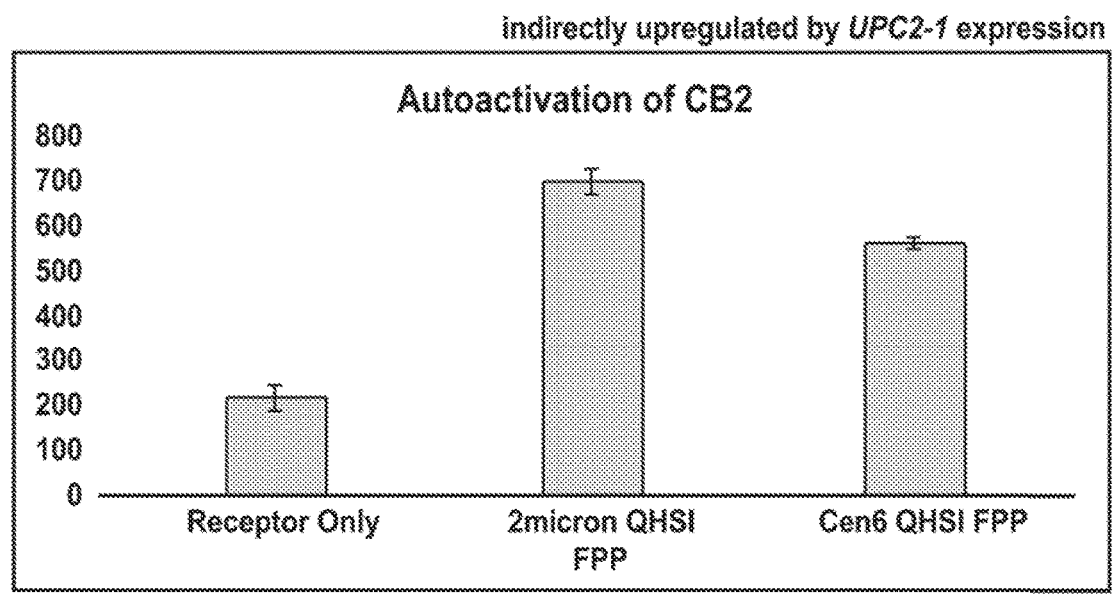
Fig. 3B
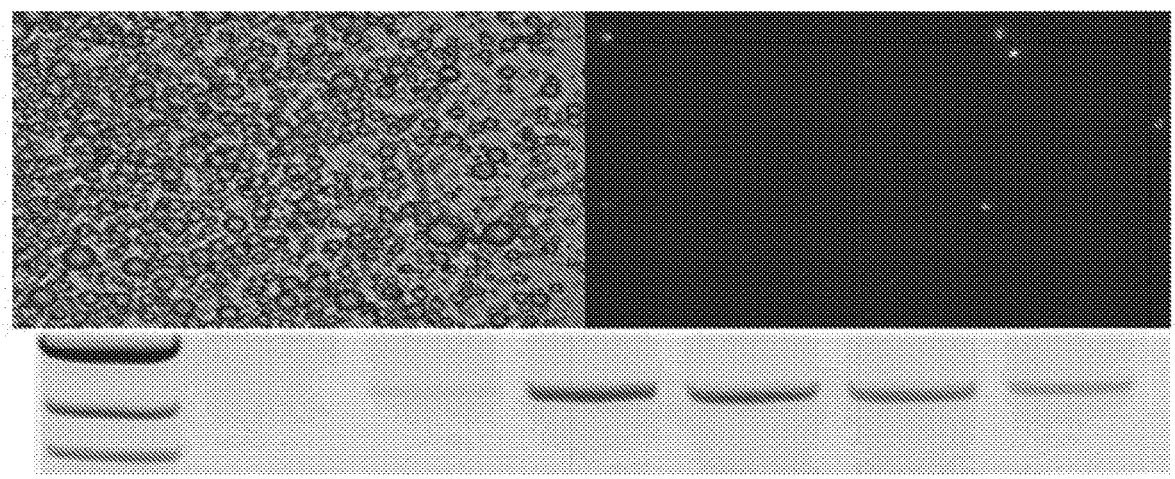
Fig. 4A-C

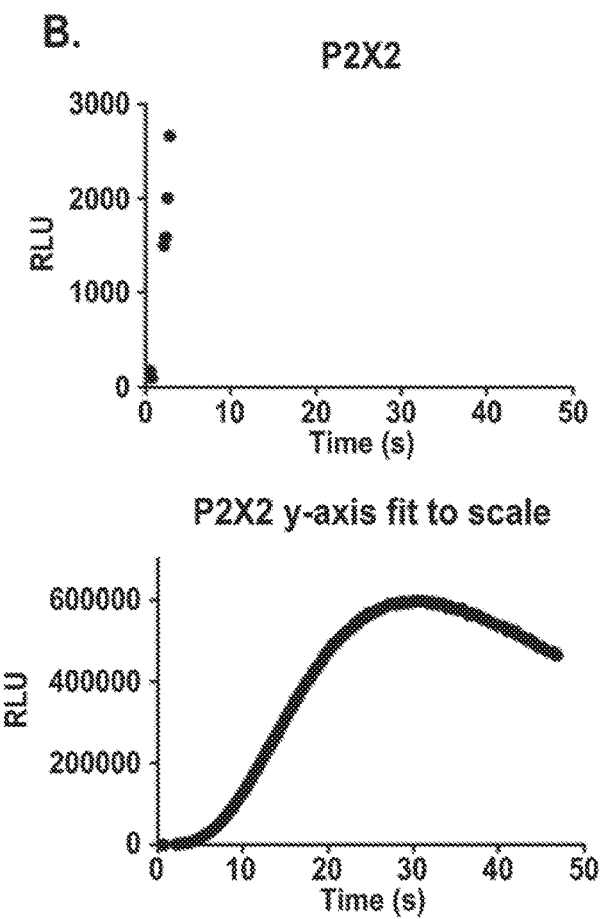
Fig. 8B
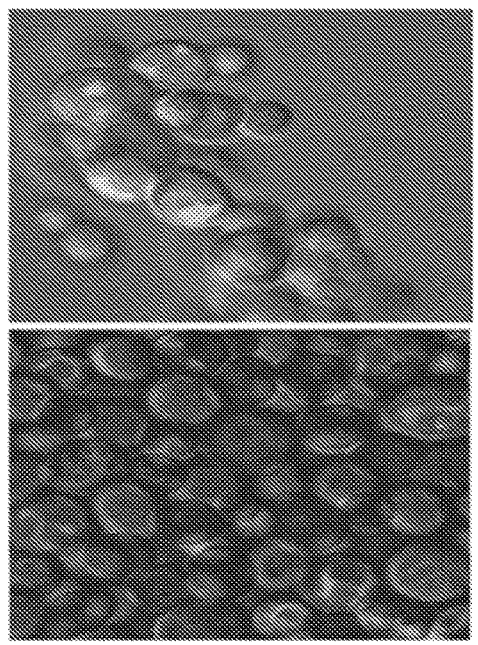
Fig. 9A-B

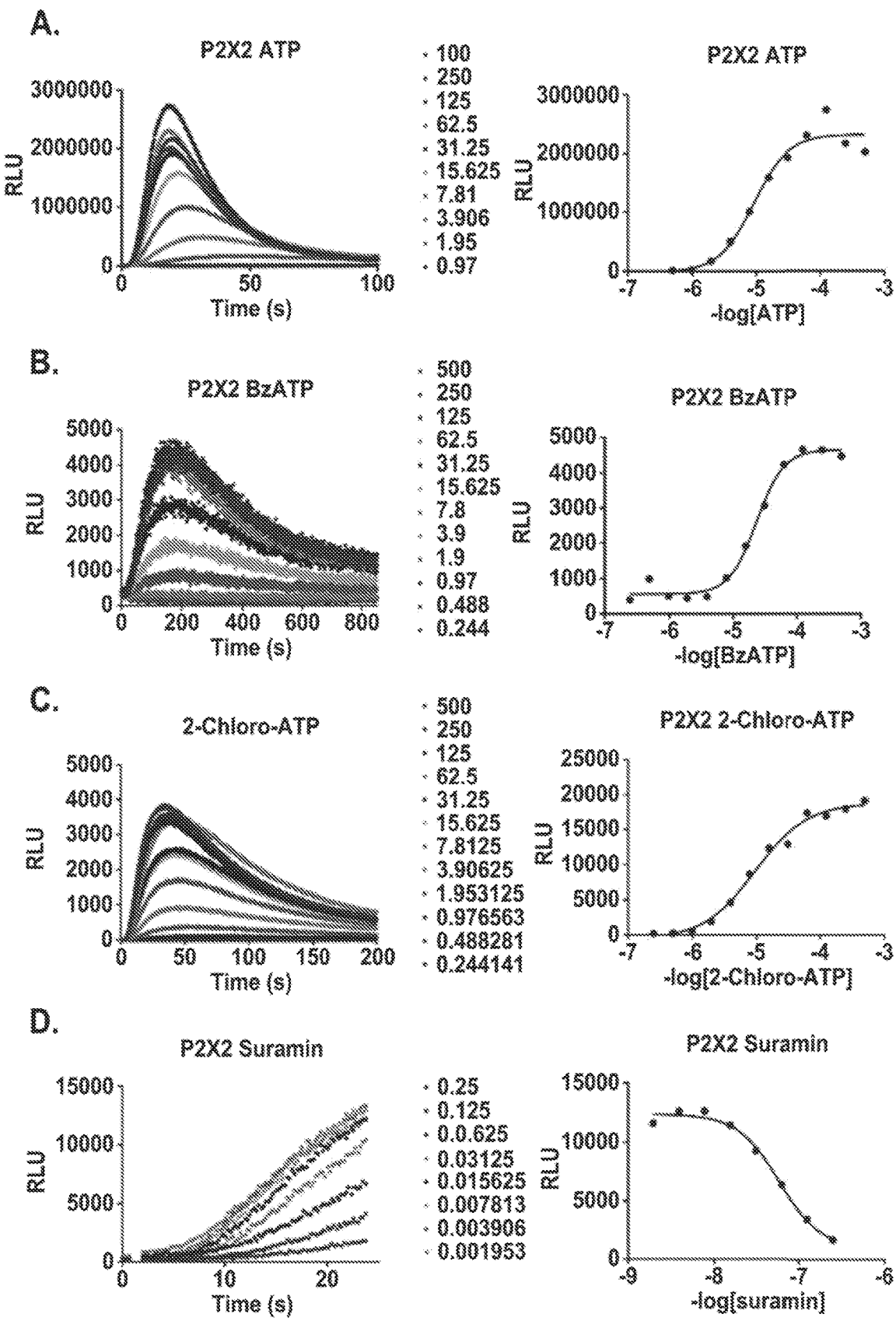
Fig. 10A-D

A.
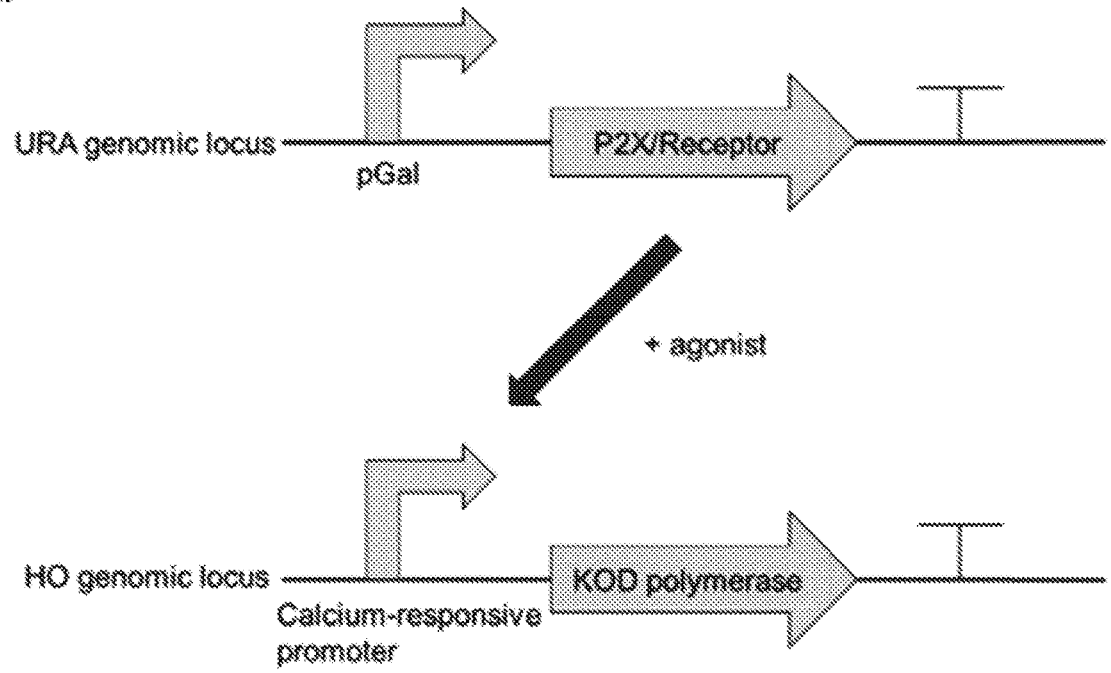
B.
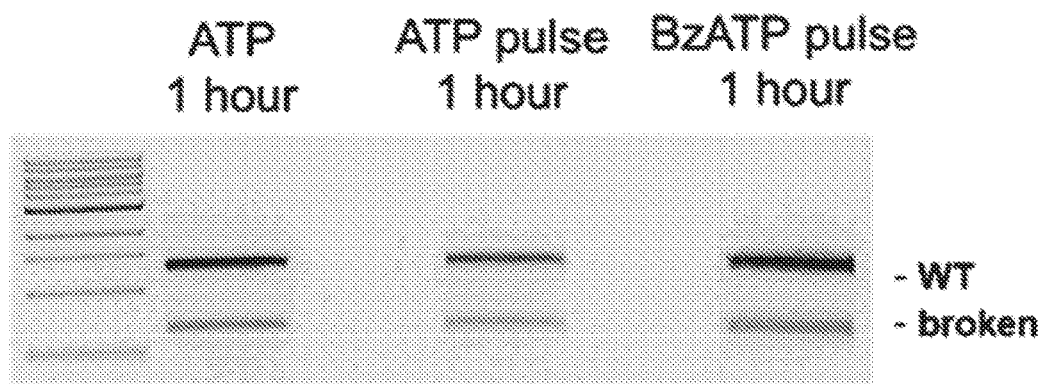
Fig. 11A-B

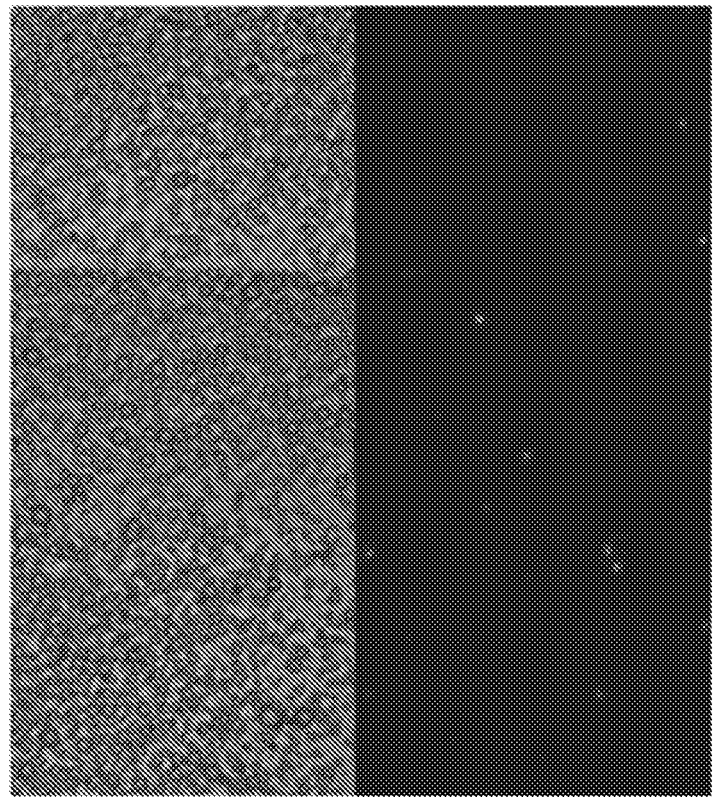
Fig. 12A-B
Fig. 13

Fig. 24A-B

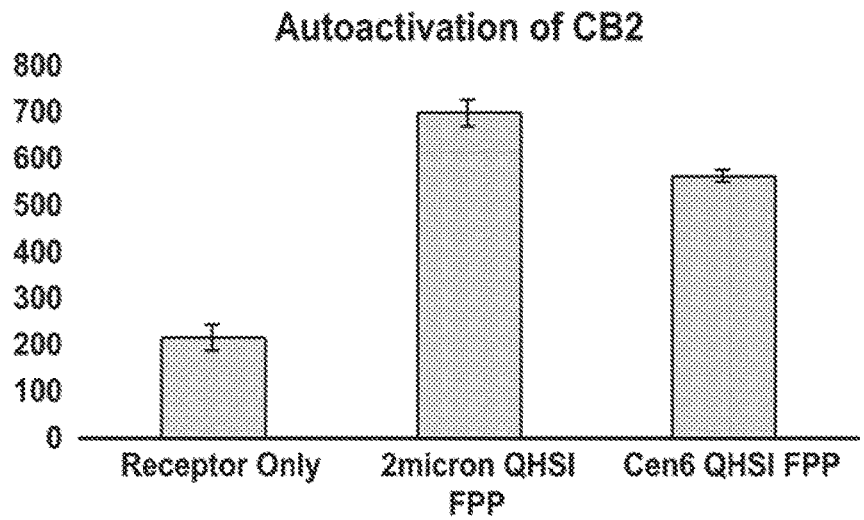
Fig. 34
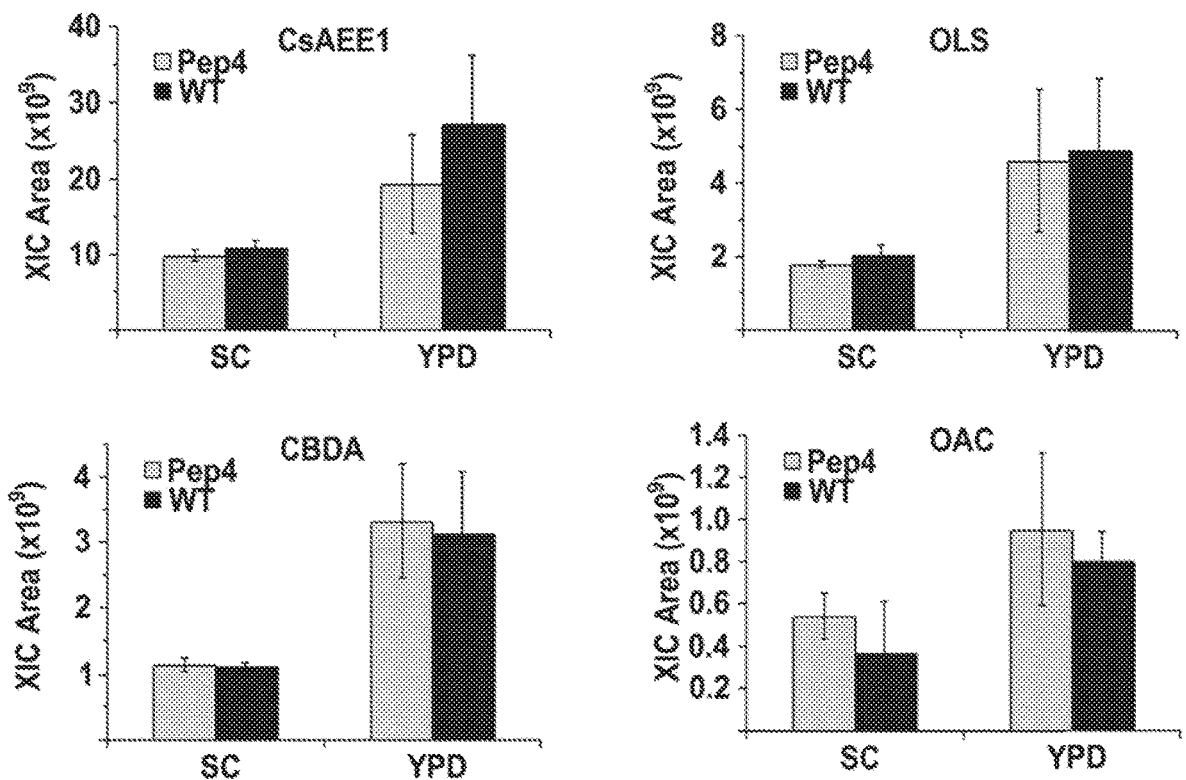
Fig. 35A-D

| Gene ID | Z-combined | Ave FC |
|---|---|---|
| KAR2 | 11.69 | 1.78 |
| ERO1 | 6.97 | 2.62 |
| PDI1 | 6.04 | 1.52 |
| MCD4 | 5.81 | 7.72 |
| LHS1 | 5.25 | 2.27 |
| SIL1 | 4.90 | 3.86 |
| YPS1 | 3.51 | 5.13 |
| MPD1 | 3.24 | 3.99 |
| DOG2 | 3.23 | 4.50 |
| SCJ1 | 3.22 | 1.99 |
| NCE103 | 3.11 | 1.51 |
| YMR315W | 2.97 | 1.55 |
| YIL108W | 2.88 | 2.14 |
| EUG1 | 2.68 | 1.83 |

Fig. 40B

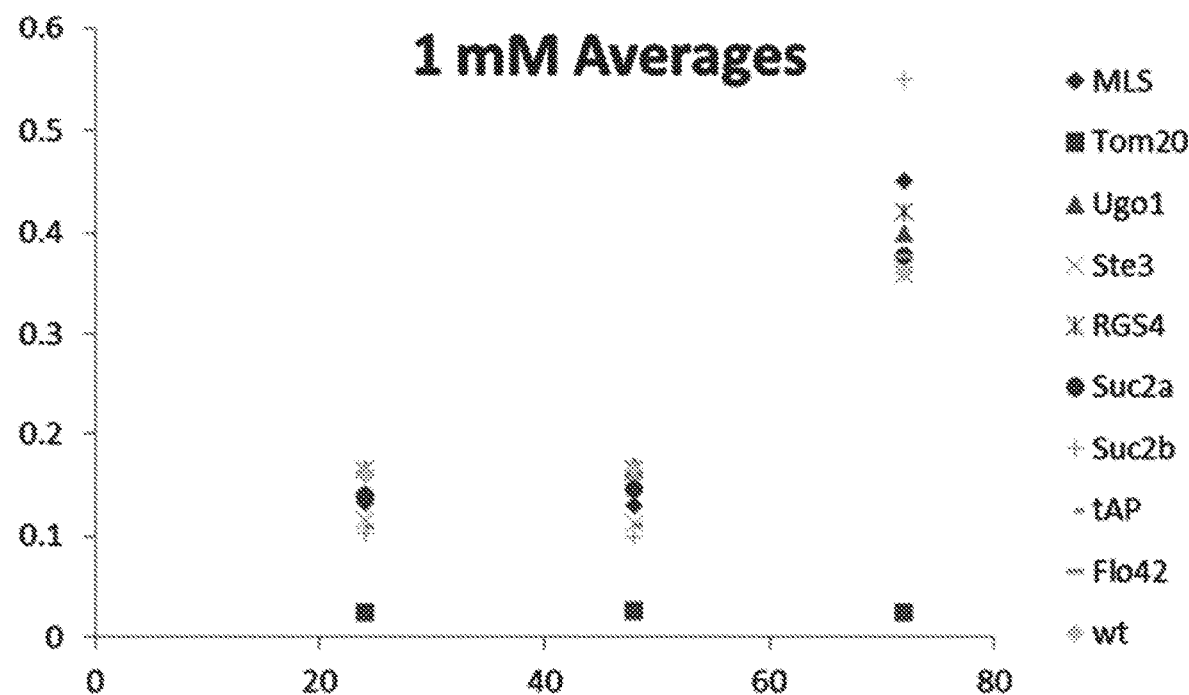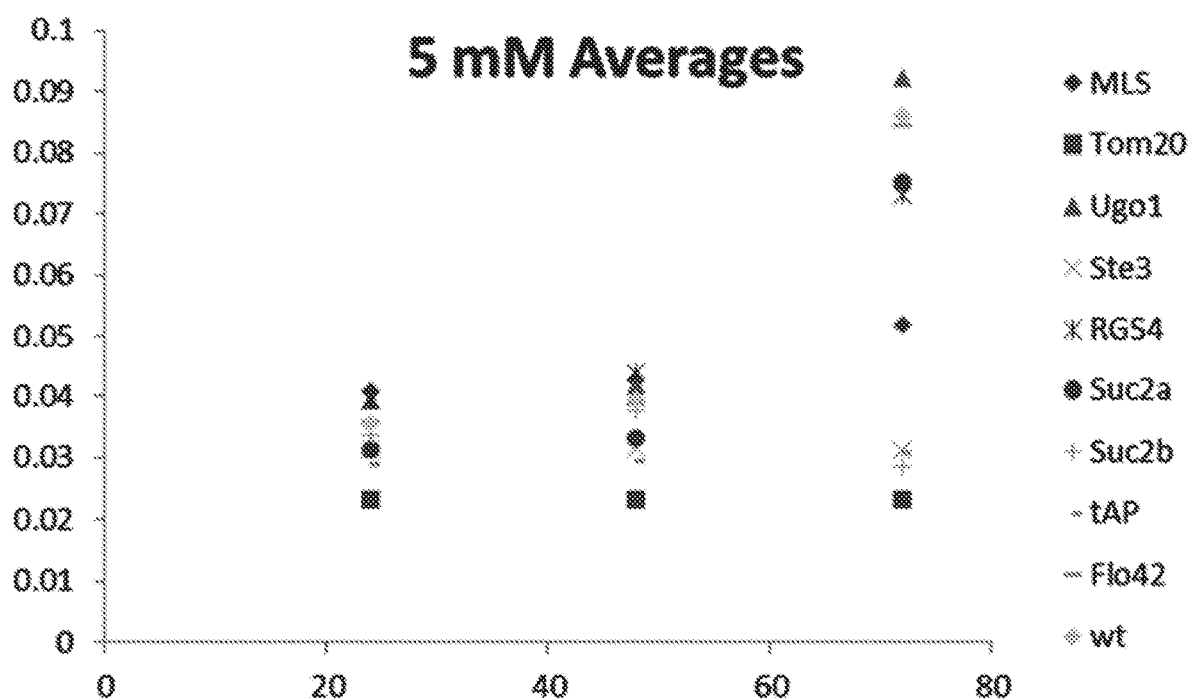
Fig. 42A-B

| Ligand | Receptor | Interaction | Distance | E (kcal/mol) |
|---|---|---|---|---|
| N6 36 | O LYS 70 (A) | H-donor | 2.76 | -2.3 |
| N6 36 | O THR 189 (A) | H-donor | 2.87 | -1.4 |
| O1G 2 | NH2 ARG 298 (A) | H-acceptor | 2.71 | -7.2 |
| O1G 2 | NZ LYS 316 (A) | H-acceptor | 2.69 | -17.8 |
| O2G 3 | NZ LYS 70 (A) | H-acceptor | 2.72 | -20 |
| O2G 3 | NZ LYS 72 (A) | H-acceptor | 2.7 | -20.1 |
| O2G 3 | NH2 ARG 298 (A) | H-acceptor | 2.69 | -7.2 |
| O3G 4 | NZ LYS 72 (A) | H-acceptor | 2.66 | -5.1 |
| O2B 6 | ND2 ASN 296 (A) | H-acceptor | 2.73 | -5.7 |
| O2B 6 | NZ LYS 316 (A) | H-acceptor | 2.82 | -9.3 |
| O1B 7 | NZ LYS 316 (A) | H-acceptor | 2.96 | -9 |
| O1A 10 | NZ LYS 70 (A) | H-acceptor | 2.76 | -15.6 |
| O3A 12 | O HOH 677 (A) | H-acceptor | 2.81 | -1.5 |
| O3' 22 | O HOH 678 (A) | H-acceptor | 2.77 | -1.5 |
| N1 39 | OG1 THR 189 (A) | H-acceptor | 2.76 | -2.9 |
| O1G 2 | NH2 ARG 298 (A) | ionic | 2.71 | -6.7 |
| O1G 2 | NZ LYS 316 (A) | ionic | 2.69 | -6.9 |
| O2G 3 | NZ LYS 70 (A) | ionic | 2.72 | -6.7 |
| O2G 3 | NZ LYS 72 (A) | ionic | 2.7 | -6.8 |
| O2G 3 | NH2 ARG 298 (A) | ionic | 2.69 | -6.9 |
| O3G 4 | NZ LYS 72 (A) | ionic | 2.66 | -7.2 |
| O3G 4 | NH2 ARG 298 (A) | ionic | 3.88 | -0.8 |
| O2B 6 | NZ LYS 70 (A) | ionic | 2.8 | -6 |
| O2B 6 | NZ LYS 316 (A) | ionic | 2.82 | -5.8 |
| O1B 7 | NZ LYS 316 (A) | ionic | 2.96 | -4.7 |
| O1A 10 | NZ LYS 70 (A) | ionic | 2.76 | -6.3 |
| 6-ring | CD LYS 72 (A) | pi-H | 3.56 | -0.7 |

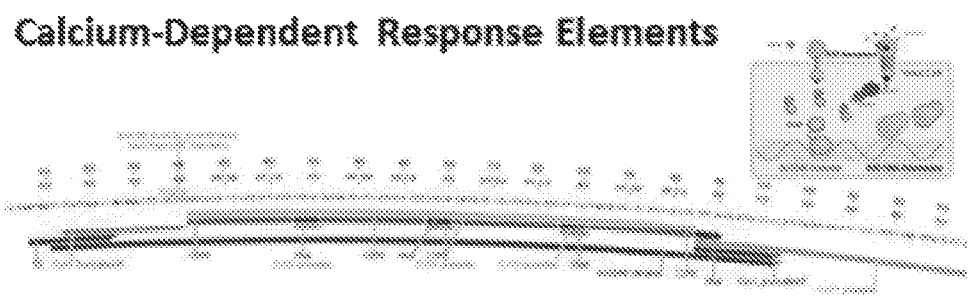
FIGURE 52A-C

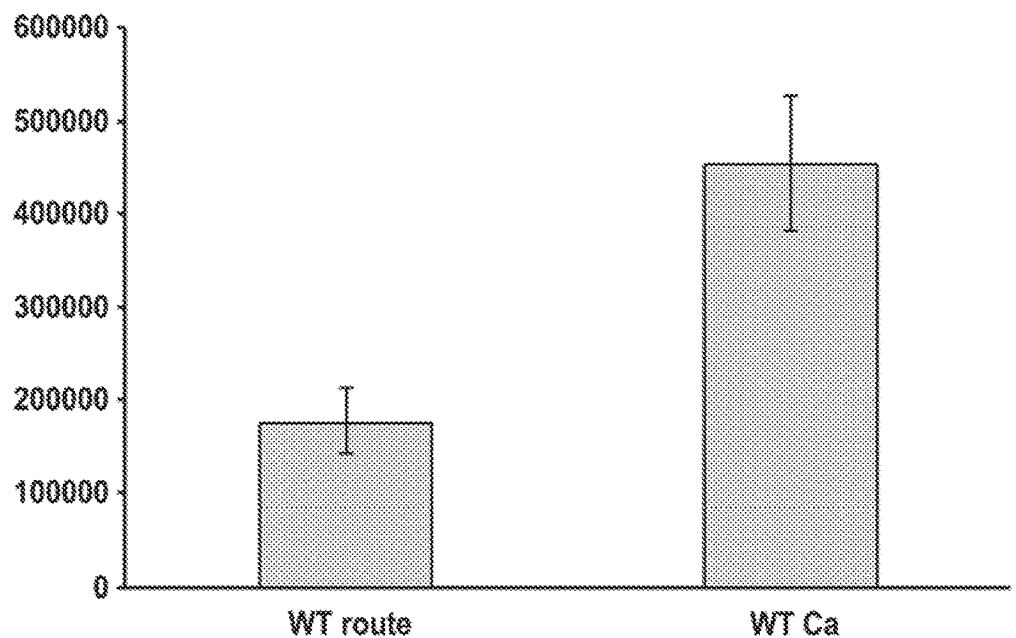
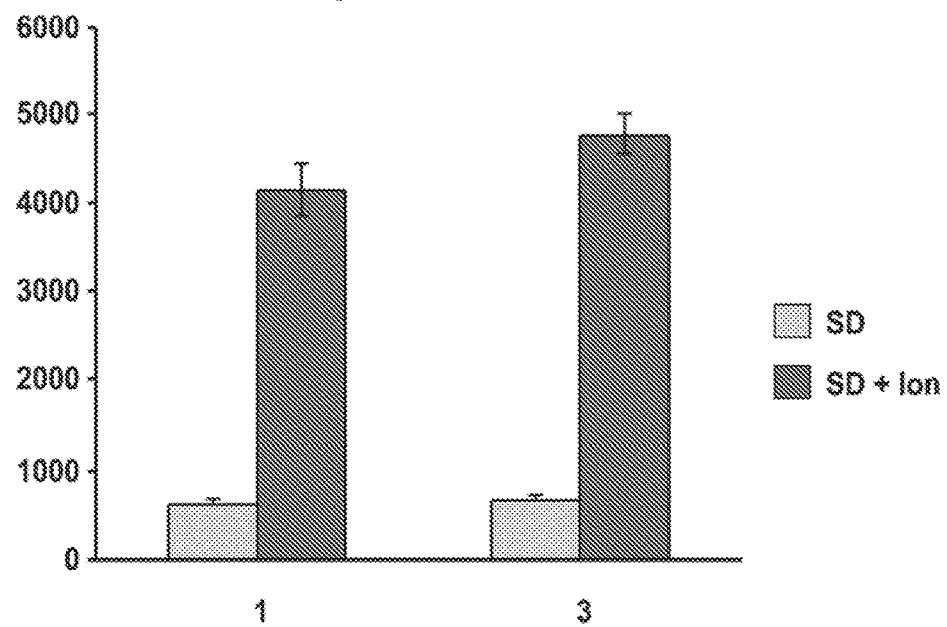
Fig. 52A-C Cont.

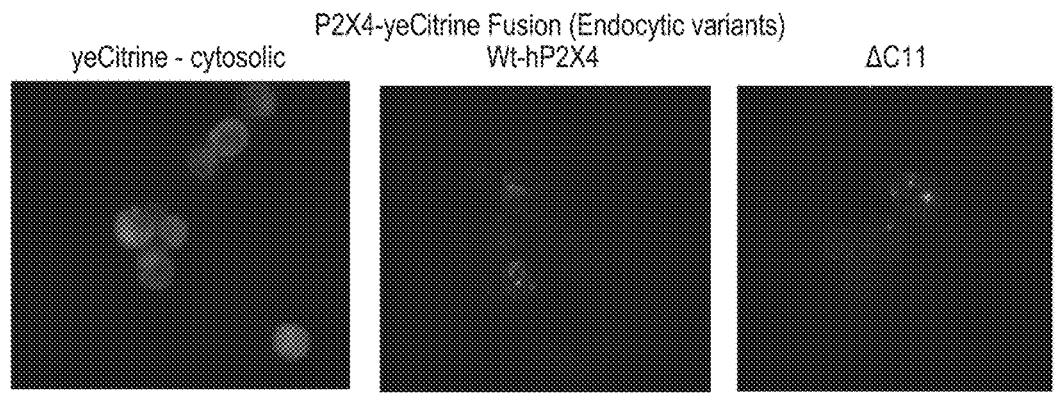
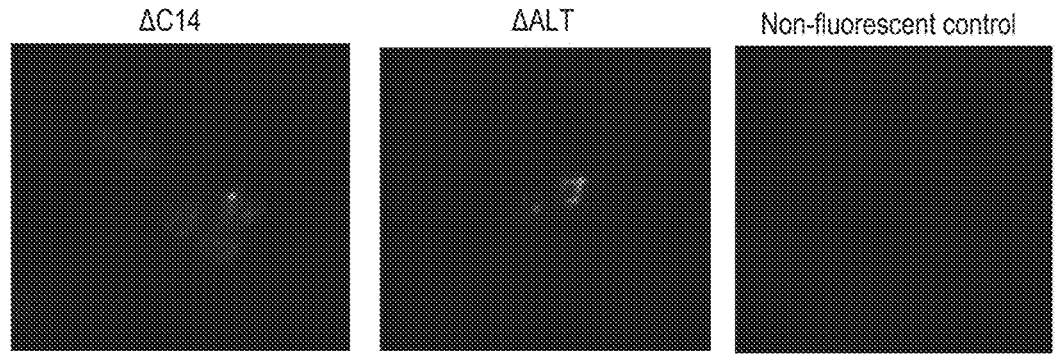
FIG. 55A  FIG. 55B  FIG. 55C
FIG. 55D  FIG. 55E  FIG. 55F
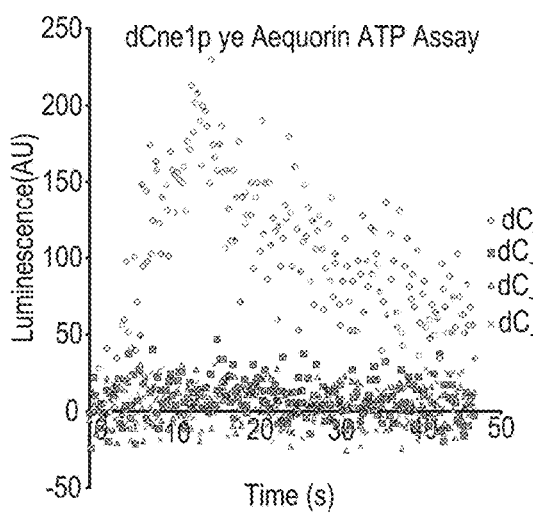
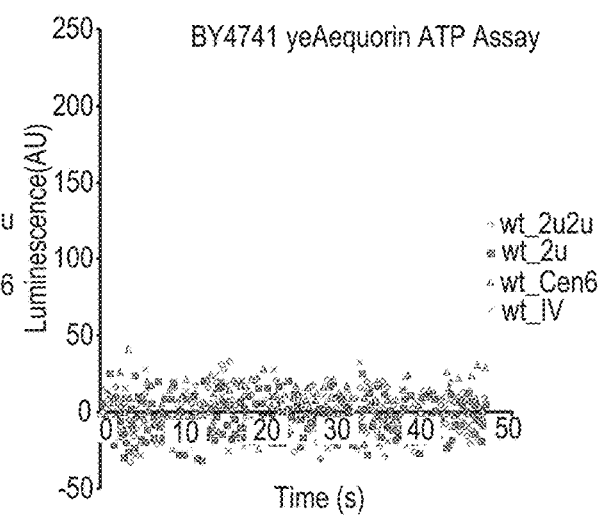
FIG. 56A  FIG. 56B

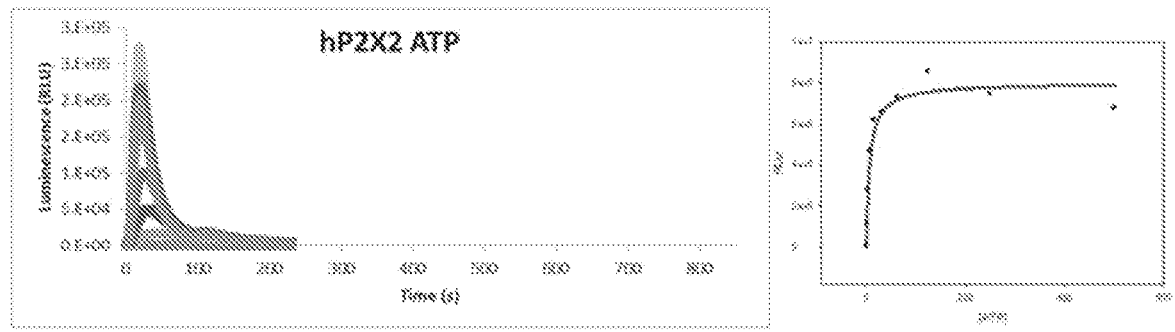
FIGURE 58A-B
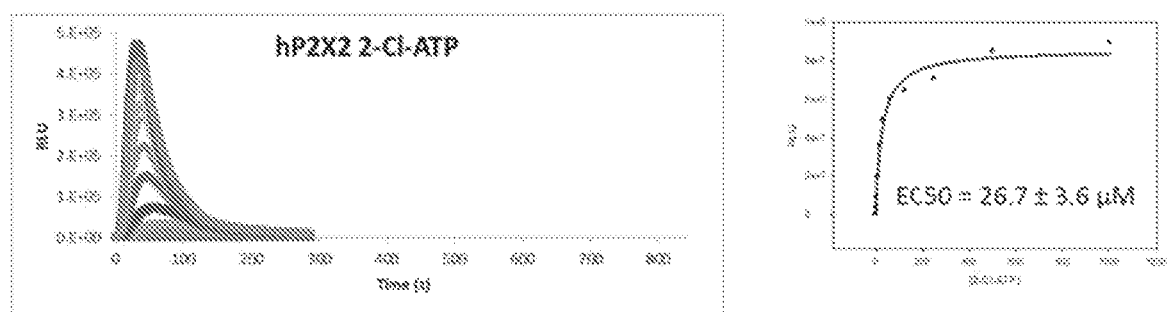
FIGURE 59A-B
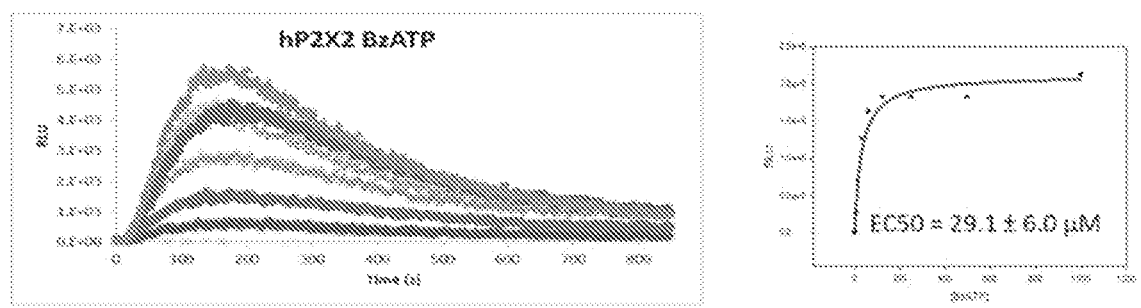
FIGURE 60A-B

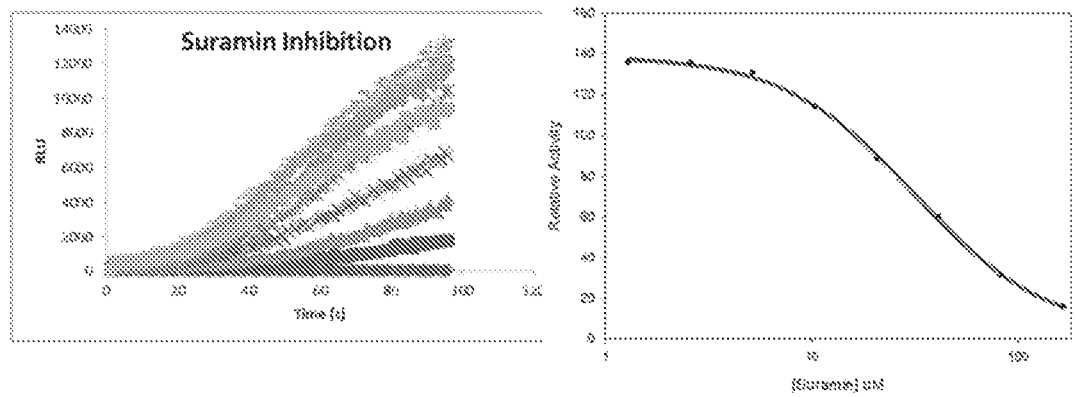
FIGURE 61A-B
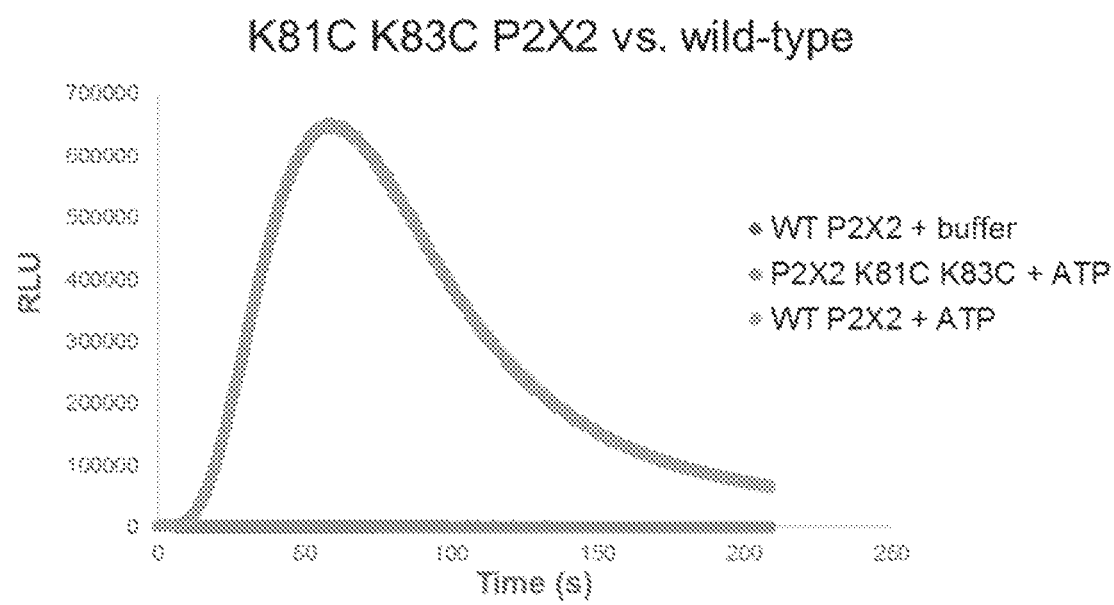
FIGURE 62

FIGURE 63A-B

METHODS AND PLATFORM FOR SCREENING AND SELECTING METABOLITES AND THEIR RECEPTORS

CROSS-REFERENCE TO RELATED APPLICATIONS

This application claims benefit of U.S. Provisional Application No. 62/520,189, filed Jun. 15, 2017, and PCT Application No. PCT/US2018/037818, filed Jun. 15, 2018, both of which are incorporated herein by reference in their entirety.

BACKGROUND

Orthogonal GPCRs have been used by neuroscientists to selectively depolarize neural subtypes and thereby selectively probe the function of particular neurons or sets of neurons. In recent years, this has been accomplished by integrating human GPCRs with native pheromone signaling pathways in *Saccharomyces cerevisiae*, and then screening and evolving receptors to respond to a wide variety of drug-like molecules. The chemogenetic receptors developed by this technology have been termed DREADDS (designer receptors exclusively activated by designer drugs) (Alexander 2009). While various $G_i$-, $G_q$-, and $G_s$-coupled DREADDs have been widely used by the neuroscience community for interrogations of neural function, there is still a dearth of orthogonal receptor: ligand pairs, which has in turn prevented multiplexing several DREADDs in a single organism to probe more complex neural interactions. Since the origination of DREADDs, the workhorse ligand has been clozapine-N-oxide (CNO), which is used for the excitatory hM3Dq DREADDs and the inhibitory hM4D, as well as Gs and β-arrestin-coupled DREADDs (Nakajima 2012). Only recently has a second salvinorin B ligand become available for a rationally designed kappa-opioid receptor-based DREADD, meaning there are now only two simultaneously accessible DREADDs (Vardy 2015). In order to develop more complex probes of neural function, especially as the inherent differentiation of neurons in the brain has begun to be mapped with exquisite resolution, many more functional orthogonal receptor:ligand pairs are necessary.

Previous selection strategies used to evolve DREADDs had the limitation of requiring growth assays, which confounded signaling with fitness effects caused by the ligand or receptor. In addition, selection for fitness can readily result in "cheaters" that yield improved growth due to mutations outside the target gene. What is needed in the art are methods of altering yeast GPCR display platform to select not on the basis of growth, but on the basis of the production of a thermostable polymerase and subsequent emulsion PCR.

An additional limitation of previous selection strategies is that they lacked negative selections against native (or other) ligands, instead employing extensive screening for ligands that would not activate existing DREADDs. What is needed is a novel negative selection, rather than a screen, which can allow for easy and simultaneous validation of the orthogonality of many mutually-exclusive GPCR-ligand pairs.

One of the most daunting problems for producing and introducing new DREADDs is the painstaking identification of compounds that will be truly specific, and not otherwise impact the extensive set of neural receptors and interactions in the brain. While to date this has relied on identifying the very few compounds that can cross the BBB and fit in the pocket of a slightly altered neural GPCR, what is needed is an alternative strategy that can pave the way to many more orthogonal effectors.

No current technology allows for both the production of a compound in an organism and the concomitant functional modulation of a signal transduction pathway. No current technology conveniently allows barcoding and amplification of that barcode based on receptor or signal transduction pathway activation.

SUMMARY

Disclosed herein are methods and platforms using Receptor Compartmentalized Partnered Replication (CPR), in which the partner gene is a receptor, signal transduction pathway, or metabolic pathway that leads to the production of an effector molecule for the receptor or signal transduction pathway. The signal transduction pathway or receptor is coupled to the production of a thermostable polymerase. Emulsification of libraries of organisms with primers that can amplify the partner gene led to the selective amplification of those partner genes that were best able to produce the thermostable polymerase during thermal cycling of the emulsion.

BRIEF DESCRIPTION OF THE DRAWINGS

The accompanying drawings, which are incorporated in and constitute a part of this specification, illustrate several embodiments and together with the description illustrate the disclosed compositions and methods.

FIGS. 3A and 3B shows beta-caryopyllene biosynthesis and autoactivation. FIG. 3A shows the biosynthesis scheme for producing beta-caryophyllene in yeast. Enzymes in green have been heterologously expressed. Enzymes in orange are upregulated by UCP2-1 transcription factor. Enzymes in red have been engineered with extra copies in the genome. FIG. 3B shows autoactivation of the CB2 receptor by beta-caryophyllene production in the same strain. QHSI was introduced on 2 micron and CEN6 plasmids. Y axis is GFP production read as relative fluorescence.

FIG. 4A-C shows yeast CSR. FIGS. 4A and 4B show water-in-oil emulsions with single cells expressing a fluorescent reporter. After successive rounds of optimization, yeast expressing KOD were able to successfully amplify the targeted genome insertion at the URA3 locus. FIG. 4C (the gel) shows the last round of primer concentration optimization.

FIGS. 8A and 8B shows P2X family receptor screen. P2X receptors 1-7 were expressed from pGal promoters and integrated into the URA-site in the yeast chromosome V. FIG. 8A, P2X1, P2X2, P2X4, and P2X7 show functional gating. FIG. 8B, P2X2 is orders of magnitude higher signal-to-noise than the others.

FIG. 9A-B shows P2X4 confocal microscopy. WT P2X4 (9A) and a P2X4Δ14 C-terminally truncated receptor (9B) with an ER export signal were expressed in yeast and imaged with confocal microscopy. The wild-type cells show intracellular aggregates, but the truncated P2X4 shows a more diffuse localization characteristic of ER localization.

FIG. 10A-D shows P2X2 kinetic analysis. Dose response assays were performed on P2X2 receptors expressed in yeast. Agonists tested include ATP (10A), 2-Chloro ATP (10C), and BzATP (10B). The inhibitor suramin (10D) was also tested.

FIG. 11A-B shows mock selections. 11A shows circuit diagram of CPR scheme. The KOD reporter enzyme is induced when its partnered gene, the receptor, is activated by agonist. 11B shows wild type and broken P2X2 receptors (containing restriction enzyme site) were incubated with ligand. Ligand incubation conditions were varied to include a single ATP dose of 100 uM (lane 1), four ATP doses (lane 2), or four BzATP doses (lane 3). Cells were consolidated before emulsion PCR of the P2X gene. Amplicons were digested with restriction enzyme to differentiate WT from broken before running the gel.

FIG. 12A-B shows yeast emulsion images. 12A shows brightfield images of representative emulsions. 12B shows fluorescent microscopy of intact cells within emulsions. Cells are not disrupted upon emulsification.

FIG. 13 shows stability of yeast emulsions example. Unstable emulsions phase separate. Shown is a gradient of stability observed.

FIG. 24A shows library of polymerase and PCNA variants are cloned into S. cerevisiae (clone shown in 24B) The cells are emulsified after induction of the replication machinery. During emPCR, replication machinery variants are guided by primers to amplify individual variants. Variants of higher fitness that are capable of successfully amplifying themselves will dominant the recovered pool.

FIG. 34 shows autoactivation of the CB2 receptor by beta-carophyllene production in the same strain. QHSI was introduced on 2 micron and CEN6 origins and CB2 stimulation was read by ZsGreen reporter. Error bars represent the standard deviation of replicate measurements.

FIG. 35A-D shows proteomics analysis of pathway enzymes. Spectral counts of each of the soluble CBD pathway enzymes (A-D) are shown. Enzymes were expressed in BY4747 (wt) and ΔPep4 strains. Protein abundances in cells grown in synthetic complete (SC) or rich (YPD) media were also measured.

FIGS. 40A and 40B shows unfolded protein response observed in cells with pathway. 40A shows a schematic and 40B shows a table.

FIGS. 42A and 42B shows that aromatic prenyltransferase variants alone do not confer robust growth in hexanoic acid. Growth of aromatic prenyltransfersae variants in the presence of 1 mM (42A) and 5 mM (42B) hexanoate-supplemented media. Each point represents the average growth of 3 independent colonies. Time points were taken in 24 hour intervals.

Measurements were taken after 3 days of growth in media supplemented with 10 mM hexanoic acid and 1% acetate. The variants are numbered the same as FIG. 6-16. Variant 10 is the unaltered wildtype aromatic prenyltransferase.

Figure 46A:
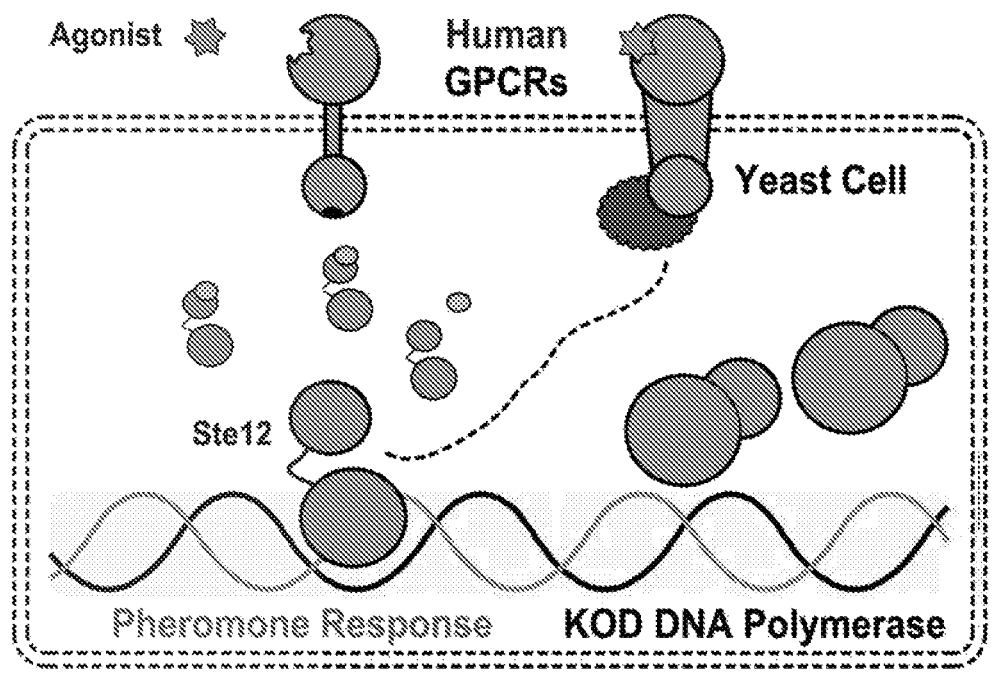
Figure 46B:
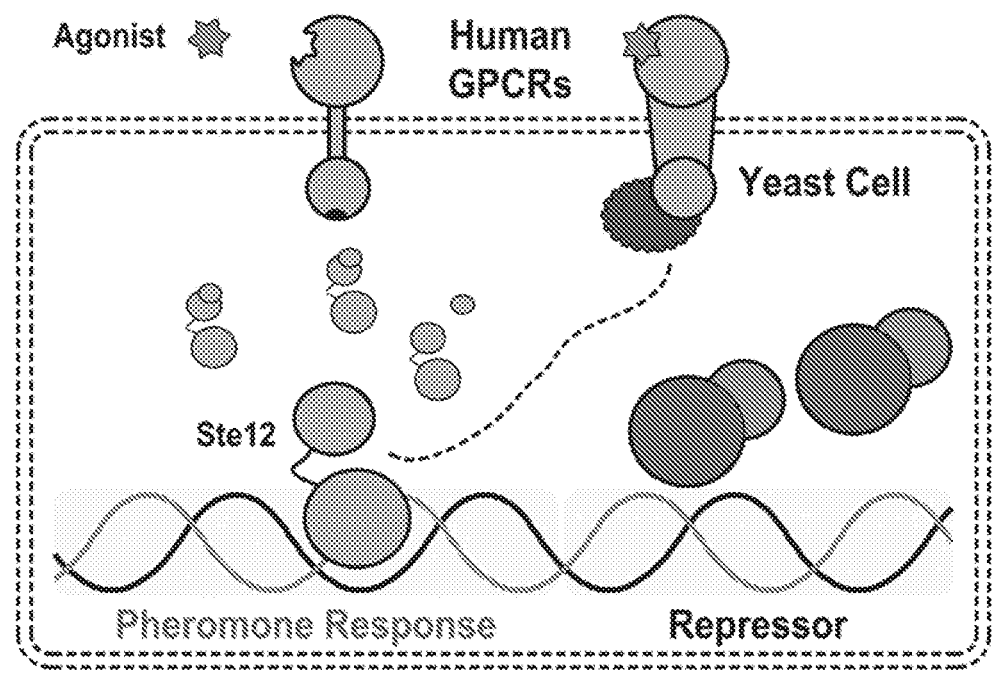

FIGS. 46A and 46B shows agonist and antagonist CPR results. 46A shows agonist CPR. Ligand induces the production of DNA polymerase, which is then used in emulsion PCR. 46B shows antagonist CPR circuit. Agonism of the receptor leads to the production of a repressor, which then in turn inhibits the production of a thermostable DNA polymerase for use in emulsion PCR. Only when the receptor is blocked is it possible to produce polymerase.

Figure 47B:
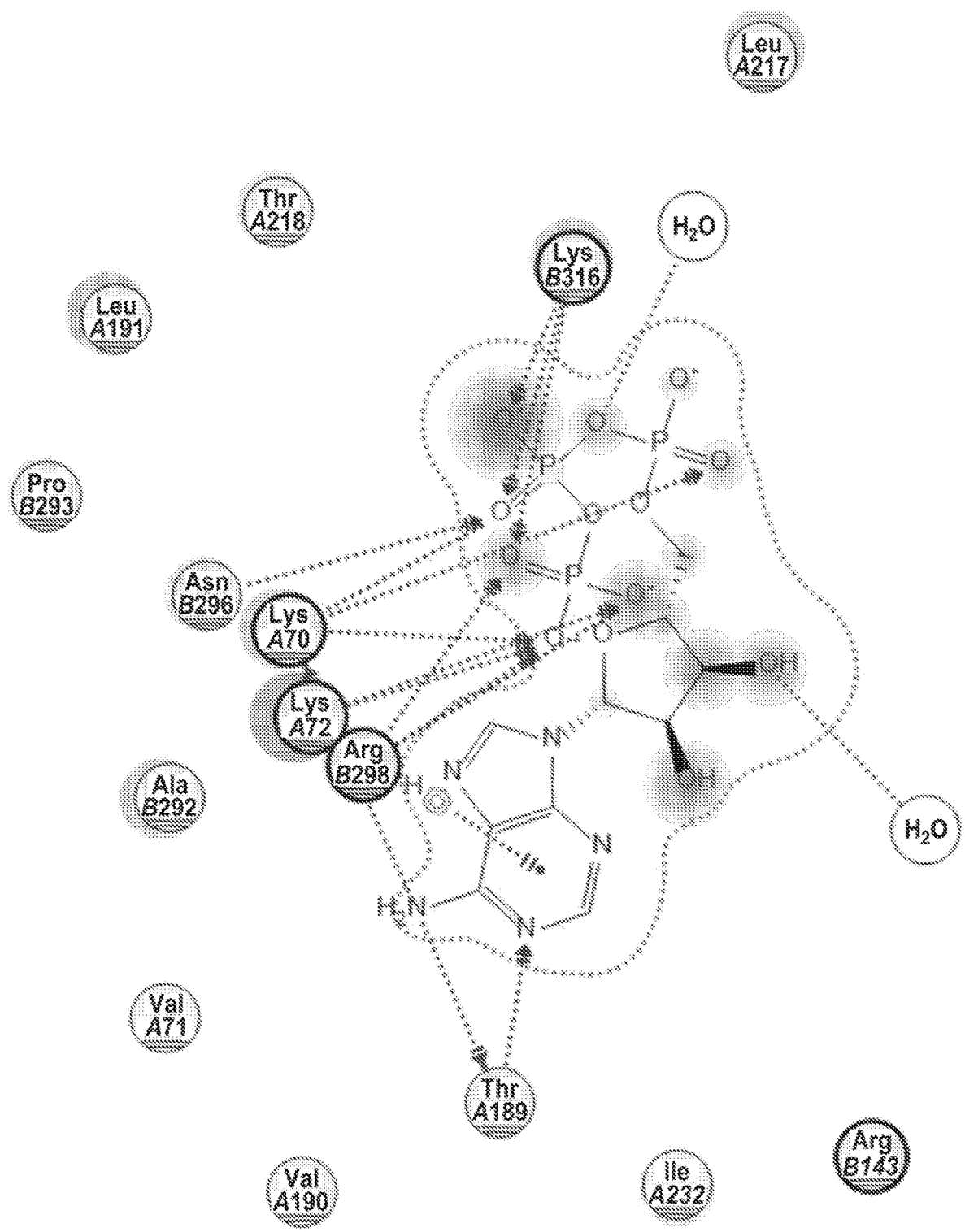

FIG. 47A-B shows ligand interactions of ATP with P2X4. FIG. 47A shows ATP interactions with P2X4 are tabulated. FIG. 47B shows 2D contact map of ATP bound to the wildtype structure. Basic residues are highlighted in blue. Polar contacts are depicted with arrows.

Figure 48:
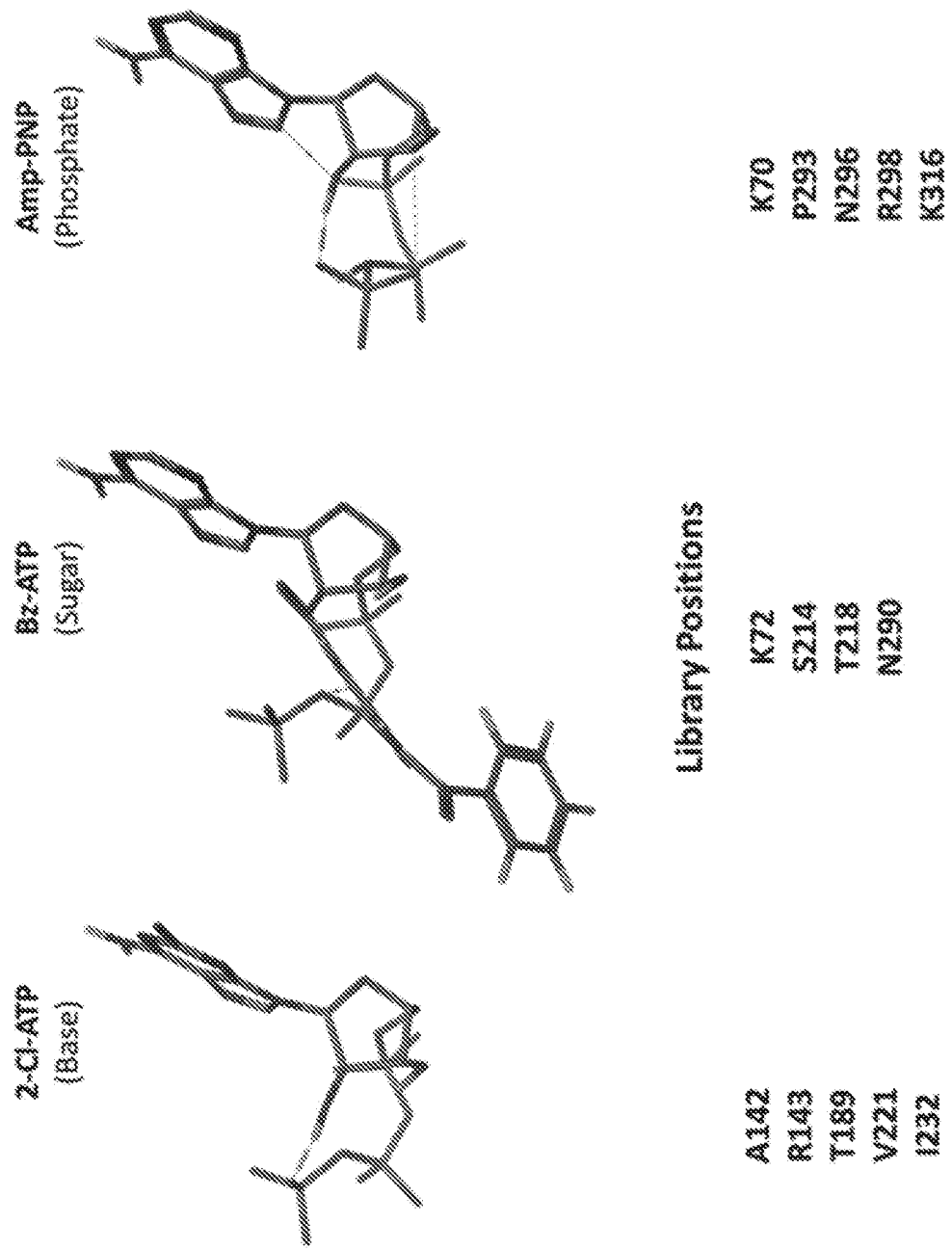

FIG. 48 shows training molecules and amino acid residues used in the design of P2X4 receptor variants.

Figure 49:
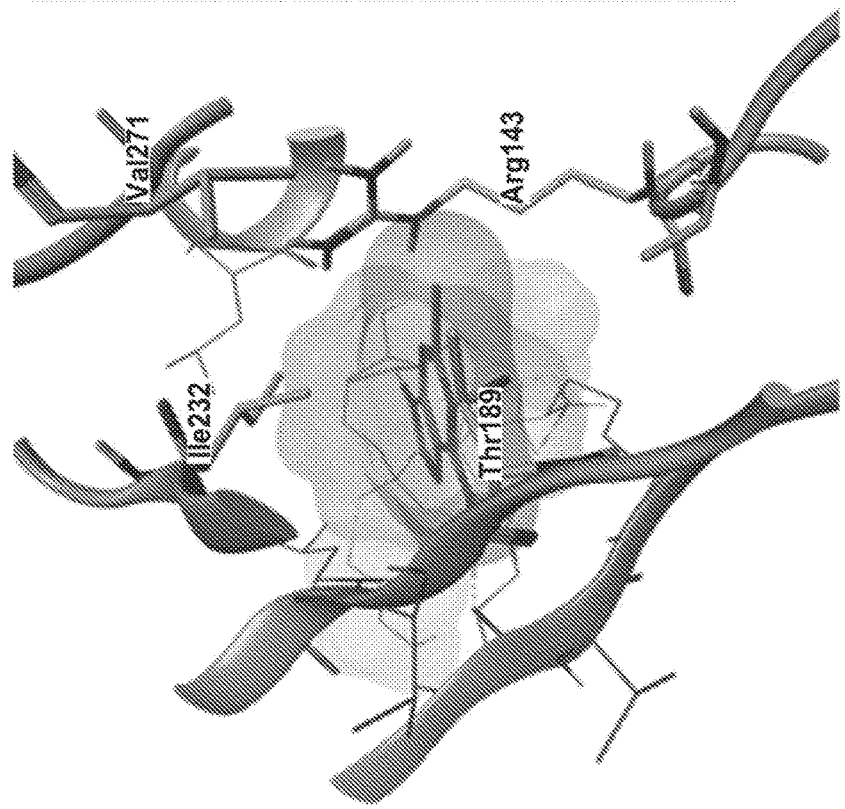
Figure 50:
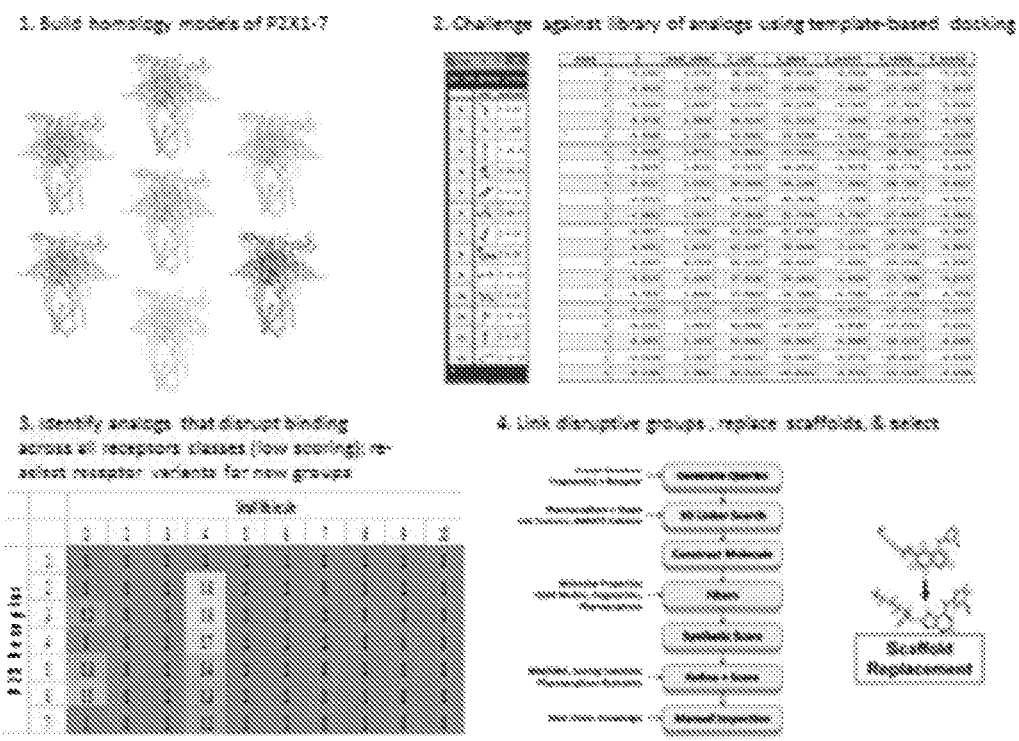

FIG. 49A-B shows in silica selection of P2X4 variants to 2-Cl-ATP. FIG. 49A shows library residues for in silica selection are shown in blue. 2-Cl-ATP is depicted in magenta and with a molecular surface. FIG. 49B shows representative in silica selection data of top 10 computationally derived P2X4 variants.

FIG. 50A-D shows analog screening methodology. Methodology for selection of orthogonal receptor:ligand pairs. A. Homology models were constructed for each of the P2X receptor subtypes. B. Models are screened against a number of small molecules. C. Small molecules are scored with quantitative structure activity relationships and given scores. D. Candidate molecules are transformed into druggable molecules through by replacing the scaffold of the selected molecule.

Figure 51:
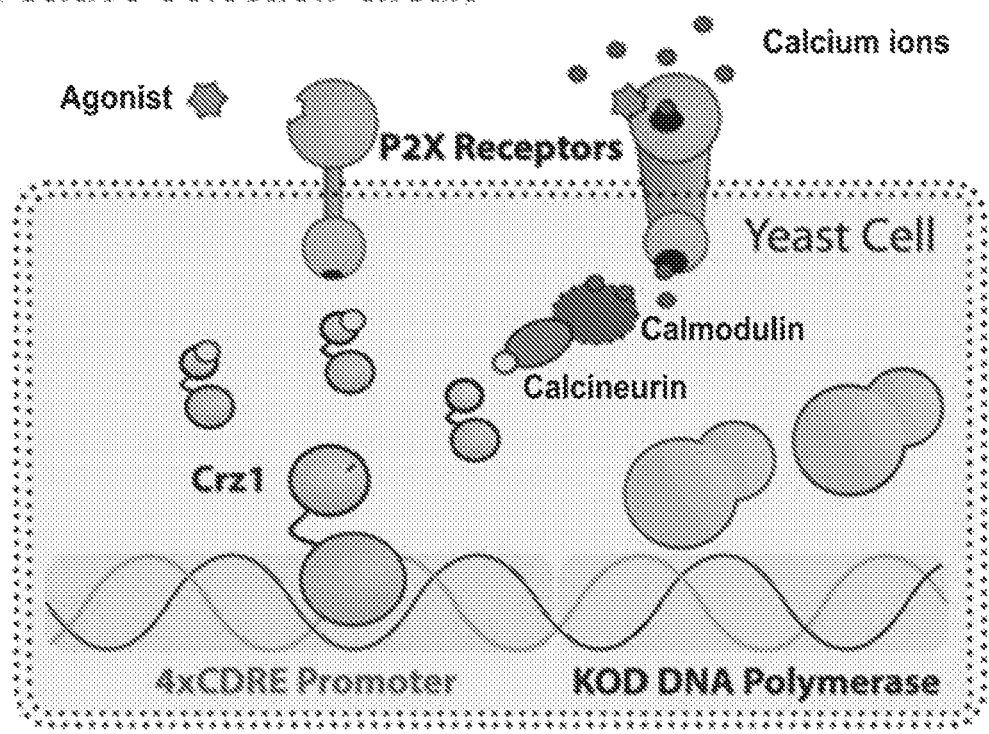

FIG. 51 shows Positive selection circuit. DNA polymerase is induced by calcium intake from P2X receptor variants. via the Crz1-dependent pathway. The amount of polymerase produced in each cell is directly influenced by receptor function.

FIG. 52A-C shows calcium dependent response element characterization. A shows depiction of 4×CDRE-Cyc 1 hybrid promoter. B shows passive diffusion of calcium triggers the promoter when compared to a control. C shows the addition of an calcium ionophore triggers expression of a fluorescent reporter under the control of 1× and 3×CDRE hybrid promoters.

Figure 53:
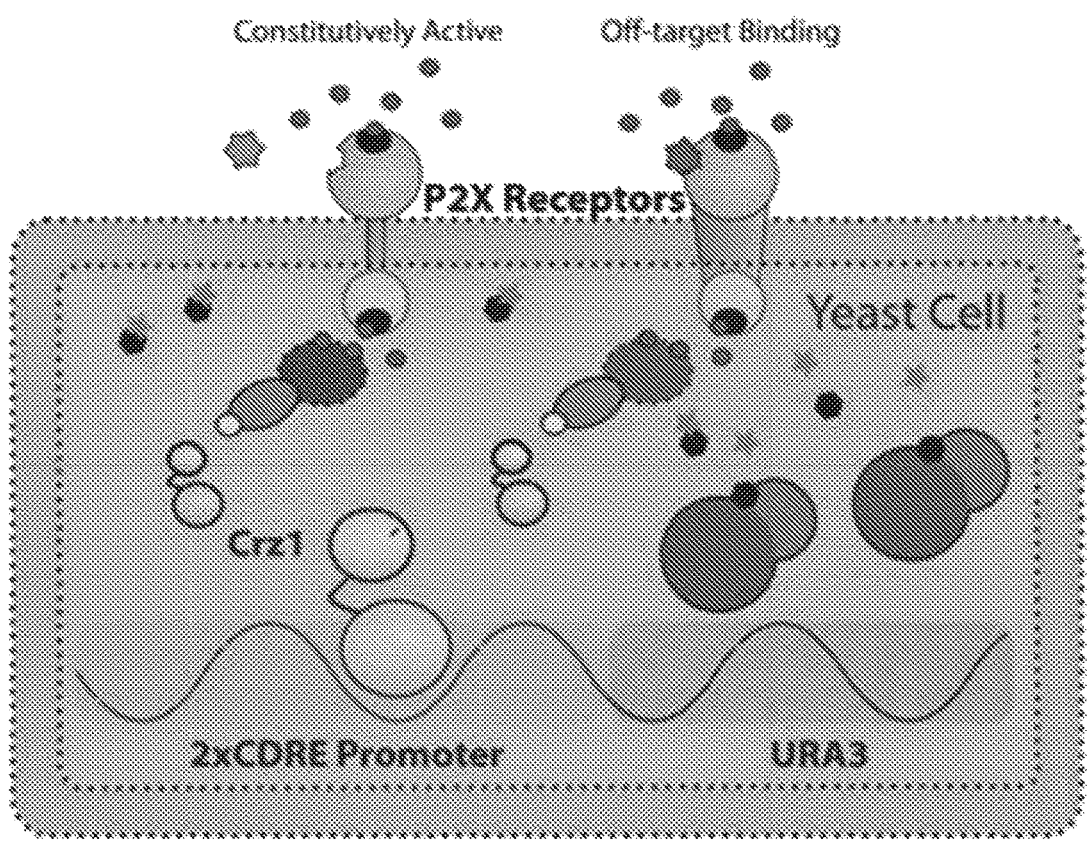
Figure 54A:
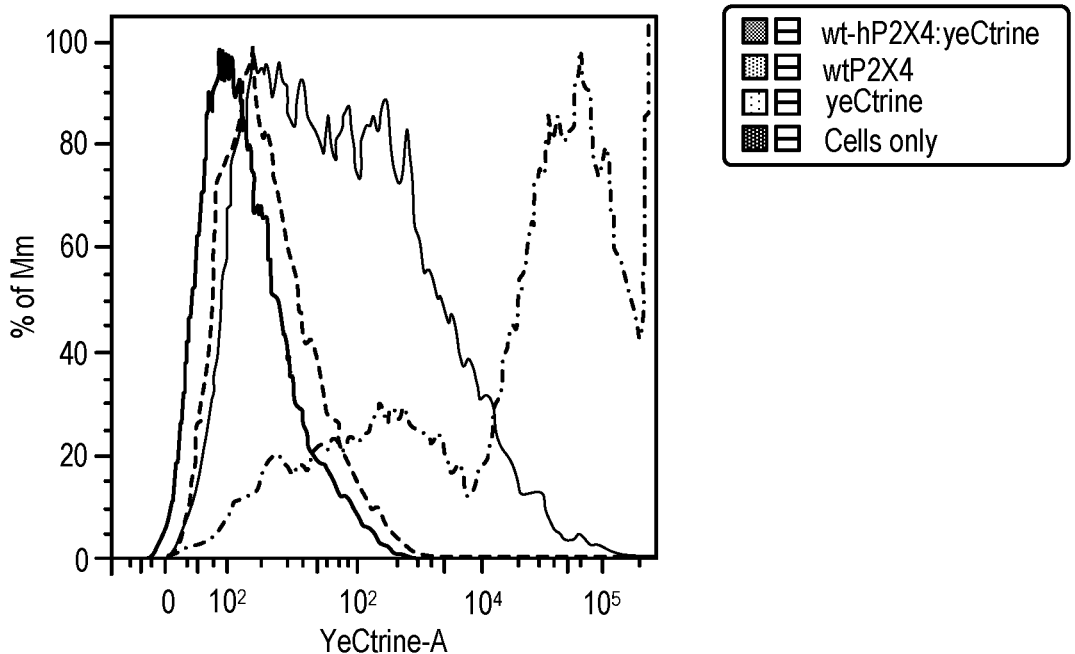
Figure 54B:
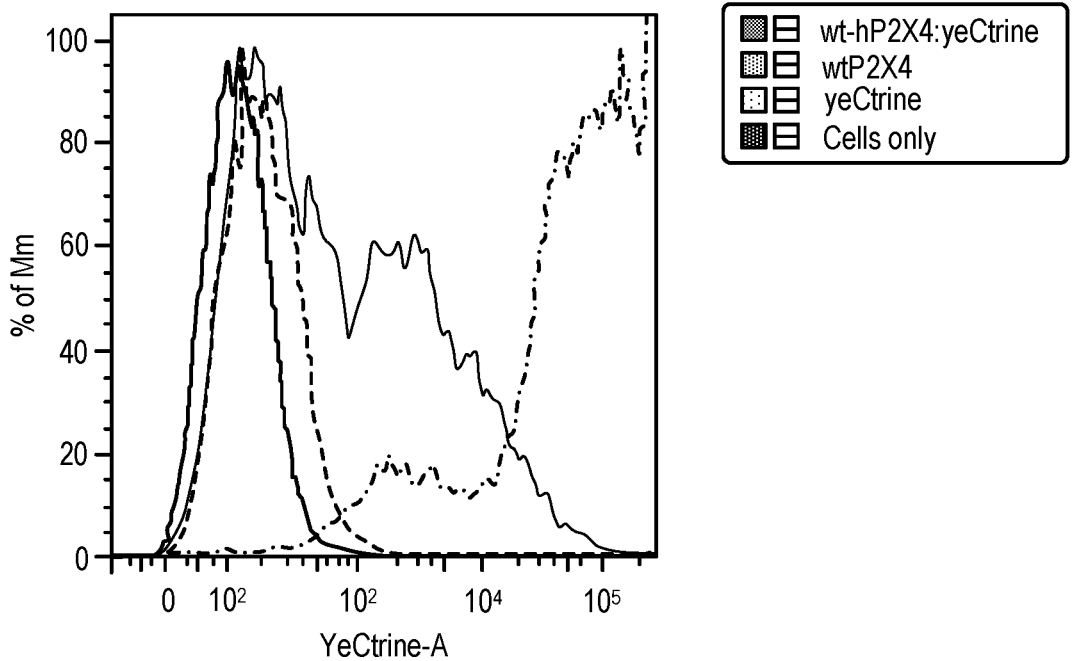
Figure 54C:
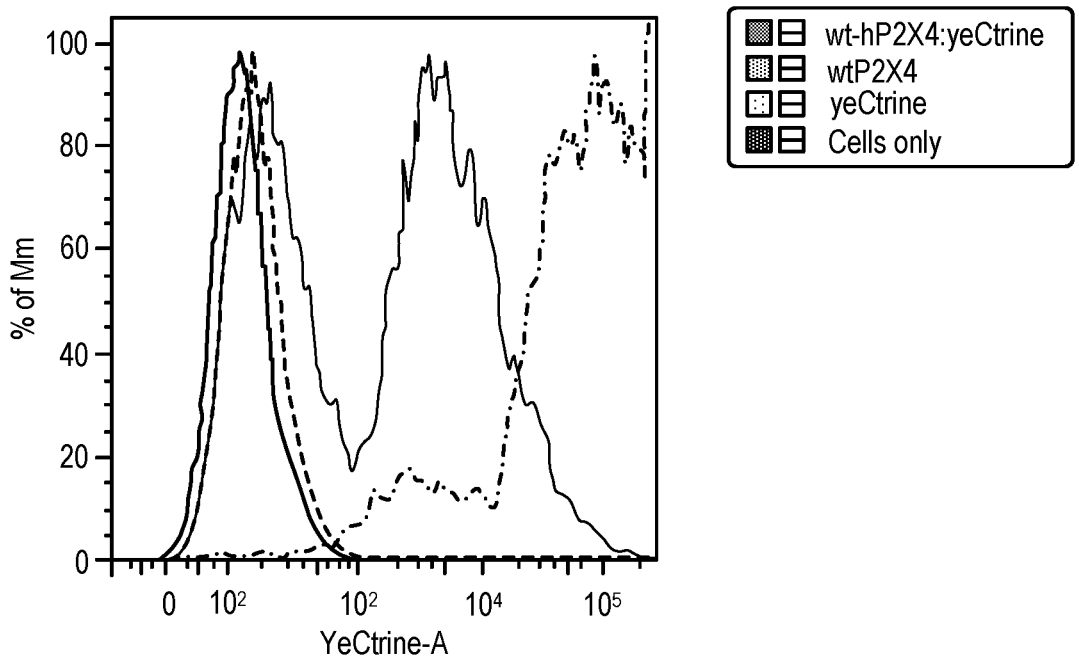
Figure 54D:
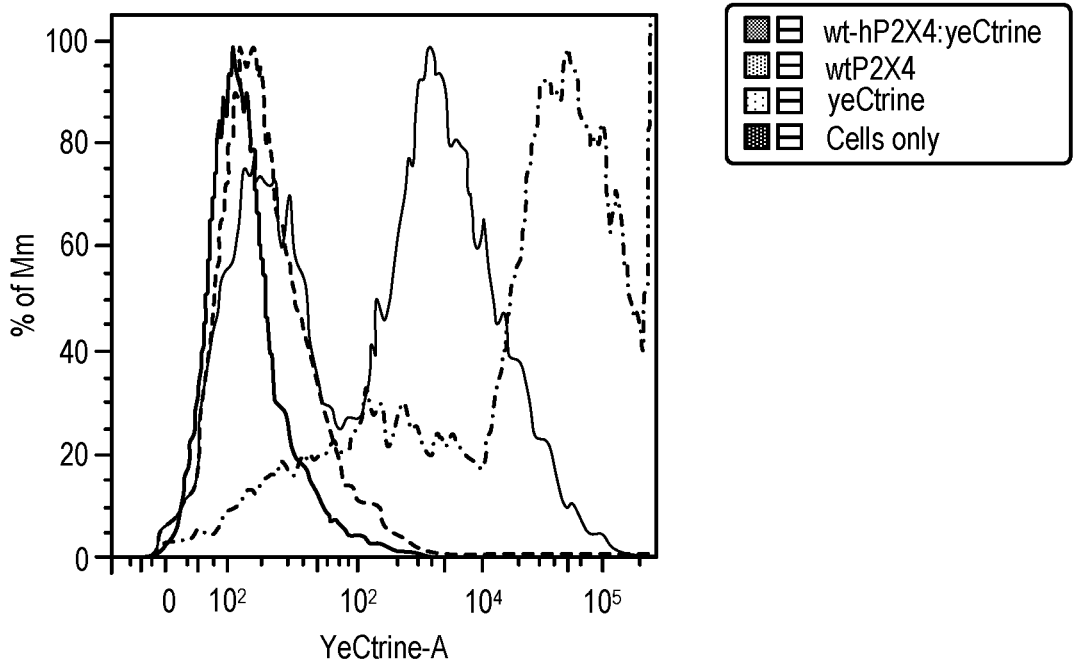

FIG. 53 shows a negative selection circuit. URA3 is produced in the presence of constitutively active and off-target binding receptors. URA3 converts 5-FOA to 5-FU and kills the cell.

FIG. 54A-D shows flow cytometry reveals expression of P2X4 in yeast. Flow cytometry of low-copy plasmid expression testing of fluorescently-tagged hP2X4 receptors in BY4741 (A and B) and BY4741ΔCne1p (C and D). See key for traces.

FIG. 55A-F shows localization of P2X4 in yeast. Confocal microscopy of wtP2X4 and endocytic variants (A-F). ΔC14 was judged to be largely absent from intracellular vacuoles when compared to the wt receptor.

FIG. 56A-B shows function assay of P2X4. Functional testing of hP2X4ΔC14 using a plate-reader based aequorin assay. Each point represents the average of three independent test. Only when the receptor and aequorin were expressed from 2 micron (high-copy) plasmids could a reproducible signal be observed.

Figure 57:
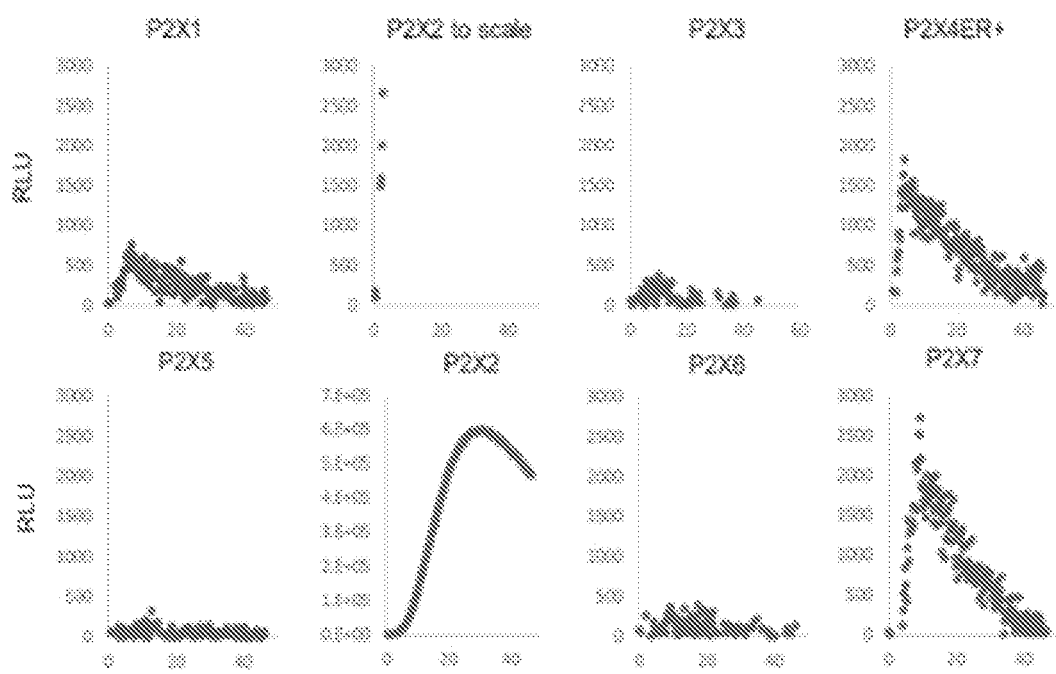

FIG. 57 shows functional assays of all P2X subtypes in yeast. Aequorin assay of all P2X receptor subtypes. P2X4ER+ is the truncated (ΔC14) receptor with the addition of an ER export signal (FCYENEV) to the carboxy terminus. All other receptors are wild-type sequences. Reproducible signals were observed in subtypes 1, 2, 4, and 7.

FIG. 58A-B shows P2X2 dose-response with ATP. A, time course of ATP-dependent luminescence of P2X2. Each curve represents a different ATP concentration. B, area under the curve from the luminescence assay was plotted against concentration and fit.

FIG. 59A-B shows P2X2 does-response with 2-Cl-ATP. A, time course of 2-Cl-ATP-dependent luminescence of P2X2. Each curve represents a different 2-Cl-ATP concentration. B, area under the curve from the luminescence assay was plotted against concentration and fit.

FIG. 60A-B shows P2X2 dose-response with BzATP. A, time course of BzATP-dependent luminescence of P2X2. Each curve represents a different BzATP concentration. B, area under the curve from the luminescence assay was plotted against concentration and fit.

FIG. 61A-B shows P2X2 is inhibited by suramin. A, luminescence of ATP-induced signaling. B, inhibition curve generated from timecourse data.

FIG. 62 shows nonfunctional P2X2 mutant does not gate wtP2X2 response is depicted in gray. Orange represents the response of the broken receptor (K81C, K83C). No response is observed in the double mutant.

Figure 63:
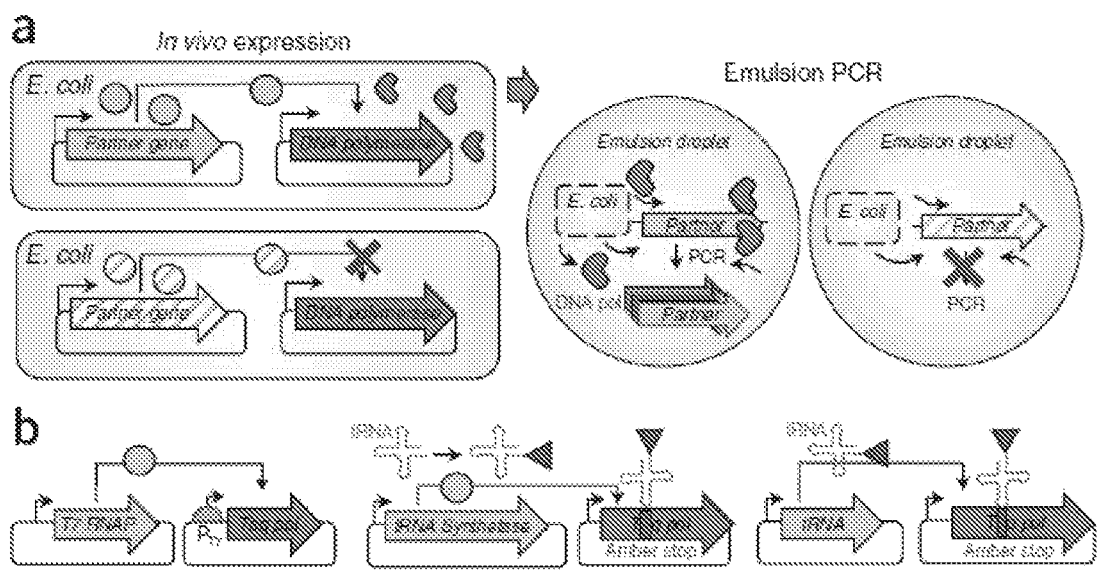

FIG. 63A-B shows the general CPR concept. (A) Schematic of CPR principle. A gene circuit is generated in which a partner-gene activity allows the expression of a DNA polymerase in bacterial cells. Inactive gene variants lead to no expression of the DNA polymerase. The genetic circuit containing the diversified partner-gene pool is expressed in vivo, allowing DNA polymerase production only in cells with active partner-gene variants. The live cells are subsequently emulsified to produce no more than a single cell per emulsion droplet. The initial boiling step of the ePCR lyses the cells, releasing the produced DNA polymerase protein as well as the partner-gene-encoding plasmid into the aqueous solution of the emulsion droplet. Ensuing thermal cycling amplifies only the active partner-gene variant, which is recovered and used in the next round of CPR selection. (B) Examples of genetic circuits for CPR. Partner-gene function can be linked to expression of a DNA polymerase in a number of ways, as is demonstrated by the example of T7 RNAP, pol, polymerase; tRNA synthetase, and tRNA engineering.

Figure 64:
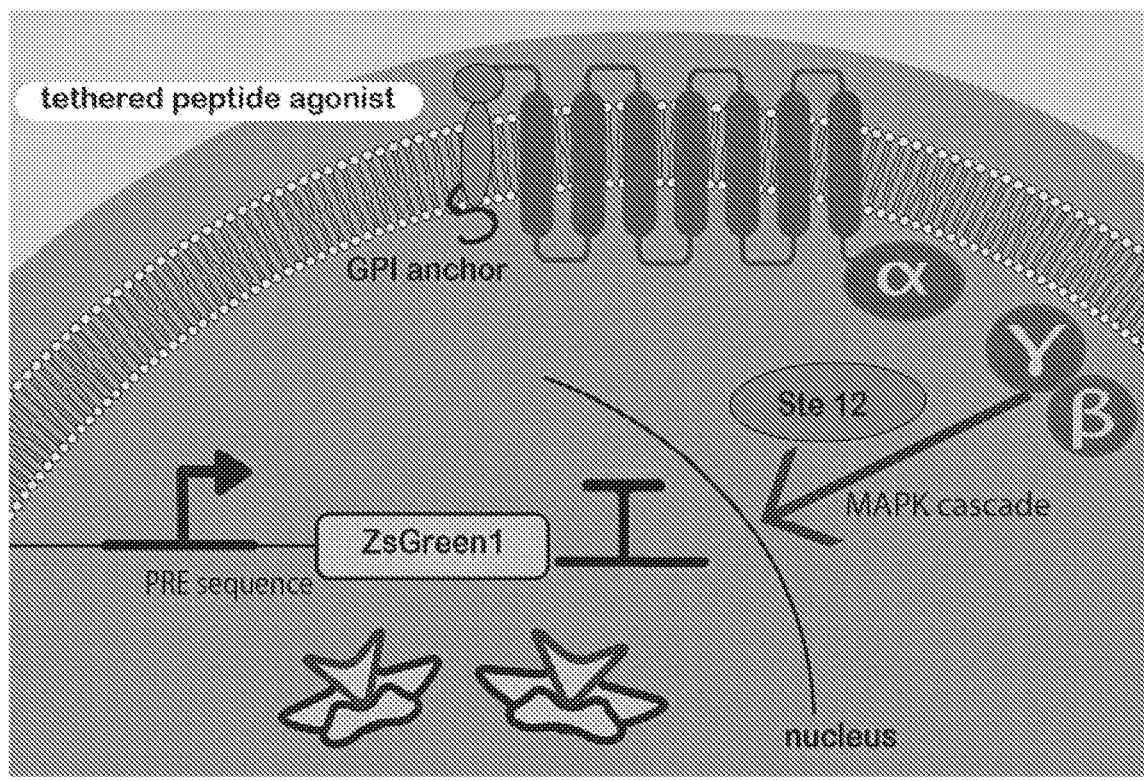

FIG. 64 shows a tethered peptide agonist using zSGreen1.

Figure 65:
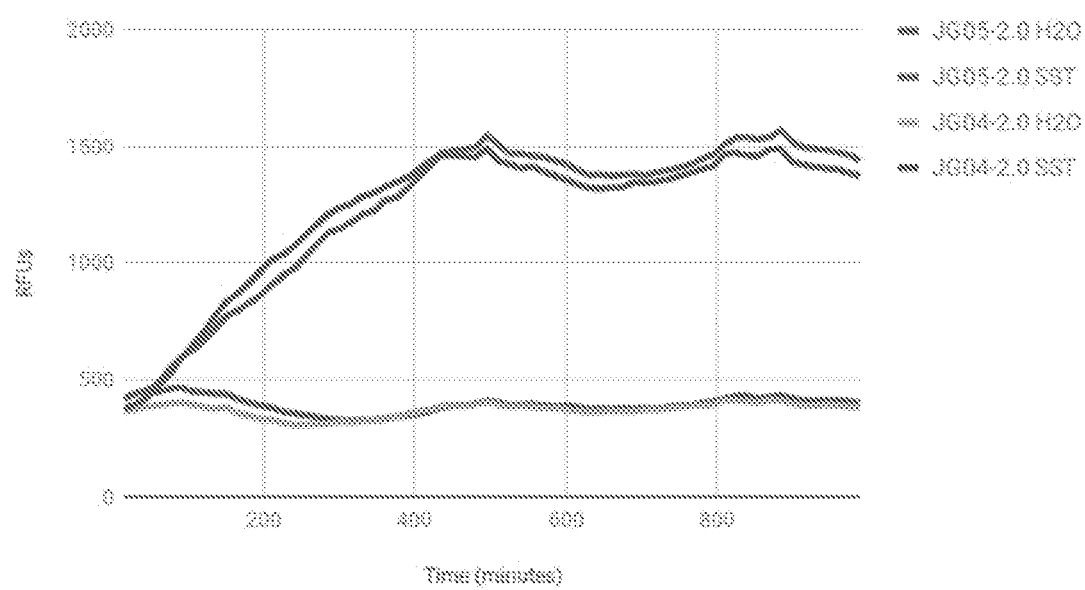

FIG. 65 shows the SSTR with an exogenous ligand 10 uM somatostatin was added to appropriate wells. Equal amounts of water were added to control wells. 18 hour kinetic time course was used on the plate reader, fluorescent signal corrected by OD600.

Figure 66A:
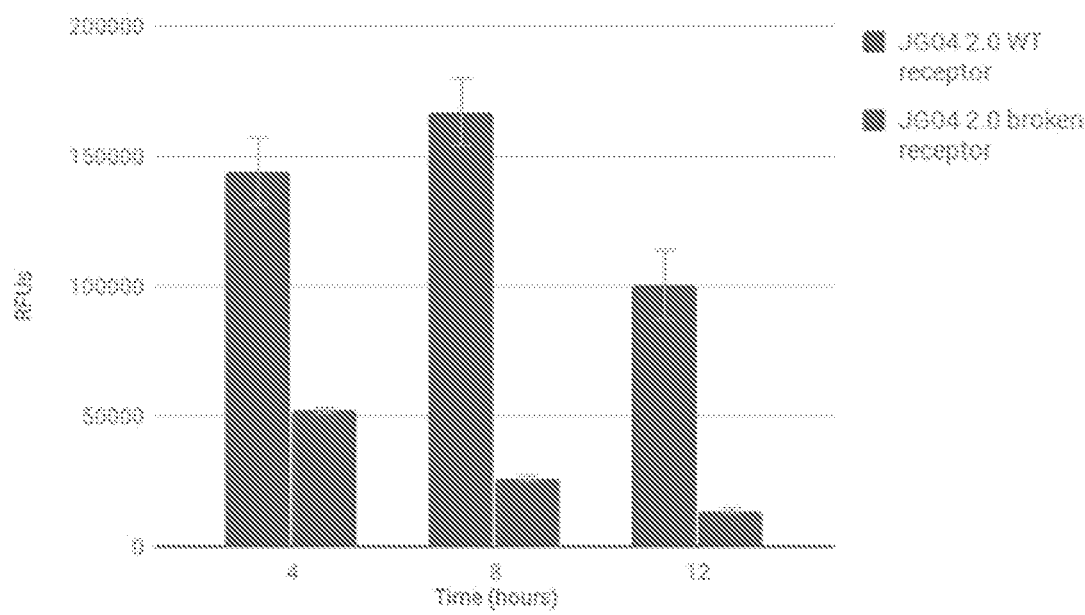
Figure 66B:
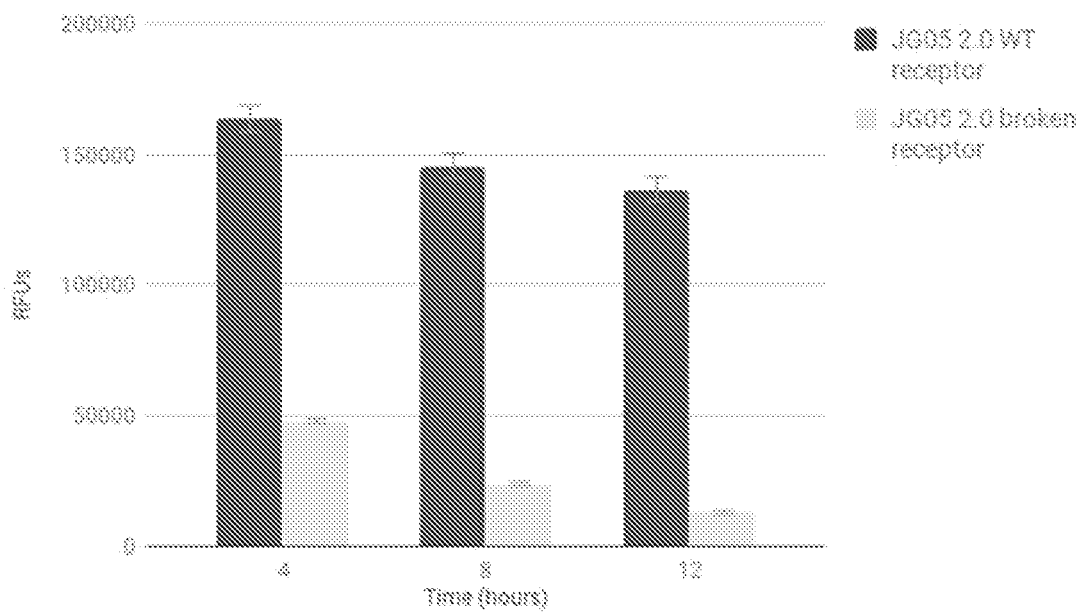

FIG. 66A-B shows SSTR autoactivation. (A) JG04 strain; (B) JG05 strain.

Figure 67:
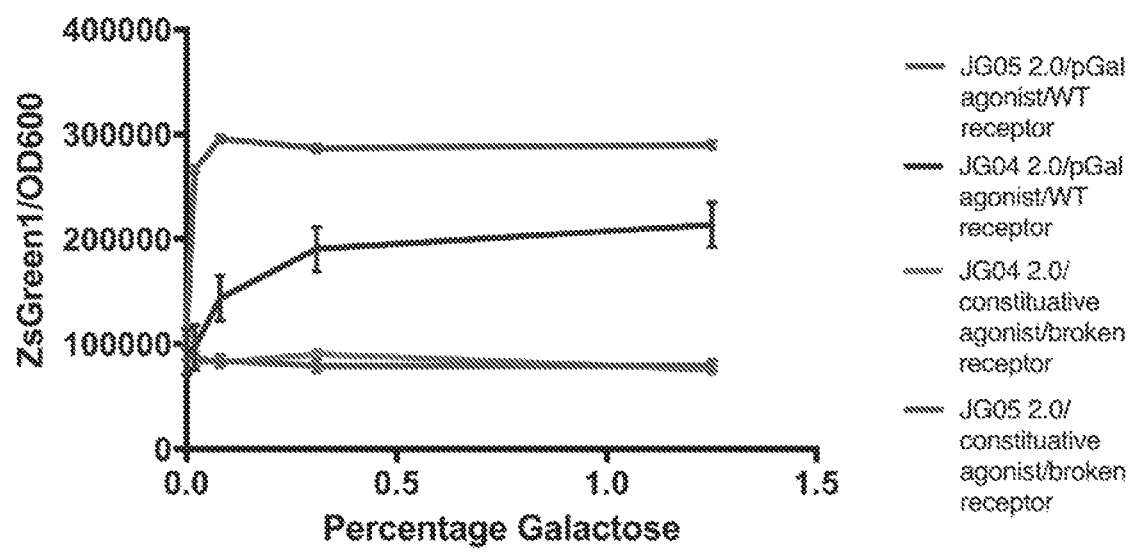

FIG. 67 shows galactose induction at the 18 hour endpoint.

Figure 68:
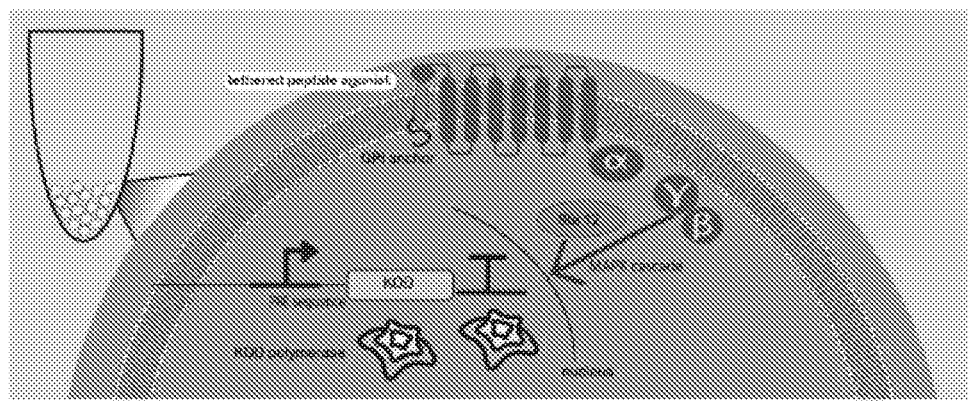

FIG. 68 shows a tethered peptide agonist using KOD.

Figure 69:
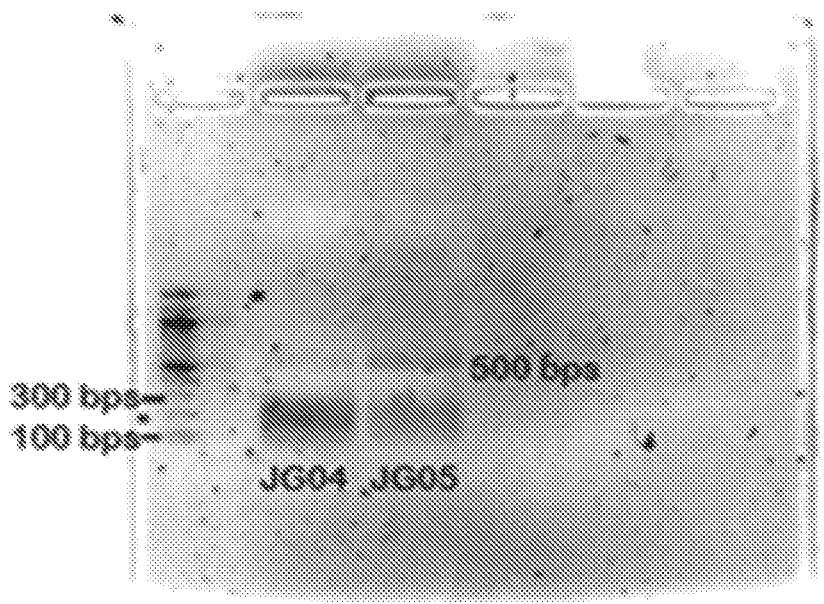

FIG. 69 shows yCPR mock selections.

Figure 70:
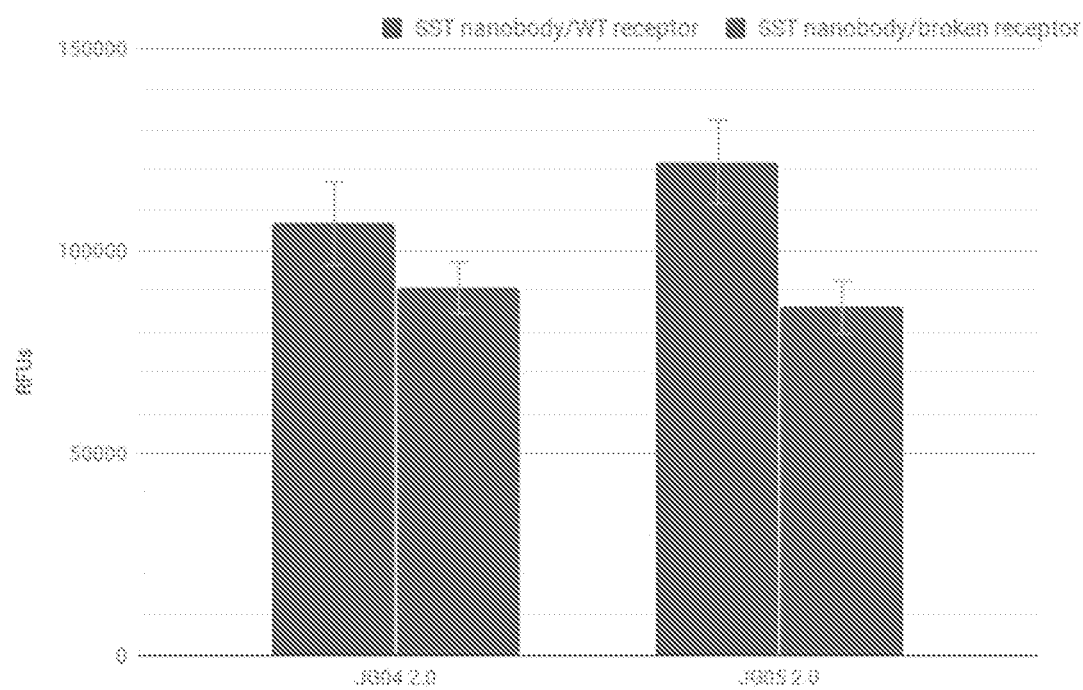

FIG. 70 shows nanobody auto-activation at 8 hours for SST nanobody.

Figure 71A:
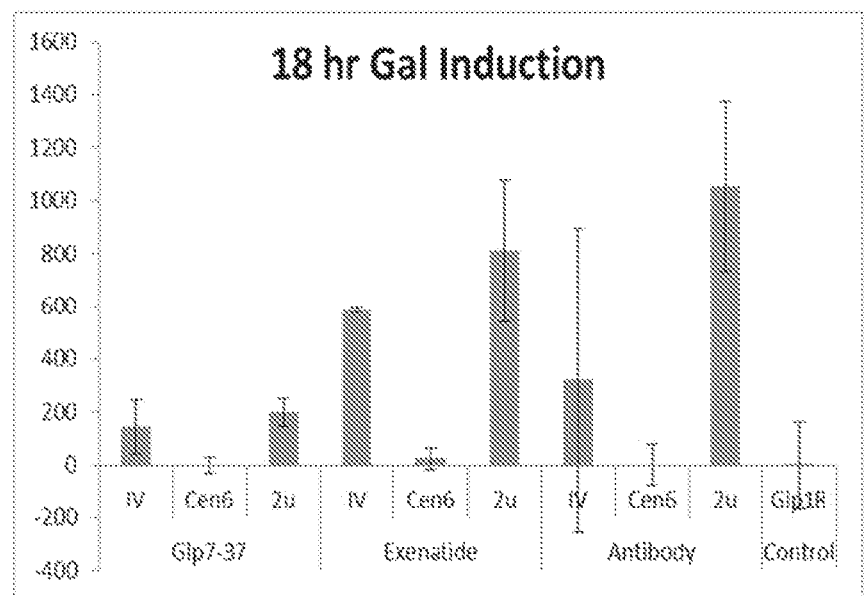
Figure 71B:
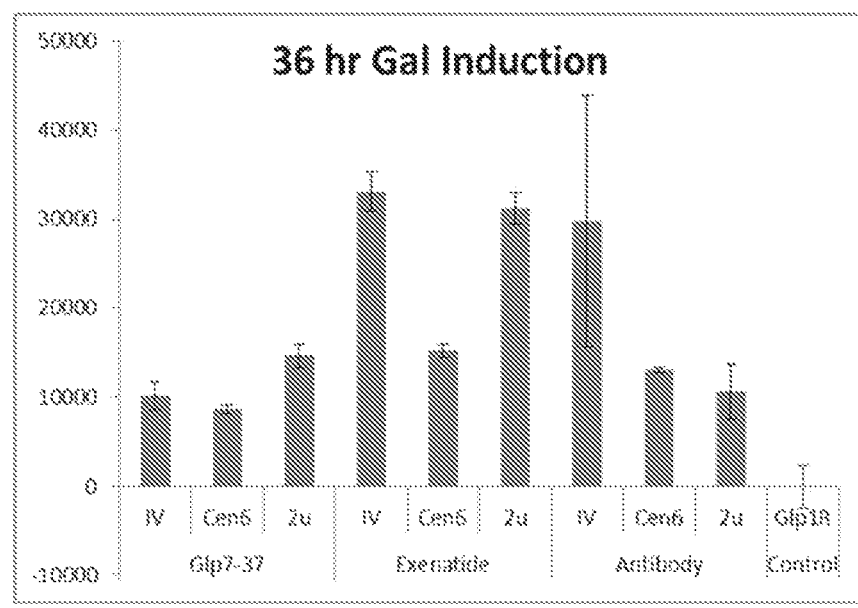

FIG. 71A-B shows autoinduction of human Glp1R (GPCR) with tethered peptides and human antibody. (A) is 18 hours with Gal induction, (B) is 36 hours with Gal induction.

DETAILED DESCRIPTION

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid the reader in distinguishing the various components, features, or steps of the disclosed subject matter. The identifiers "first" and "second" are not intended to imply any particular order, amount, preference, or importance to the components or steps modified by these terms.

By convention, polynucleotides that are formed by 3'-5' phosphodiester linkages (including naturally occurring polynucleotides) are said to have 5'-ends and 3'-ends because the nucleotide monomers that are incorporated into the polymer are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule generally has a free phosphate group at the 5' position of the pentose ring of the nucleotide, while the 3' end of the polynucleotide molecule has a free hydroxyl group at the 3' position of the pentose ring. Within a polynucleotide molecule, a position that is oriented 5' relative to another position is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

As used herein, it is not intended that the term "polynucleotide" be limited to naturally occurring polynucleotide structures, naturally occurring nucleotides sequences, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention.

As used herein, the expressions "nucleotide sequence," "sequence of a polynucleotide," "nucleic acid sequence," "polynucleotide sequence", and equivalent or similar phrases refer to the order of nucleotide monomers in the nucleotide polymer. By convention, a nucleotide sequence is typically written in the 5' to 3' direction. Unless otherwise indicated, a particular polynucleotide sequence of the invention optionally encompasses complementary sequences, in addition to the sequence explicitly indicated.

As used herein, the term "gene" generally refers to a combination of polynucleotide elements, that when operatively linked in either a native or recombinant manner, provide some product or function. The term "gene" is to be interpreted broadly, and can encompass mRNA, cDNA, cRNA and genomic DNA forms of a gene. In some uses, the term "gene" encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some aspects, genes do not encode a polypeptide, for example, ribosomal RNA genes (rRNA) and transfer RNA (tRNA) genes. In some aspects, the term "gene" includes not only the transcribed sequences, but in addition, also includes non-transcribed regions including upstream and downstream regulatory regions, enhancers and promoters. The term "gene" encompasses mRNA, cDNA and genomic forms of a gene.

In some aspects, the genomic form or genomic clone of a gene includes the sequences of the transcribed mRNA, as well as other non-transcribed sequences which lie outside of the transcript. The regulatory regions which lie outside the mRNA transcription unit are termed 5' or 3' flanking sequences. A functional genomic form of a gene typically contains regulatory elements necessary, and sometimes sufficient, for the regulation of transcription.

The term "promoter" is generally used to describe a DNA region, typically but not exclusively 5' of the site of transcription initiation, sufficient to confer accurate transcription initiation. In some aspects, a "promoter" also includes other cis-acting regulatory elements that are necessary for strong or elevated levels of transcription, or confer inducible transcription. In some embodiments, a promoter is constitutively active, while in alternative embodiments, the promoter is conditionally active (e.g., where transcription is initiated only under certain physiological conditions).

Generally, the term "regulatory element" refers to any cis-acting genetic element that controls some aspect of the expression of nucleic acid sequences. In some uses, the term "promoter" comprises essentially the minimal sequences required to initiate transcription. In some uses, the term "promoter" includes the sequences to start transcription, and in addition, also include sequences that can upregulate or downregulate transcription, commonly termed "enhancer elements" and "repressor elements," respectively.

Specific DNA regulatory elements, including promoters and enhancers, generally only function within a class of organisms. For example, regulatory elements from the bacterial genome generally do not function in eukaryotic organisms. However, regulatory elements from more closely related organisms frequently show cross functionality. For example, DNA regulatory elements from a particular mammalian organism, such as human, will most often function in other mammalian species, such as mouse. Furthermore, in designing recombinant genes that will function across many species, there are consensus sequences for many types of regulatory elements that are known to function across species, e.g., in all mammalian cells, including mouse host cells and human host cells.

As used herein, the expressions "in operable combination," "in operable order," "operatively linked," "operatively joined" and similar phrases, when used in reference to nucleic acids, refer to the operational linkage of nucleic acid sequences placed in functional relationships with each other. For example, an operatively linked promoter, enhancer elements, open reading frame, 5' and 3' UTR, and terminator sequences result in the accurate production of an RNA molecule. In some aspects, operatively linked nucleic acid elements result in the transcription of an open reading frame and ultimately the production of a polypeptide (i.e., expression of the open reading frame).

As used herein, the terms "vector," "vehicle," "construct" and "plasmid" are used in reference to any recombinant polynucleotide molecule that can be propagated and used to transfer nucleic acid segment(s) from one organism to another. Vectors generally comprise parts which mediate vector propagation and manipulation (e.g., one or more origin of replication, genes imparting drug or antibiotic resistance, a multiple cloning site, operably linked promoter/enhancer elements which enable the expression of a cloned gene, etc.). Vectors are generally recombinant nucleic acid molecules, often derived from bacteriophages, or plant or animal viruses. Plasmids and cosmids refer to two such recombinant vectors. A "cloning vector" or "shuttle vector" or "subcloning vector" contain operably linked parts that facilitate subcloning steps (e.g., a multiple cloning site containing multiple restriction endonuclease target sequences). A nucleic acid vector can be a linear molecule, or in circular form, depending on type of vector or type of application. Some circular nucleic acid vectors can be intentionally linearized prior to delivery into a cell.

As used herein, the term "expression vector" refers to a recombinant vector comprising operably linked polynucleotide elements that facilitate and optimize expression of a desired gene (e.g., a gene that encodes a protein) in a particular host organism (e.g., a bacterial expression vector or mammalian expression vector). Polynucleotide sequences that facilitate gene expression can include, for example, promoters, enhancers, transcription termination sequences, and ribosome binding sites.

As used herein, the term "host cell" refers to any cell that contains a heterologous nucleic acid. The heterologous nucleic acid can be a vector, such as a shuttle vector or an expression vector. In some aspects, the host cell is able to drive the expression of genes that are encoded on the vector. In some aspects, the host cell supports the replication and propagation of the vector. Host cells can be bacterial cells such as *E. coli*, or mammalian cells (e.g., human cells or mouse cells). When a suitable host cell (such as a suitable mouse cell) is used to create a stably integrated cell line, that cell line can be used to create a complete transgenic organism.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "transformation" and "transfection" mean the introduction of a nucleic acid, e.g., an expression vector, into a recipient cell including introduction of a nucleic acid to the chromosomal DNA of said cell.

By "isolated nucleic acid" or "purified nucleic acid" is meant DNA that is isolated from the naturally-occurring genome of the organism from which the DNA of the invention is derived. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules. The term "start of replication" is intended to mean a nucleotide sequence at, which DNA synthesis for replication of the vector begins. Start of replication may occur at one or more points within the vector dependent on the vector being used, such as at one point in a plasmid vector or at several points in an adeno-vector. The start of replication is generally termed origin of replication (abbreviated ori site) in a plasmid vector.

The term "control sequence" or "control sequences" is intended to mean nucleotide sequences involved in control of a response of action. This includes nucleotide sequences and/or proteins involved in regulating, controlling or affecting the expression of structural genes, or the replication, selection or maintenance of a plasmid or a viral vector. Examples include attenuators, silencers, enhancers, operators, terminators and promoters.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene)). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

The term "recombinant microorganism" or "genetically modified microorganism", as used herein, refers to a microorganism genetically modified or genetically engineered. It means, according to the usual meaning of these terms, that the microorganism of the invention is not found in nature and is modified either by introduction, by deletion or by modification of genetic elements. The term "recombinant element" refers to a genetic sequence which is not native to the host into which it is inserted.

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganisms with exogenous DNA is a routine task for those skilled in the art.

As used herein, the terms "heterologous" or "exogenous" as applied to polynucleotides or polypeptides refers to molecules that have been rearranged or artificially supplied to a biological system and are not in a native configuration (e.g., with respect to sequence, genomic position or arrangement of parts) or are not native to that particular biological system. These terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

As used herein, the terms "native" or "endogenous" refer to molecules that are found in a naturally occurring biological system, cell, tissue, species or chromosome under study. A "native" or "endogenous" gene is a generally a gene that does not include nucleotide sequences other than nucleotide sequences with which it is normally associated in nature (e.g., a nuclear chromosome, mitochondrial chromosome or chloroplast chromosome). An endogenous gene, transcript or polypeptide is encoded by its natural locus, and is not artificially supplied to the cell.

The nucleic acids disclosed herein may have sequences that vary from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like.

The phrase "functionally equivalent variants" should also be taken to include nucleic acids whose sequence varies as a result of codon optimization for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

The polypeptides disclosed herein may have sequences that vary from the sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from I to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria.

"Substantially the same function" as used herein is intended to mean that the nucleic acid or polypeptide is able to perform the function of the nucleic acid or polypeptide of which it is a variant. One may assess whether a functionally equivalent variant has substantially the same function as the nucleic acid or polypeptide of which it is a variant using any number of known methods.

"Over-express", "over expression" and like terms and phrases when used in relation to the invention should be taken broadly to include any increase in expression of one or more protein as compared to the expression level of the protein of a parental microorganism under the same conditions. It should not be taken to mean that the protein is expressed at any particular level.

An "appropriate culture medium" designates a medium (e.g., a sterile, liquid media) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

General Description

Disclosed herein is a method of receptor Compartmentalized Partnered Replication (rCPR). In CPR, a thermostable polymerase gene is linked in the context of a genetic circuit to the function of a partner gene or genes, and libraries of the partner gene are emulsified in water-in-oil mixtures. The general scheme of CPR can be seen in FIG. 6). Those partner variants that yield production of the thermostable polymerase can be selectively amplified upon thermal cycling in the emulsion. This directed evolution method has previously been applied to altering enzymatic activities in polymerases, repressors, and enzymes involved in the translation apparatus (Ellefson 2014; Meyer 2015: Abil 2017).

In the case of rCPR, the method includes determining an association of a signal transduction pathway or receptor and an effector molecule of the signal transduction pathway or receptor, the method comprising: a) providing a recombinant molecule encoding a signal transduction pathway or receptor coupled to a polymerase; b) exposing the recombinant molecule to a library of organisms and primers, wherein said primers can amplify potential effector molecules of the signal transduction pathway or receptor; c) detecting interaction between the signal transduction pathway or receptor and an effector molecule.

For example, the recombinant molecule can be introduced to a cell, where the recombinant molecule can be transcribed under proper conditions that allow for production of the polymerase. These conditions can be ones that bring about the interaction of an effector molecule with a receptor or with a pathway, such that polymerase is produced in the process. In one example, the cells in which the recombinant molecules have been inserted can then be singled out in an oil-in emulsion process and exposed to conditions that can allow for the polymerase to amplify a product. These conditions can include the supplying of dNTPs and primers, for example. One of skill in the art will appreciate the other conditions that can be provided that can lead to amplification by the polymerase encoded by the recombinant molecule.

The method disclosed above can take place in a number of culturable cell types. Suitable host cells for cloning or expressing the recombinant molecule in the vectors herein are the prokaryote, yeast, or higher eukaryote cells described above. For instance, the cell can be bacterial, such as an *E. coli* cell. Alternatively, the cell can be a eukaryotic cell, such as a yeast, plant, insect, or mammalian cells.

The polymerase used with the disclosed method can be any type of polymerase. Examples include, but are not limited to, naturally-occurring polymerase isolated from any species of the genus *Thermus*, any species of the genus *Meiothermus*, any species of the genus *Thermotoga*, and/or any species of the genus *Thermomicrobium*. In some embodiments, the naturally-occurring polymerase is isolated from *Bacillus stearothermophilus, Sphaerobacter thermophilus, Dictoglomus thermophilum*, and/or *Escherichia coli*. In some embodiments, the naturally-occurring polymerase is isolated from *Thermus aquaticus, Thermus thermophilus, Thermus caldophilus*, or *Thermus filiformis*. In some embodiments, the naturally-occurring polymerase is isolated from *Thermus aquaticus*.

Also disclosed herein are archaeal DNA polymerases. As used herein, "archaeal" DNA polymerase refers to DNA polymerases that belong to either the Family B/pol I-type group (e.g., Pfu, KOD, Pfx, Vent, Deep Vent, Tgo, Pwo) or the pol II group (e.g., *Pyrococcus furiosus* DP1/DP2 2-subunit DNA polymerase). In one embodiment, "archaeal" DNA polymerase refers to thermostable archaeal DNA polymerases (PCR-able) and include, but are not limited to, DNA polymerases isolated from *Pyrococcus* species (*furiosus*, species GB-D, *woesii, abysii, horikoshii*), *Thermococcus* species (*kodakaraensis* KOD1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995.

Also disclosed are modified polymerases, or variants of naturally occurring polymerases that retain polymerase function but comprise an enhanced feature.

The polymerase used can be an RNA polymerase. Examples include, but are not limited to, RNA pol I, RNA pol II, and RNA pol III. Also disclosed are variants and modified versions of these naturally occurring RNA polymerases.

In the methods disclosed herein, the polymerase of the recombinant molecule can be coupled with bar-coding. Bar-coding is known to those in the art and can be used by providing a unique "tag" comprising a nucleic acid molecule in conjunction with a receptor or pathway. This unique barcode can be coupled to the receptor or effector such that the library member can be identified by counting barcodes in next-generation sequencing analysis. For example, each library member is uniquely tagged and those library members that lead to the most production of polymerase create more copies of their unique barcodes. Once pooled, these barcodes can then be counted.

The methods disclosed herein involve a receptor, signal transduction pathway, or metabolic pathway. These can be naturally occurring or can be modified or engineered. For example, one can create a library of potential receptors in order to determine which one will best interact with an effector molecule, such as a small molecule. This method can be used to select a receptor/effector pair that interacts in a desirable way. Barcoding can be used to later identify a desired receptor. For example, the receptor can be an orthogonal receptor. Examples of orthogonal receptor design are known to those of skill in the art.

The methods disclosed herein can be used for selection of a compound produced by a metabolic pathway that activates the receptor or signal transduction pathway. Therefore, the methods disclosed herein can be used to determine a compound that interacts successfully with a given receptor or pathway. Therefore, the disclosed methods and platforms are unique in that they can be used in the co-identification of metabolic pathways and receptors that functionally interact.

The methods disclosed herein can be used to directly detect RNA. This method comprises the use of an RNA polymerase In the above mentioned examples, the target molecule is DNA. However, it is often useful to target RNA. In this instantiation, this method can utilize RNASeq to identify library member variants.

The effector molecule disclosed herein can be an agonist or an antagonist. An example of this is the detection of a peptide or an antibody that can activate the production of the polymerase. To detect an antagonist, an inverter circuit can be used. In the case of an inverter circuit, a repressor is activated during circuit antagonism. This repressor may or may not be fused to a degradation tag. If a library member is able inactivate the receptor or antagonize it, then the repressor will not be expressed. An inducible reporter polymerase is then expressed with operator sequences to the repressor. In the absence of repressor, the polymerase is expressed, and the library members or barcodes are amplified.

Also disclosed herein is a platform comprising a recombinant molecule, wherein said recombinant molecule encodes a signal transduction pathway or receptor coupled to a polymerase, and a library of organisms and primers, wherein said primers are designed to amplify potential effector molecules of the signal transduction pathway or receptor.

In a specific example of the usefulness of the methods disclosed herein, disclosed are molecules referred to herein as HAVOCs. One of the most daunting problems for producing and introducing new DREADDs is the painstaking identification of compounds that will be truly specific, and not otherwise impact the extensive set of neural receptors and interactions in the brain. While to date this has relied on identifying the very few compounds that can cross the BBB and fit in the pocket of a slightly altered neural GPCR, disclosed herein is an alternative strategy that paves the way to many more orthogonal effectors. Disclosed are receptors with such extremely high affinities for their effectors that the use of a known effector 'flies below the radar' of the rest of the brain. This allows for one to not rely solely on designer drugs, but rather to use very small amounts of natural compounds whose biodistribution properties are already known. These new orthogonal receptor:effector pairs are referred to herein as High Affinity, Validated Orthogonality Couples (HAVOCs), thus extending DREADDs to HAVOCs. In essence, receptors are developed where micro- or nano-dosing of compounds leads to orthogonality and can be used to probe neural function. The availability of such receptors in turn leads to the development of animal models where multiple neural 'dials' can be manipulated in parallel to more finely tune brain function.

The receptor CPR methods disclosed herein can be useful in at least four ways: (a) It can be used for high-throughput screening of receptors, in that production of a thermostable polymerase can be coupled with bar-coding to use sequencing to quickly identify which receptor in a library was activated by a given compound. This can allow convenient mining for the receptor specificity of a drug, and concomitant screening of off-target drug effects. (b) It can be used to evolve receptors to be responsive to orthogonal ligands, creating HAVOCs. Beyond these initial demonstrations, rCPR can also be (c) used for the selection of metabolic pathways or metabolic pathway variants that produce a compound that activates a particular receptor or signal transduction pathway, (d) used for the co-identification of metabolic pathways and receptors that functionally interact. In other words, rCPR becomes the first functional selection method that co-identifies drugs and targets.

Disclosed herein is a general method for the directed evolution of HAVOCs. For example is the CB2 receptor, which not typically expressed in neural cells, and thus provides an additional level of orthogonality relative to the current set of receptors. The agonist β-caryophyllene is used to develop CPR methods and produce the first HAVOC, and then other cannabinoids are identified, and a raft of corresponding high affinity, orthogonal receptors follows. The effector and receptor are produced using the same cells, rather than add the effector to cells, although either is possible. This is to avoid loss of compound during spheroplasting, as many hydrophobic compounds can seep into the oil layer and be unavailable to the receptor. It also has the great advantage of allowing for quick reconfiguration of genetic circuits for new HAVOCs, rather than having to rely on whatever compounds may (or may not) be commercially or synthetically available. This method also greatly saves on the expense of adding an often expensive effector to large volumes of culture media.

The methods disclosed herein can be used in drug discovery, receptor/pathway modification (orthogonal receptors, for example) and in methods of treating various diseases and disorders.

EXAMPLES

Example 1: Receptor Compartmentalized Partnered Replication (rCPR)

β-caryophyllene was chosen as a starting point because of its known utility in neurobiology, such as producing therapeutic effects that mitigate inflammation (Iwamura 2001) and its analgesic properties (Ibrahim 2005). β-caryophyllene binds specifically to the cannabinoid receptor CB2 and does not activate the related CB1 nor the 5HT1A receptors, and thus is already partially orthogonal. Moreover, CB2 is not expressed in the brain, and thus by choosing this receptor orthogonal pathways can be crafted that can be further integrated into neural and animal models. In order to develop a CPR-based system for converting β-caryophyllene into a HAVOC, the functional expression of CB2 was developed in yeast to the biosynthesis of β-caryophyllene, and this coupling is used to proof CPR for receptors and ultimately evolve variants of CB2 that are activated by extremely low concentrations of β-caryophyllene.

Figure 1:
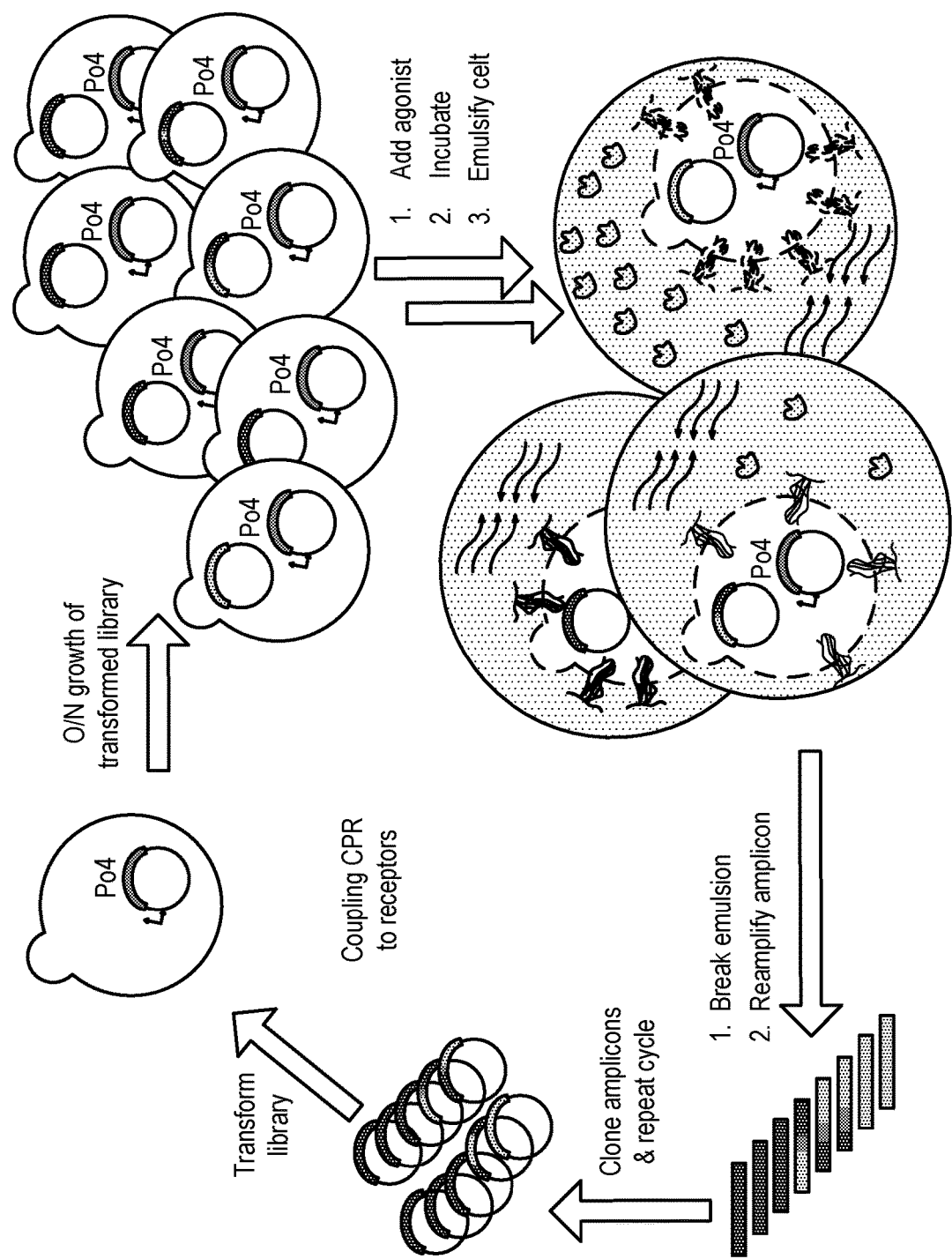
FIG. 1 shows a schematic of receptor Compartmentalized Partnered Replication (rCPR). GPCRs are constitutively express in yeast. During the in vivo phase, agonists/antagonists are incubated with cells. Upon circuit activation, cells are washed and isolated from each other in water in oil emulsion bubbles. Primers for a target of interest are used to selectively amplify receptors/pathway that allowed for the production of KOD polymerase.
Figure 2:
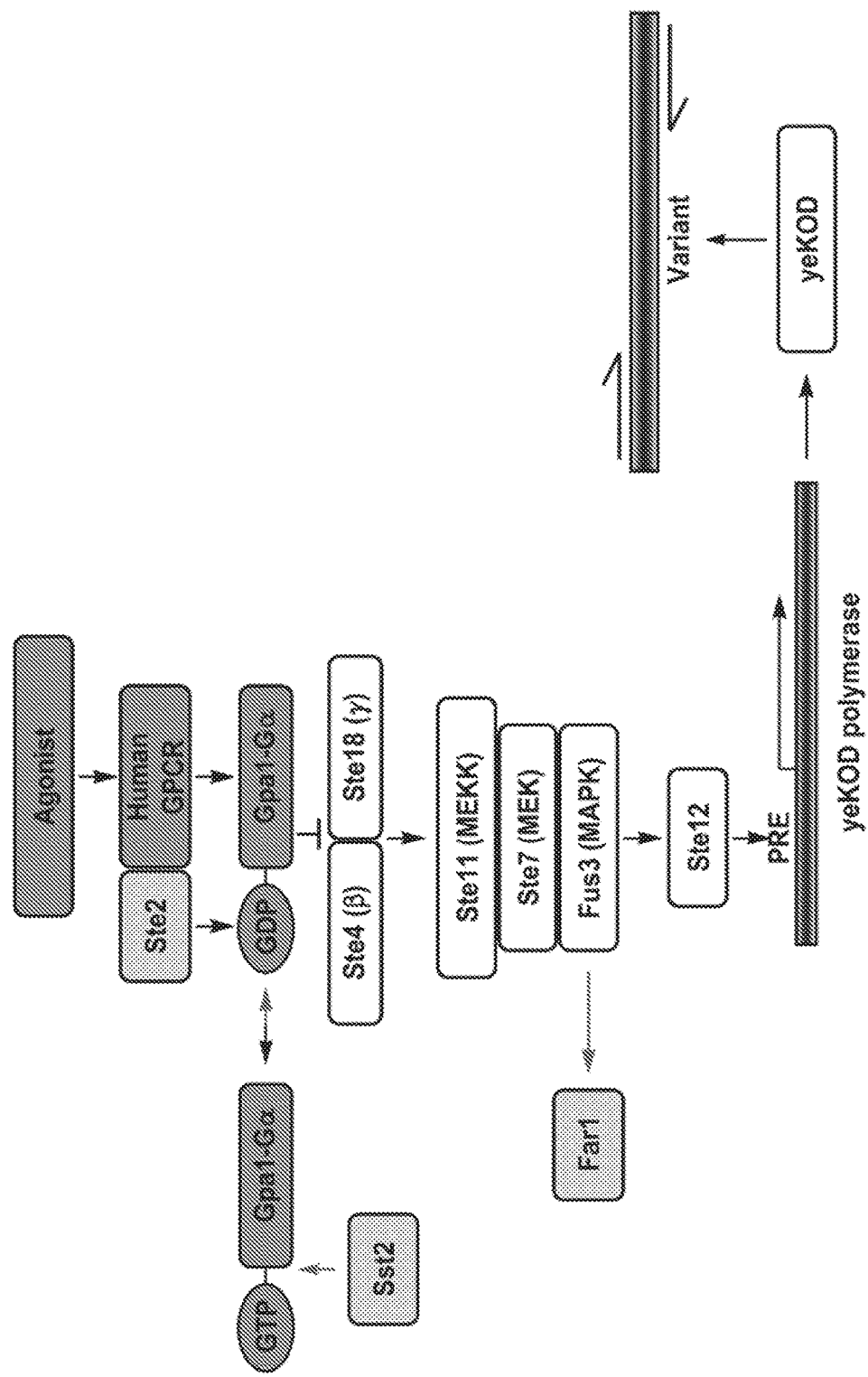
FIG. 2 shows an overview of the GPCR pathway. Human GPCRs are expressed in yeast. Signaling is hijacked by a series of knockouts (grayed out) and replacement of Fus1 with KOD polymerase. After activation of the circuit, KOD is produced which is then used in emulsion PCR.

To couple signal transduction to the expression of the thermostable polymerase KOD for CPR, a human GPCR is implanted in yeast, and its function is coupled to the pheromone response pathway, as has been previously described (Dong 2010). A codon-optimized version of CB2 was introduced into the yeast chromosome under the control of the inducible pGal1 promoter on a 2 micron high-copy plasmid. In parallel, CRISPR-Cas9 was used to delete the endogenous pheromone receptor GPCR (Ste2), as well as the Sst2 and Far1 genes, which further insulates the signaling pathway from cross-talk and ensures orthogonality. A knock-in of a yeast-human chimeric G-alpha protein (Gpa1) was then generated, in which the last 5 C-terminal amino acids are from human G-alpha proteins, but the remaining N terminus was from the yeast Gpa1 G-alpha gene, and thus could communicate effectively with downstream signal transduction machinery and ultimately up-regulate the pheromone response element (PRE; FIG. 2) (Hagen 1991, Brown 2000). The GFP gene was initially cloned downstream of the PRE (in place of Fus1) to test for CB2 responsiveness. The overall pathway showed dose-dependent up-regulation of GFP expression in response to exogenously added β-caryophyllene (FIG. 3B).

While CPR could be carried out by exogenously adding β-caryophyllene, it would prove difficult to control the concentration in the context of an emulsion, and instead it was desired to produce this compound in the yeast itself, leading to a system in which both effector production and receptor activation could occur simultaneously. To produce β-caryophyllene in yeast, the native isoprenoid pathway for the production of farnesyl diphosphate (FPP) was augmented by the heterologous expression of QHS1 β-caryophyllene synthase from *Artemisia annua*. This resulted in the production of small amounts of β-caryophyllene, as determined by mass-spectrometry. To maximize yields, the UCP2-1 transcription factor was inserted to upregulate expression of enzymes HMG-CoA synthase (ERG13), mevalonate kinase (ERG12), and phosphomevalonate kinase (ERG8). In addition, extra copies of the enzymes isopentenyl diphosphate isomerase (IDI1), truncated HMG-CoA reductase (t-HMG-1), and farnesyl diphosphate synthase (ERG20) were inserted into the genome.

Figure 3A:
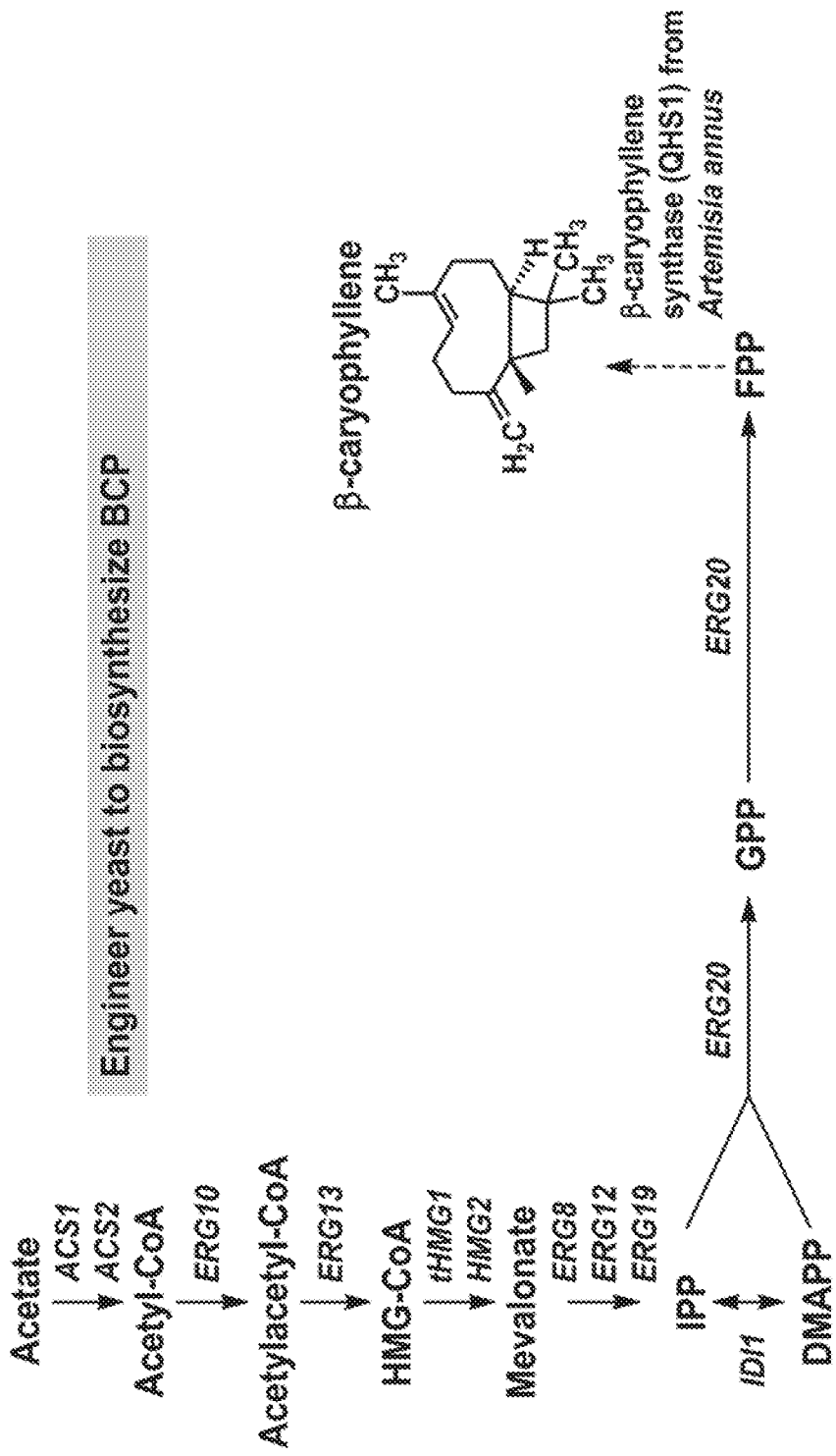

When the augmented β-caryophyllene biosynthetic pathway was expressed in a CB2 sensor strain (FIG. 2) with GFP expressed from the pheromone response element promoter (PRE), autodetection of β-caryophyllene compound was observed (FIG. 3). The same yeast had both produced a neural effector and sensed it.

To show that CPR can be carried out with receptors such as with CB2, a pathway is generated in which KOD polymerase is under the control of the PRE, and a "mock selection" is created in which a wild-type CB2 and a broken synthase containing a premature stop codon compete with one another at different ratios. The recovered amplicons from the fully functional and broken receptors are compared to determine the enrichment factor (wild-type divided by broken receptor signal strength). Upon spheroplasting, emulsification, and thermal cycling, the wild-type, is selected, a functional CB2, with at least a 1,000-fold selection coefficient. Upon determining the enrichment factor experimental parameters can be modulated to optimize the range of detection sensitivity. For example, changing the concentration of ligand, expressing the receptor on different copy-number vectors, changing the duration of ligand exposure, and changing the number of cycles of the emulsion PCR step can all be done to fine-tune results.

Similar mock negative selections is carried out by engineering a so-called inverter circuit in which β-caryophyllene drive not KOD polymerase expression, but rather the expression of the lambda repressor. This repressor blocks KOD expression from a suitably engineered Gal promoter. Thus, functional receptors inhibit, rather than activate polymerase production, and are lost during CPR. This negative selection circuit thereby avoids the selection of constitutively active receptors, and can be useful for refining the specificity of receptor variants for a particular compound. Negative selections can be introduced that have at least 1,000-fold selection coefficients.

Having proofed CPR with endogenously produced β-caryophyllene and CB2, CB2 libraries are generated to select for receptors with much higher affinities. CB2 libraries are homologously recombined into the yeast genome at the Ura3 locus, and library complexity are characterized by NextGen sequencing. Those residues in the known binding pocket are targeted via synthesis of gene libraries, and in later rounds of selection mutagenic PCR can be used to obtain additional, functional mutations throughout the protein. One of the advantages of using CPR-based selection methods is that libraries of receptor variants can be screened that contain upwards of $10^8$ members, orders of magnitude larger than previous screens with fluorescent proteins or other reporters. Upwards of 6 residues can therefore be randomized in the binding pocket of CB2 simultaneously without loss of coverage ($20^6 < 10_8$).

To tune the level of β-caryophyllene expression, the production of β-caryophyllene synthase is put under the control of a medium-strength promoter (pRPL18B; (Lee 2015)) that is in turn controlled by the tetracycline repressor (the Tet-OFF configuration; (Tanaka 2015)). Addition of increasing amounts of tetracycline to yeast prior to emulsification allows for tuning the expression of the pathway downwards, and thereby to modulate the amount of β-caryophyllene 'seen' by CB2 during the selection. The activation of CB2 can be a composite of compound production both pre- and post-emulsification, and HPLC can be used to monitor the accumulation of β-caryophyllene in culture media. Multiple cycles of positive and negative selection and amplification of the mutant library under increasingly stringent conditions can yield CB2 variants that are responsive to extremely small concentrations of β-caryophyllene. As the selection proceeds, the library is sequenced for convergence, and those variants that are most populous are cloned for additional characterizations. Synthetic variants that contain consensus mutations can also be constructed based on sequencing.

Initial characterizations of the evolved variant CB2 receptors are carried out in yeast, based on the artificial signaling pathways that we have developed. Different concentrations of β-caryophyllene is introduced into yeast expressing variant CB2 receptors, and the activity of the receptors is read out via the PRE driving GFP, similar to the results in FIG. 3B. The level of GFP activation as a function of β-caryophyllene effector can give an idea of the $EC_{50}$, and hence an idea of the relative affinities of the receptors. Using these methods can allow for achievement of low nanomolar affinity activation, well below current detectable levels with the wild-type CB2 receptor (1.9 micromolar, (Gertsch 2008)), and hence an instantiation of the HAVOC concept. The engineered yeast can be used to assay for cross-reactivity with other potential CB2 effectors. The highest affinity, highest specificity receptors are further characterized in neuronal models, as described below.

To characterize HAVOCs in their target cells, neurons, neurons are transfected with the final mutants and characterize their efficacies at achieving depolarization via calcium-dye assays and electrophysiological characterizations. The orthogonal GPCRs are introduced into mouse brain via an AAV-vector (adeno-associated virus) containing a fluorescent tag that allows for differentiation of transfected from untransfected neurons. Neural tissue is cultured from infected mice and whole-cell current clamps are performed on infected neurons to record changes in resting membrane potential with and without orthogonal ligand (β-caryophyllene) application. Since the variant CB2 receptors should be $G_i$-coupled, a hyperpolarizing potential shift can be seen. Next, whole-cell voltage clamps are used to measure mIPSCs (miniature inhibitory post-synaptic currents), to verify if the receptor has a presynaptic effect. VGAT-specific (vesicular GABA transporter) AAVs are used to target GABAergic interneurons, thus fewer mIPSCs in post-synaptic cells after ligand (β-caryophyllene) application. This not only demonstrates modulation of neurotransmitter release, but also validates bidirectional control over the brain; engineered receptors are used to both inhibit and excite neurons (though the latter only indirectly). Responses of the variant CB2 receptors to other native ligands (such as the cannabinoids) are examined to ensure orthogonality and thereby enable multiplexing capabilities. Finally, experiments are performed in a variety of neural subtypes via cell-type specific AAVs to ensure brain-wide capabilities.

Example 2: Developing Novel, Orthogonal Couples: Cannabinoid Derivatives and Receptors New receptor variants can be identified that can be used as orthogonal pairs in neurobiology. While beta-caryophyllene was an excellent compound for obtaining initial results, as it is the product of a single enzymatic transformation beyond normal yeast metabolism, to generate more useful compounds for neurobiology a pathway where greater chemical diversity could be introduced is used. To this end, the cannabinoid biosynthetic pathway (FIG. 5) has been chosen. This core pathway can be readily modified with both natural and evolved enzymes to diversify the ligand sets for HAVOCs.

CB2 Variants Responsive to Natural Cannabinoids.

The natural biosynthesis of cannabinoids in *Cannabis sativa* can be roughly divided into four distinct metabolic pathways: hexanoate, 2-C-methyl-D-erythritol 4-phosphate (MEP), geranyl diphosphate (GPP), and the penultimate cannabinoid production center (CPC). Given that hexanoate is a relatively simple organic molecule that is commercially available and inexpensive, and that yeast already produce geranyl pyrophosphate, it was hypothesized that cloning the CPC-CBD into *S. cerevisiae* and supplementing with hexanoate would lead to the production of our first effector for a new HAVOC, CBD.

The genes for hexanoyl-CoA synthetase (CsAEE1), 3,5,7 trioxododecanoyl-CoA synthase (OLS), olivetolic acid cyclase (TKS), geranyl-pyrophosphate-olivetolic acid geranyltransferase (CsPT1), and cannabidiolic acid synthase (CBDA) were codon optimized for expression in *S. cerevisae*. These five enzymes were cloned under the control of endogenous promoters: ScTDH3, ScCCW12, ScPGK1, ScHHF2, and ScTEF11, respectively. Promoters were chosen based on published expression profiles and kinetics. Each enzyme was also given a unique terminator to mitigate the potential ejection of pathway enzymes via recombination. All five were assembled along with the Ura3 gene into a single integration vector via a restriction-digestion reaction and cloned into *E. coli* (DH10B). The complete pathway was stably integrated into the ΔUra3 locus of *S. cerevisiae* BY4741 and a BY4741 ΔPep4 knockout.

Figure 6:
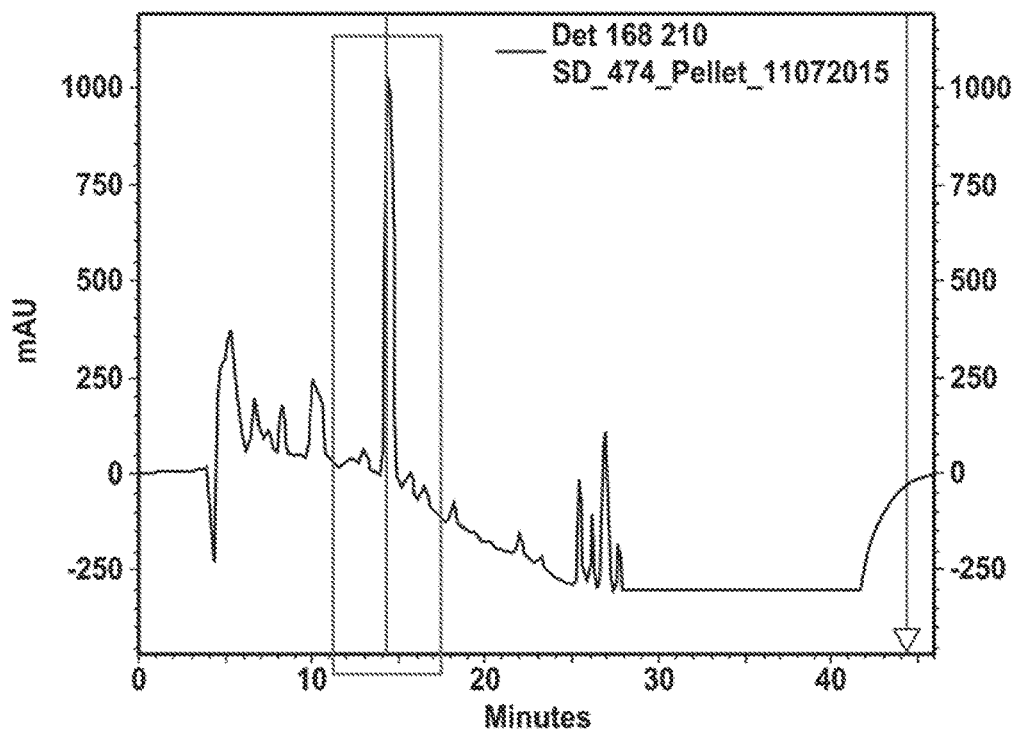
FIG. 6 shows CBD production. Production of CBD was confirmed using HPLC and fragmentation MS. Optimal growth conditions yielded nearly 100% yields from hexanoate supplementation.

CBD was produced in both integrated strains with 1-10 mM hexanoate supplementation. The production of CBD was confirmed by first using standard-based HPLC and fragmentation MS (FIG. 6). These strains were also passaged for 10 days and no errors were found in the pathway upon sequencing.

Functional CB2 expression constructs are now paired with the CBD pathway, rather than the β-caryophyllene pathway, and new CB2 variants are evolved. The ligand-binding pocket of the CB2 receptor is mutagenized, and multiple rounds of positive and negative selection are carried out via the CPR circuit. The sequence of the CB2 library can converge on just a few sequences. As necessary, error-prone PCR is used during amplification to further diversify the library and identify CB2 variants with substitutions peripheral to the binding pocket that may have even greater responsivity to CBD. The wild-type receptor binds its normal agonist, THC (FIG. 7) with roughly 80 nM affinities, and CBD (which does not act as an agonist) with micromolar affinities (Pertwee 2008). Thus, binding of a known ligand is improved, and it is coupled to transduction. Finally, neurons are transfected with the final variant CB2 receptors and their efficacies are characterized at achieving depolarization via electrophysiological characterizations.

Figure 5:
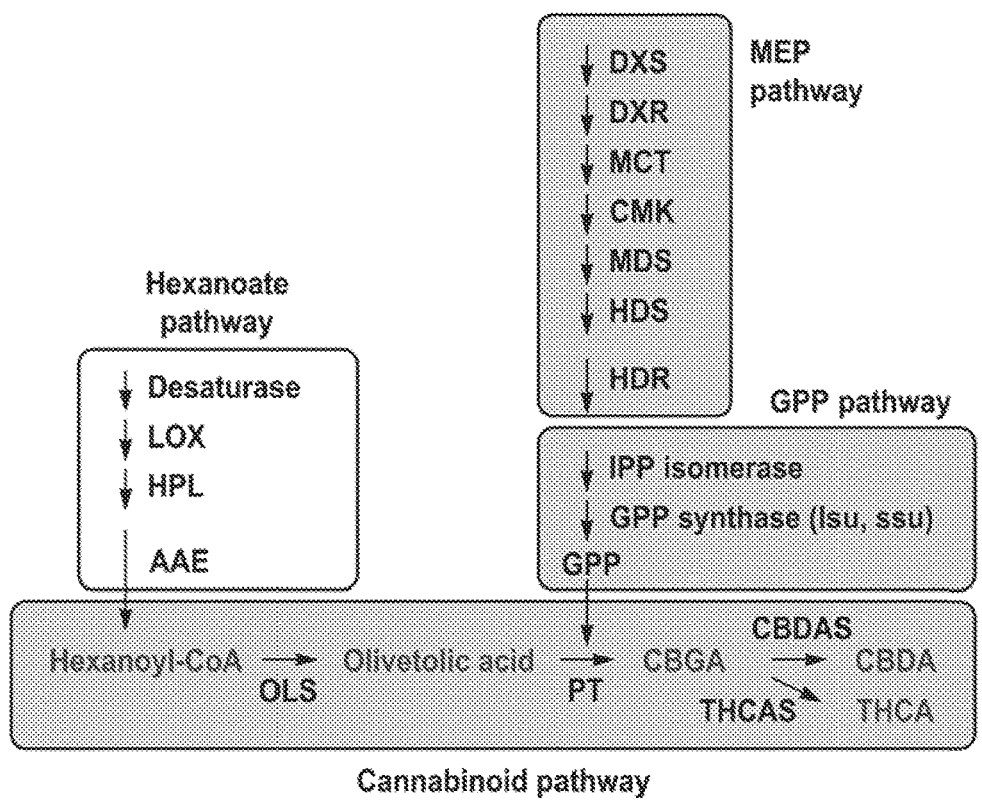
FIG. 5 shows cannabinoid biosynthesis. The modularity of the cannabinoid biosynthesis pathway is shown. With supplementation of hexanoate and endogenous GPP production, only 5 enzymes are needed to produce cannabinoids.
Figure 7:
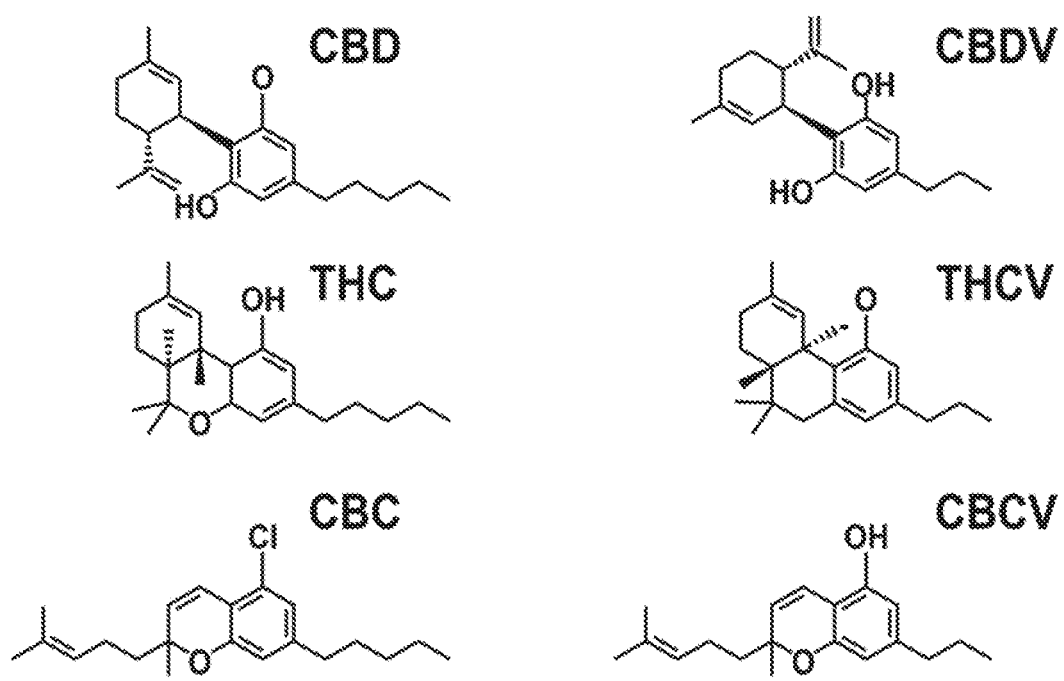
FIG. 7 shows chemical structures for various natural cannabinoids and derivatives.

Having identified CBD-responsive CB2, the ligands and the receptors are further diversified in parallel. The establishment of a robust CBD-producing strain now enables the production of other natural cannabinoids related to CBD (FIG. 7). For example, CBGA is a common intermediate in the synthesis of both CBD and CBC, and by replacing the CBD synthase with CBC synthase CBC can be readily accessed biosynthetically (FIG. 5). Another natural branch point occurs upstream of olivetolic acid, which produces the shorter chain divarinic acid derivatives (CBDV, THCV, and CDCV). These different routes to the production of these four natural cannabinoids (CBC, CBDV, THCV, and CDCV) are constructed with suitable yeast promoters, and cloned adjacent to the CB2 expression libraries.

CPR is used to simultaneously select for which of the four pathways is most functional and can produce compounds that trigger one or more receptor CB2 receptor variants. Since selections are being carried out in emulsions, it is entirely possible that each of the pathways identify one or more different CB2 variants capable of function. The functionality and orthogonality of the CB2 variants with these natural, non-CBD cannabinoids is proofed by transfecting neurons with the final mutants and characterize their efficacies at achieving depolarization via electrophysiological characterizations. The directed evolution of five new HAVOCs (for CBD, CBC, CBDV, THCB, and CDCV), each with nanomolar affinities and proven orthogonality for its particular effector, can thus be achieved.

Unnatural CBD Ligands and Receptors.

Success with CBD and other cannabinoids also makes possible the generation of more exotic, tailor-made effectors. As an example, the addition of other hexanoate derivatives provides a convenient avenue to create novel compounds not otherwise found in nature. For example, feeding experiments are carried out with 2-methyl hexanoate, 3 methyl-hexanoate, and 2-amino hexanoate and assess their entry into novel cannabinoids via HPLC and MS, as in FIG. 6. To the extent that yeast can make these outré compounds, variant CB2 receptors can be evolved to respond to them, creating completely unnatural HAVOC pairs similar to the DREADD pairs already in service. In these cases, orthogonality is guaranteed both by low affinities of the evolved CB2 receptors and by the fact that the compounds may not react with the wild-type CB2 receptor (unlike β-caryophyllene and the natural cannabinoids already described).

Example 3: Neural Ion Channels and rCPR

Towards the creation of a microbial platform for high throughput screening/selection of human neural receptors, the following have been shown 1) the first instance of human neural ion channels functioning in a yeast host and 2) induction of a selection circuit via a calcium dependent promoter via channel opening. These achievements can be deployed together for the directed evolution of receptors, biosynthetic enzymes, or any protein that can directly or indirectly stimulate or inhibit the signaling of a receptor.

Figure 8A:
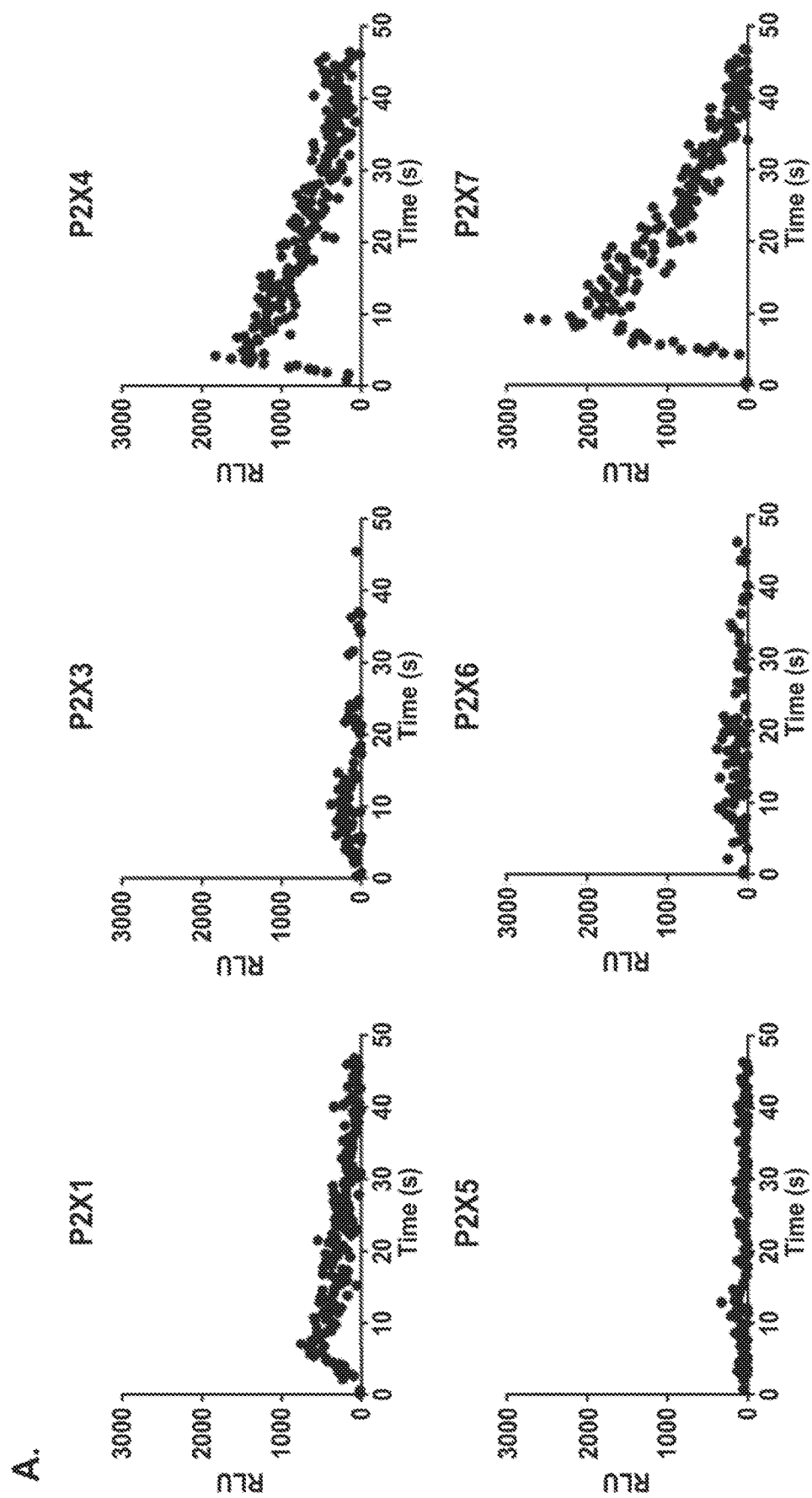

Ion channel activity in yeast was tested with the purinergic P2X ion channel family. Channel gating was assessed by an aequorin assay in which aequorin is co-expressed with the receptor and, upon addition of the prosthetic group coelenterazine and addition of calcium, blue light is released. The aequorin-based functional assay was performed in all seven P2X receptors (FIG. 8). P2X1-7 were integrated into the chromosome to mitigate copy number variation between clones and were induced with galactose with the pGal1 promoter. Upon ATP ligand addition, it was found that several P2X receptors gate in a ligand-dependent manner. Notably, P2X1, P2X2, P2X4, and P2X7 showed an ATP-dependent calcium influx. Among those receptors that didn't work, it was suspected that improvements in expression and trafficking can improve functionality. For example, by modulating trafficking domains within the P2X4 receptor, aggregation was reduced in vesicles (FIG. 9), and it is believed that this tactic can be employed in other receptors. Among the functional channels in the screen, P2X2 showed a ligand-gated response orders of magnitude greater than the other receptors, and displayed luminescence nearly 1000-fold higher. This can be because P2X2 has the slowest desensitization rates of the family (and is often considered "non-desensitizing") and has the highest unitary conductance (30 pS).

Since the P2X2 functionality was by far the most robust in the screen, a full kinetic analysis was performed to verify the properties of this receptor in yeast. To this end, a dose-response assay was performed (FIG. 10). It was determined that the EC50 value was $6.7 \pm 1.5$ µM, which closely matches literature values. To further verify that P2X2 demonstrates similar properties in both mammalian and yeast hosts, a battery of kinetic assays was performed with agonists 2-Chloro ATP (2-Chloro-Adenosinetriphosphate) and BzATP (2'(3')-O-(4-Benzoylbenzoyl)adenosine-5'-triphosphate) and the antagonist suramin. Agonists displayed dose-dependent responses that matched expected values, in which 2-Chloro ATP showed full agonist behavior with an EC50 of $26.7 \pm 1.5$ µM and Bz-ATP showed a partial agonism with an EC50 of $29.1 \pm 6.0$ uM and peak amplitudes only reaching approximately 20% of that achieved with ATP. As a final means to verify that the P2X2 receptor was gating in a ligand-dependent fashion, a previously characterized mutant was built and tested. P2X2 with a broken ligand-binding pocket via K81C K83C mutations was built, and as expected, showed no agonism versus its wild type counterpart.

These data report the first example of human neural signaling in yeast. An in-depth kinetic analysis further shows that the signaling profiles measured in yeast are one-to-one translatable to those derived from more typical neural receptor hosts such as mammalian cells. These open avenues for novel cost-efficient microbial drug screening platforms in addition to the intended purposes of directed evolution, and screening has been done in 96-well plate format and discovered previously unreported permissive mutations that sustain agonism with the native ligand.

To use neural-channel endowed yeast in compartmentalized partnered replication (CPR) schemes, yeast strains were constructed in which calcium influx via opened P2X receptors drive expression of a thermostable polymerase to participate in compartmentalized partnered replication (CPR). To do this, promoters were designed containing two, three, four, or six repeats of the calcineurin-dependent response element (CDRE) followed by the Cyc1 core promoter sequence. Receptor-mediated calcium influx should allow the calcium-inducible transcription factor Crz1p to initiate transcription upon cooperative CDRE binding. The four versions of the promoter plus KOD polymerase were built into expression vectors for high-copy, low-copy, and genome-integrated expression. To test the strength of promoter induction upon P2X opening, a "mock selection" was performed in which a wild-type and the ligand-binding pocket "broken" P2X2 receptor were compared to determine the fold-induction of the circuit. Specifically, cultures were induced containing the wild type or broken receptor with ATP ligand for an hour, and then emulsified the cells for an emulsion PCR in the presence of primers that amplify the P2X gene. The DNA encoding the broken receptor contained a restriction site such that the wild-type and broken receptor cultures could be consolidated, and the PCR product could be run on a single lane to determine the ratio of amplification of the two samples. Initial testing of the integrated 2×CDRE-KOD in the mock selection has yielded up to 5-fold induction of the circuit (FIG. 11).

Example 4: The Development of Compartmentalized Self-Replication in a Eukaryotic Organism Compartmentalized Self-Replication was adapted to *Saccharomyces cerevisiae*. This is referred to herein as yCSR. This was an initial proof-of-concept to show that emulsion-based PCR selections would be compatible with yeast. Describe herein is: (1) the optimization of emulsion bubbles that would encapsulate single yeast cells; (2) the stabilization of emulsions to endure overcycling; (3) the process of expressing a thermostable DNA polymerase and amplifying its gene within the emulsion; and (4) the optimization of the buffering conditions to allow for in emulsion spheroplasting of cells. The protocols developed here are the basis for yCSR and yeast-based Compartmentalized Partnered Replication (yCPR). The adaptation of emulsion PCR-based selection methods to a eukaryotic organism enables the engineering of a number of protein classes not accessible to selections performed in bacterial systems.

Results & Discussion
Emulsion Optimization

Figure 14:
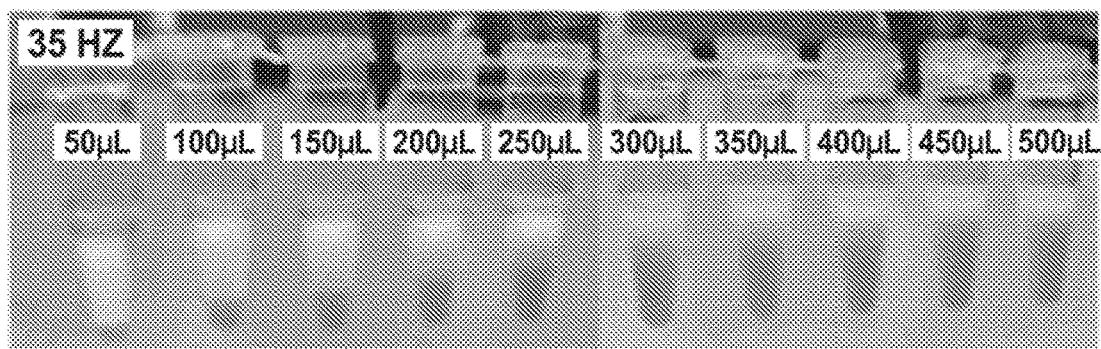
FIG. 14 shows stable yeast emulsion optimization. Increasing the amount of cells/aqueous phase in the setup of the water-in-oil emulsion stabilized the emulsions.
Figure 15:
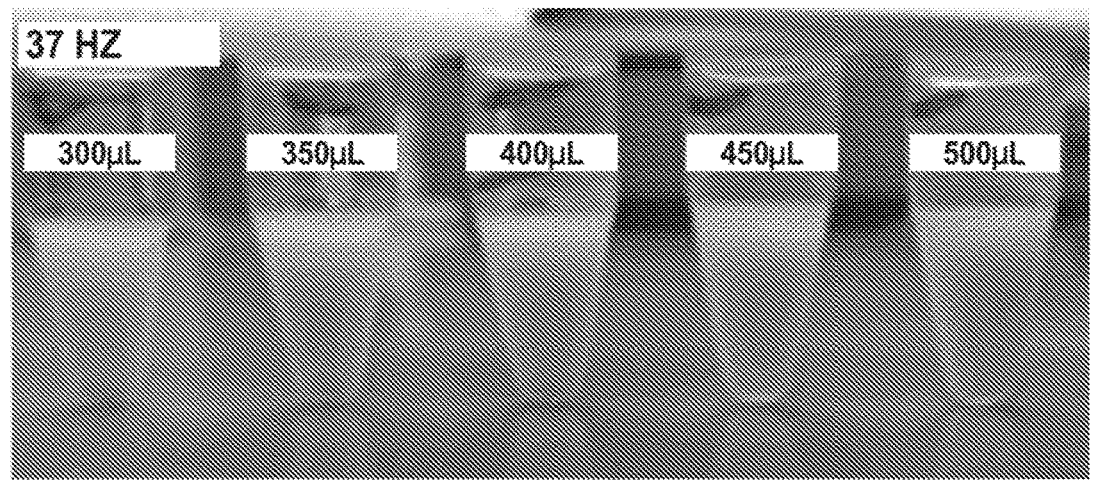
FIG. 15 shows final yeast emulsion stability. Final stability conditions tested at 37 Hz, 5 min in tissuelyzer. The 500 μL aqueous phase treatment showed the highest level of emulsion stability.

The ideal range where immersion bubbles were the same size laid somewhere between 35-40 Hz. Next, the length of time (4-11 minutes) needed to produce large, uniform emulsions, capable of comfortably accommodating yeast cells was determined. In the end, 37 Hz for 5 minutes was shown to be the optimal set of parameters to emulsify yeast in our water-in-oil emulsions. Brightfield images, processed by ImageJ, were used to determine the size of the emulsions, and yeast cells could be accurately visualized by constitutively expressing yeCitrine, a fluorescent reporter. Doing so would allow images to be taken using fluorescent microscopy to verify that the cells were still intact after emulsification (FIG. 12). To test for emulsion stability, the emulsion was aliquoted into PCR tubes and thermocycled as in a typical CSR or CPR reaction. 35 cycles of PCR were lysed, as this would be the upper end of the number of cycles used in a directed evolution experiment. The amount of surfactant, oil, aqueous phase (buffer and cells), and mineral oil needed to produce stable emulsions, capable of enduring long cycling conditions was optimized. Stability was easily monitored at this stage. Unstable emulsions would phase separate, while stable emulsions would remain uniform (FIGS. 13 and 14). In the end, a number of optimal parameters that allowed emulsification of yeast in thermostable emulsion bubbles was found (Table 1; FIG. 15).

Yeast CSR Mastermix Optimization

Figure 16:
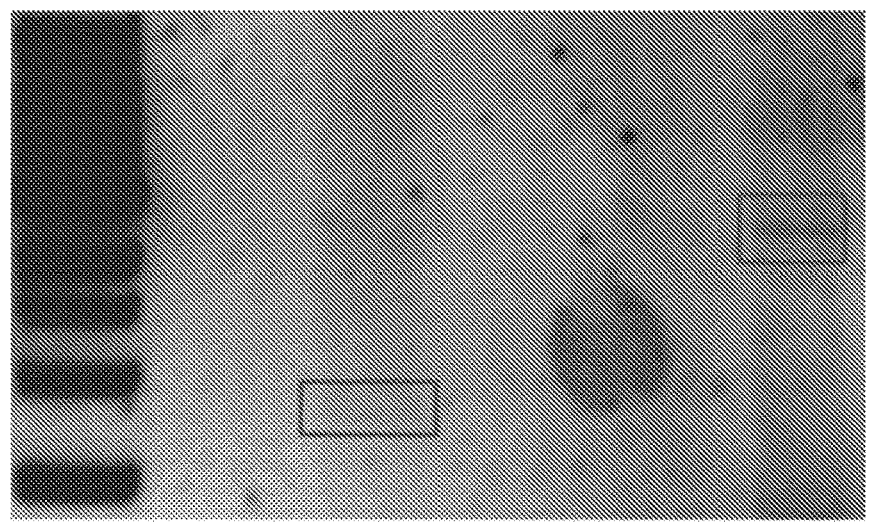
FIG. 16 shows original CSR conditions using spheroplasted cells. Yeast CSR-derived amplicons targeting a 700 bp fragment (left) of KOD and the full 2.5 kbp gene (right). This initial proof-of-concept was performed using pre-spheroplasted cells.

To perform CSR in yeast, strains with yeast codon-optimized KOD were built under the control of the pGal1 promoter. After induction, yeast were emulsified in standard CSR buffer and products run out on a gel. Using normal CSR mastermix from 244 bacterial cell selections, no amplification occurred. This could have been due to cells not lysing under normal PCR cycling conditions. The yeast cell wall is impervious to heat, and colony PCR of yeast requires pretreatment with softening agents and typically zymolyase, an enzyme that rapidly degrades the cell wall. To test this hypothesis, cells were spheroplasted before the putting the cells in the emulsion. In spheroplasted cells, product was visible on an agarose gel. It was next determined if spheroplast could occur within the emulsion. That is, add zymolyase to the mastermix and incubate cells at 3TC before starting the normal cycling conditions. Spheroplasts are fragile, and it was a concern that cells would rupture during the emulsification process. Initial attempts at adding zymolyase failed. However, it was found that if cells were softened using sorbitol, DTT, and EDTA, detectable levels of amplification occurred (FIG. 16).

Figure 17:
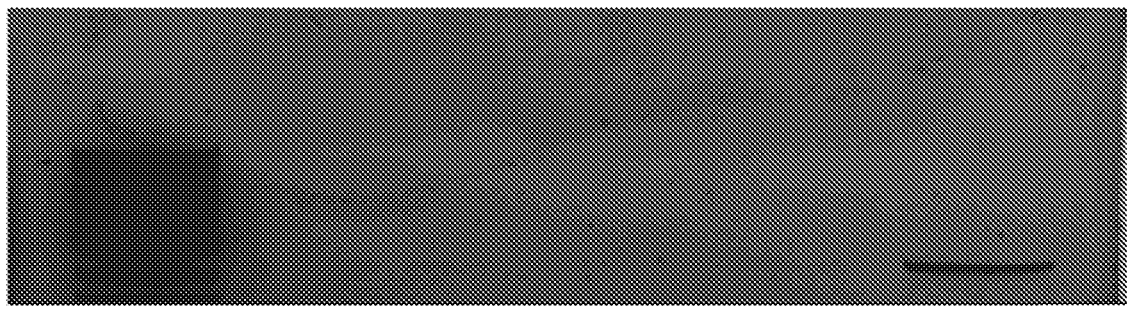
FIG. 17 shows zymolyase optimization. Varying amounts of zymolyase (0-80 μL) used in the optimization of yeast CSR.
Figure 18:
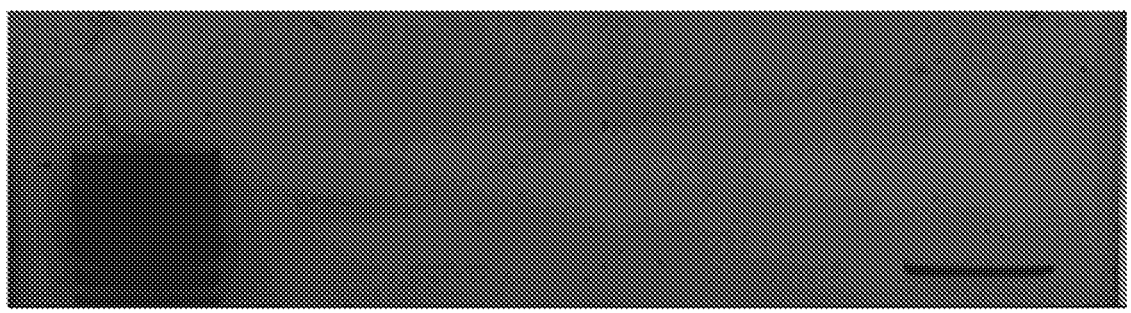
FIG. 18 shows dNTP optimization. Varying concentrations of dNTPs (0-450 μM) used in the optimization of yeast CSR.
Figure 19:
FIG. 19 shows primer optimization. Varying concentrations of primers (0-7.5 μM) used in the optimization of yeast CSR.
Figure 20:
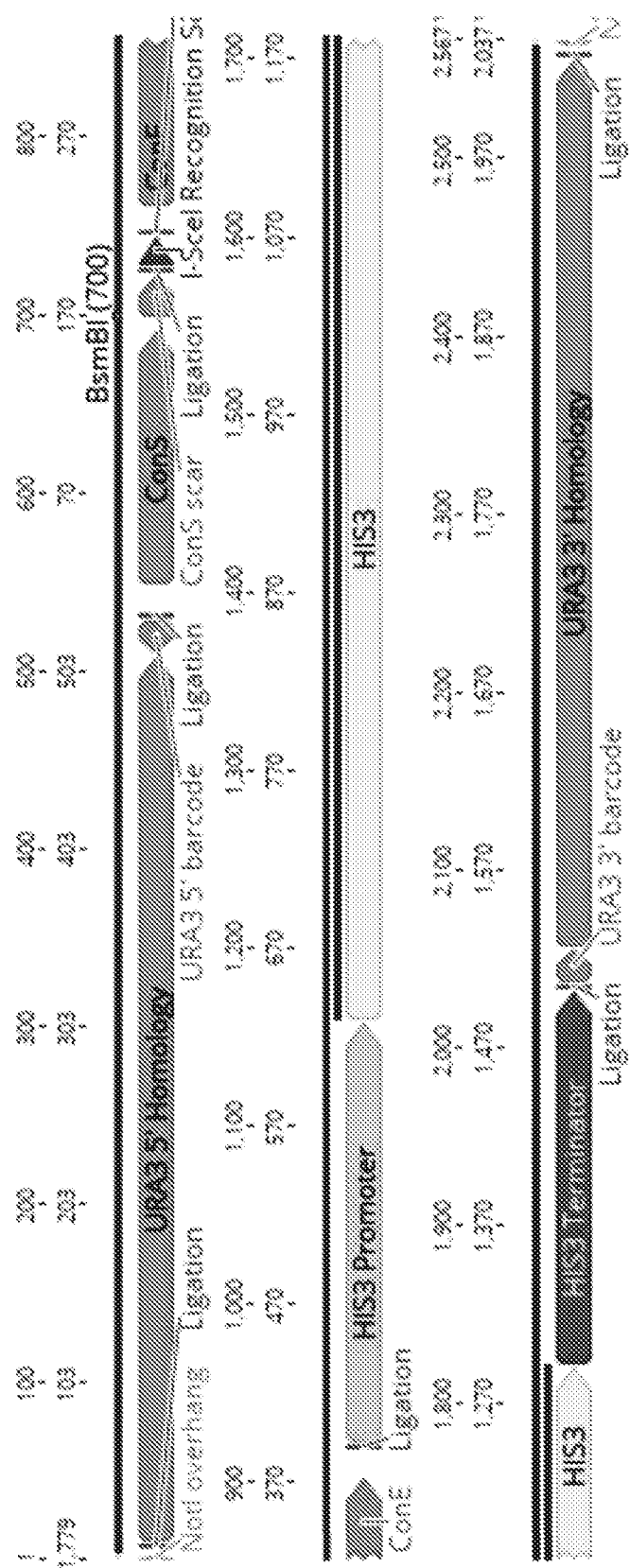
FIG. 20 shows Ura-His3 IsceI site. Recognition site is shown between connectors S and E. His3 selection marker is used at the Ura3 site in targeted strains.
Figure 21:
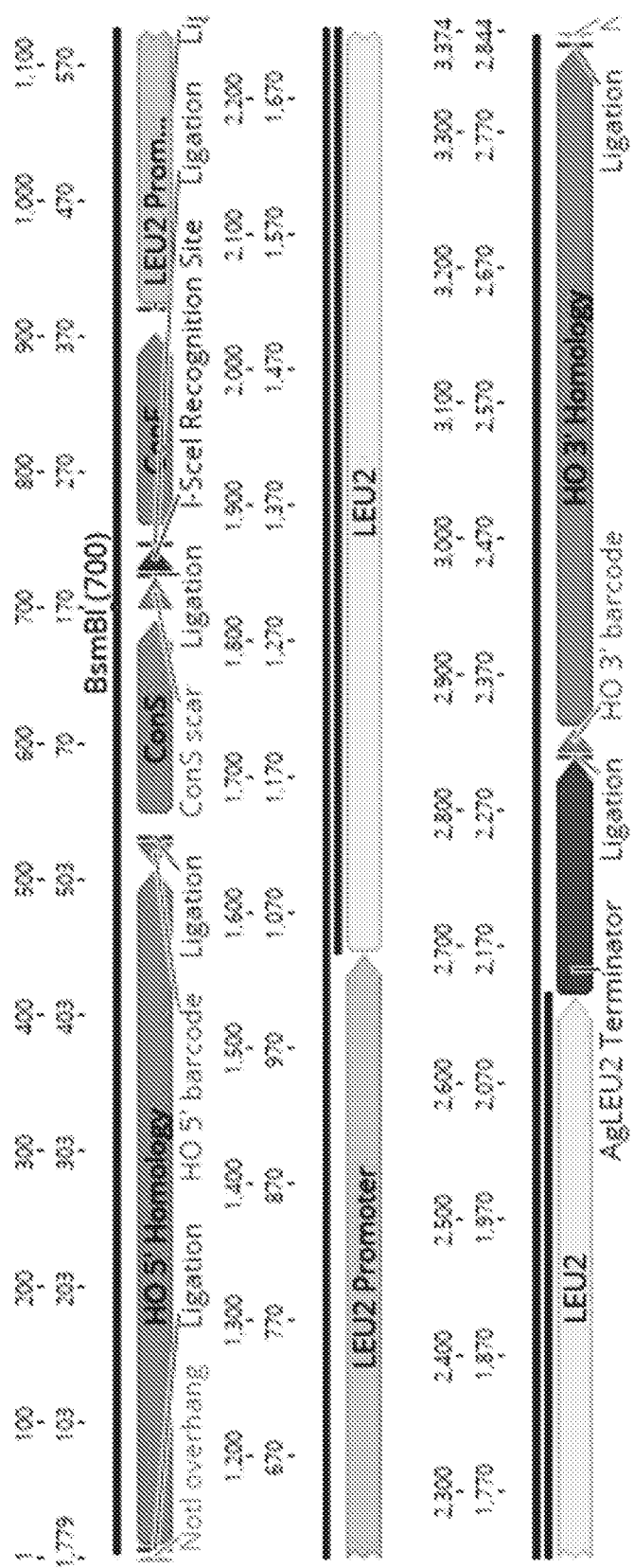
FIG. 21 shows HO-Leu2 IsceI site. Recognition site is shown between connectors S and E. Leu2 selection marker is used at the HO site in targeted strains.
Figure 22:
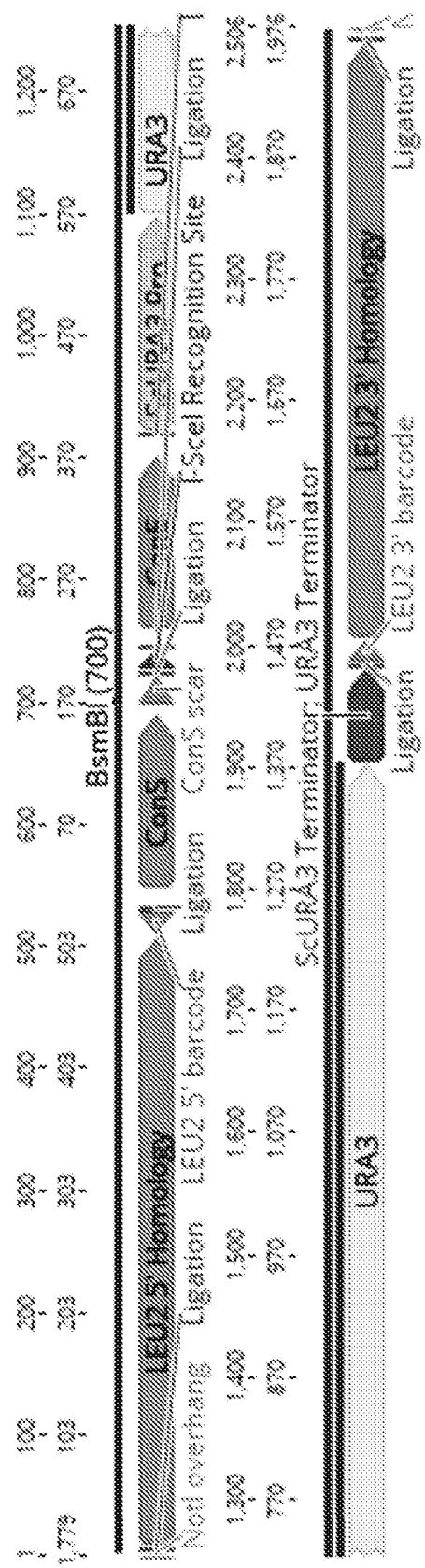
FIG. 22 shows Leu-Ura3 IsceI site. Recognition site is shown between connectors S and E. URA3 selection marker is used at the Leu2 site in targeted strains.
Figure 23:
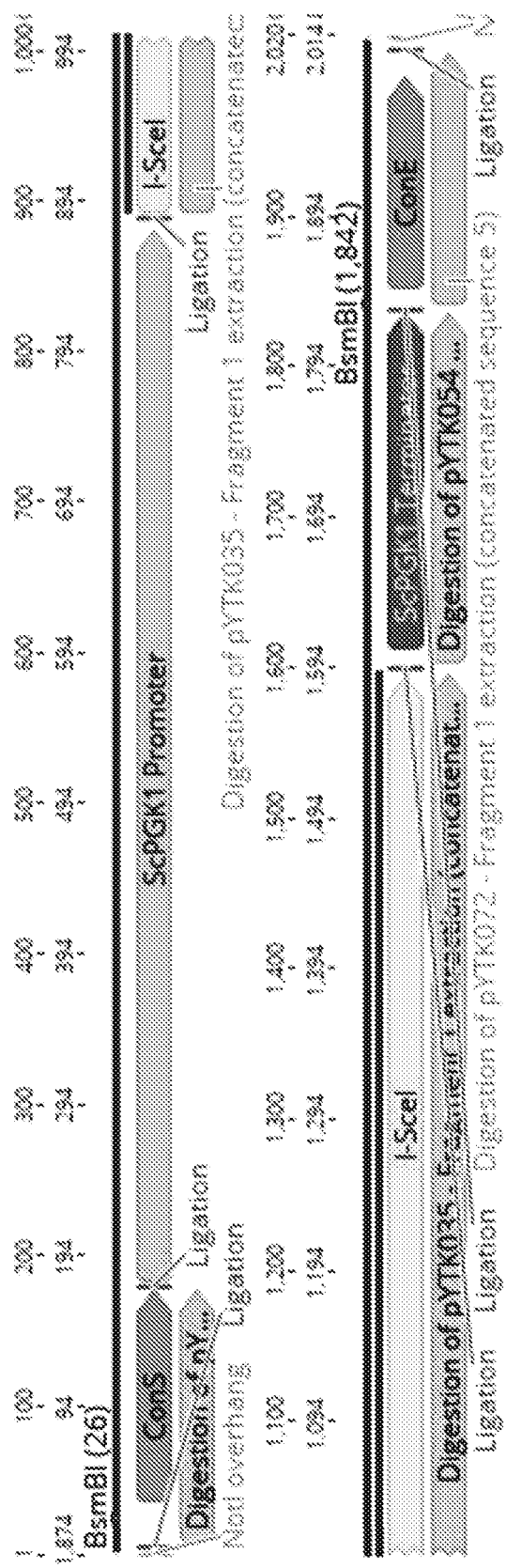
FIG. 23 shows IsceI cutter plasmid. The IsceI linear fragment is shown. The enzyme is expressed under the PGK1 promoter/terminator pair. The expression of the enzyme is transient because there is no selectable marker and the piece is linear.

A number of optimization experiments were then initiated. Optimization was tested by testing the amount of zymolyase needed. It was found that as little as 80 uL of a 5 mg/mL stock was adequate in initial testing. There seemed to be diminishing returns above this value (FIG. 17). Next, the concentrations of dNTPs and primers in the mastermix was varied. Commercial zymolyase preparations tend to have trace phosphatases and nucleases. A modest improvement was seen using 300 µM dNTPs (FIG. 18) and 4 µM of each primer (FIG. 19), much higher than a typical PCR reaction. It was then determined if adding tetramethylammonium chloride (TMAC), a known PCR enhancer, had an effect on the emulsion PCR product. It was found that increasing concentrations improved amplification (10-300 µM TMAC). Finally, it was determined that polymerases were more active in the CSR reaction in Tris-SO$_4$, pH 8.0 supplemented with 1 mM MgSO$_4$. The original CSR mix was conducted at pH 8.8 for historical reasons, which may be a way to tune stringency in both CSR and CPR evolution experiments. The optimized concentrations of each component can be found in Table 2.

Yeast Selection Strain Creation

Homologous recombination is a benefit of using yeast over bacterial cells in performing CSR or CPR selections. By transforming libraries into the yeast chromosome, copy number variability found in plasmid-based selections is mitigated. In order to streamline the process, a number of yeast strains harboring IsceI cut sites and auxotrophic markers at the common Ura, Leu, and HO sites (Lee et al., 2015) were created. For example, at the Ura integration site, a vector was integrated containing the IsceI cut site along with a histidine prototrophic marker. When transforming libraries with a uracil marker into this position along with a linear plasmid that transiently expressed IsceI nuclease, an average of $7.5 \times 10_7$ transformants were seen, which is nearly as large as seen in bacterial cells ($\sim 10_8$). By changing out prototrophic markers, background is eliminated during library construction. Plasmid maps for these vectors can be found in FIG. 20-23.

Additional Directions

The development of long-read enzymes or PCR-based replication machinery has remained elusive due the size constraints in plasmid-based systems. In order to select for highly processive, high-fidelity replication machinery, CSR has been adapted to Saccharomyces cerevisiae where integration of libraries into the chromosome is trivial, allowing for much longer amplification reactions within the emulsion PCR. It should now be possible to evolve an archaeal Family B DNA polymerase alongside its cognate proliferating cell nuclear antigen (PCNA) clamp. The successful selection of a DNA polymerase:PCNA pair enables the amplification of much longer stretches of DNA.

The proliferating cell nuclear antigen (PCNA) is a clamp that is used to increase the processivity of DNA polymerases during replication in archaeal and eukaryotic organisms.

Figure 24:
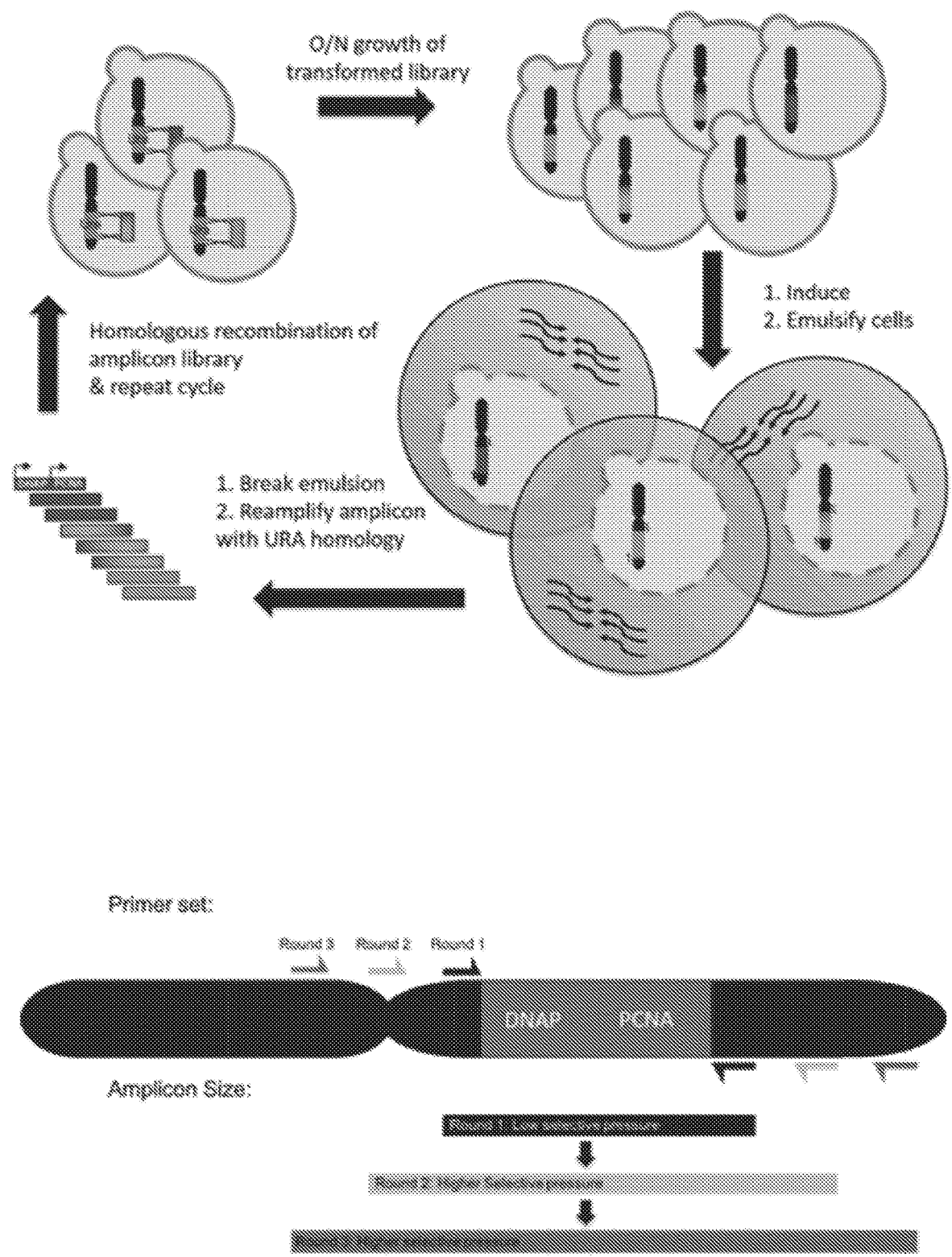
FIGS. 24A and B show long-read yCSR.

Typically, the clamp is loaded during replication fork creation by the RFC clamp loader. The combination of the clamp and polymerase ensures that tens of thousands of bases are faithfully replicated without loss of the DNA polymerase. An engineered variant (E143K) of the proliferating cell nuclear antigen (PCNA) from Thermococcus kodakarensis (KOD), has been shown previously to be functional in PCR applications (Kitabayashi et al., 2002; Kranaster and Marx, 2010). In order to enable the amplification of long amplicons assembled in yeast, it can be possible to insert the PCNA and the Family B DNA polymerase (also from T. kodakarensis) genes into our selection strains using pGal1 and pGal10 (Lee et al., 2015) and select long-read replication machinery (FIG. 24).

Example 5: Functional Expression of Human GPCRs and Plant Cannabinoid Biosynthetic Pathways in Yeast By disrupting a number of genes in the pheromone response pathway, dose-dependent signal transduction of human serotonin receptor (5HT1A) and cannabinoid receptor subtype 2 (CB2) can be shown with the addition of their native ligands to yeast growth media. To create antagonism-based circuitry an inverter circuit was engineered and proofed. The production of the dietary cannabinoid β-caryophyllene and autoactivation of an engineered strain expressing CB2 was shown. The optimization of cannabidiol (CBD) producing yeast strains.

GPCR Strain Construction

The ability to manipulate native GPCR signaling in S. cerevisiae has proven to be a valuable tool in a number of high-throughput screening and directed evolution methodologies (Brown et al., 2000; Ladds et al., 2005; Nakamura et al., 2015; Reilander and Weiß, 1998; Yoshimoto et al., 2014). The deletion or disruption of Sst2p, Ste2p, and Far1p from the yeast genome allows downstream host signaling to be completely seized by heterologous receptor function. By producing chimeric and transplant G$_\alpha$ subunits, it has proven possible to couple receptor function to the production of auxotrophic markers, fluorescent proteins, and enzymatic reporters under the control of pFus1 or pFig1, the commonly used native pheromone response promoters that are activated by the MAPK signaling cascade. Transplanting the last 5 amino acids of the human subunit to the native yeast protein has proven sufficient to couple the heterologous expression and function of a foreign GPCR to the native pheromone response in yeast (Table 3).

Figure 25:
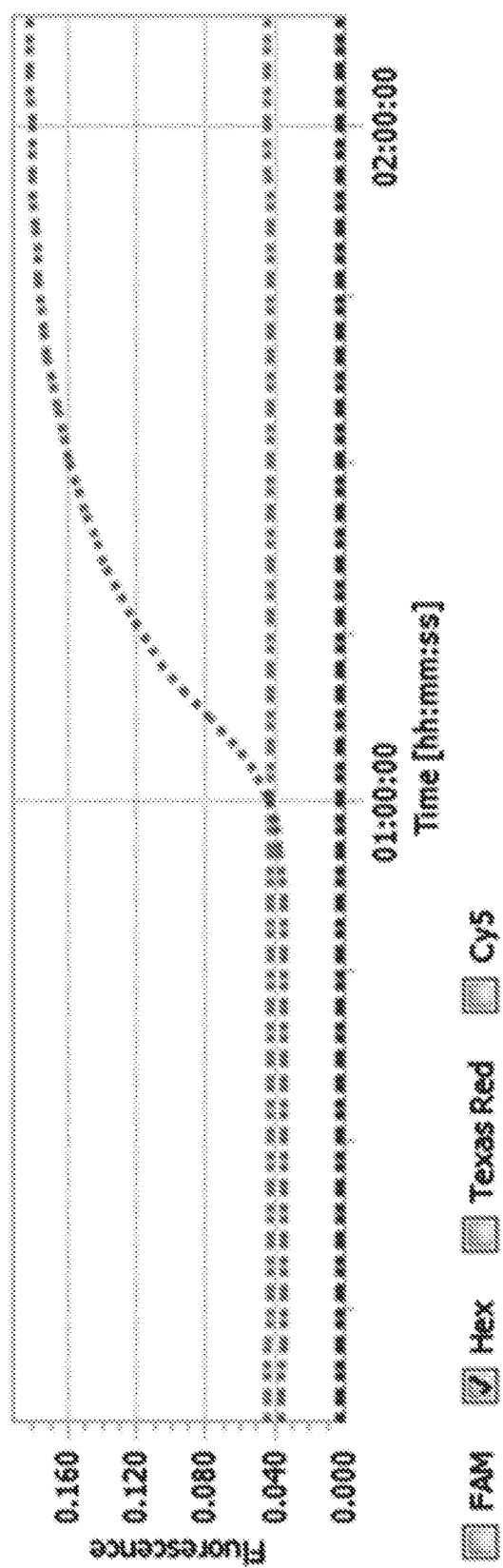
FIG. 25 shows representative qPCR detection of bar-codes. Blue line represents sequence-verified strain containing a disrupted Ste2. Redline is the unaltered BY4741. qPCR could be used to distinguish between the wildtype sequence and a disrupted gene.
Figure 26:
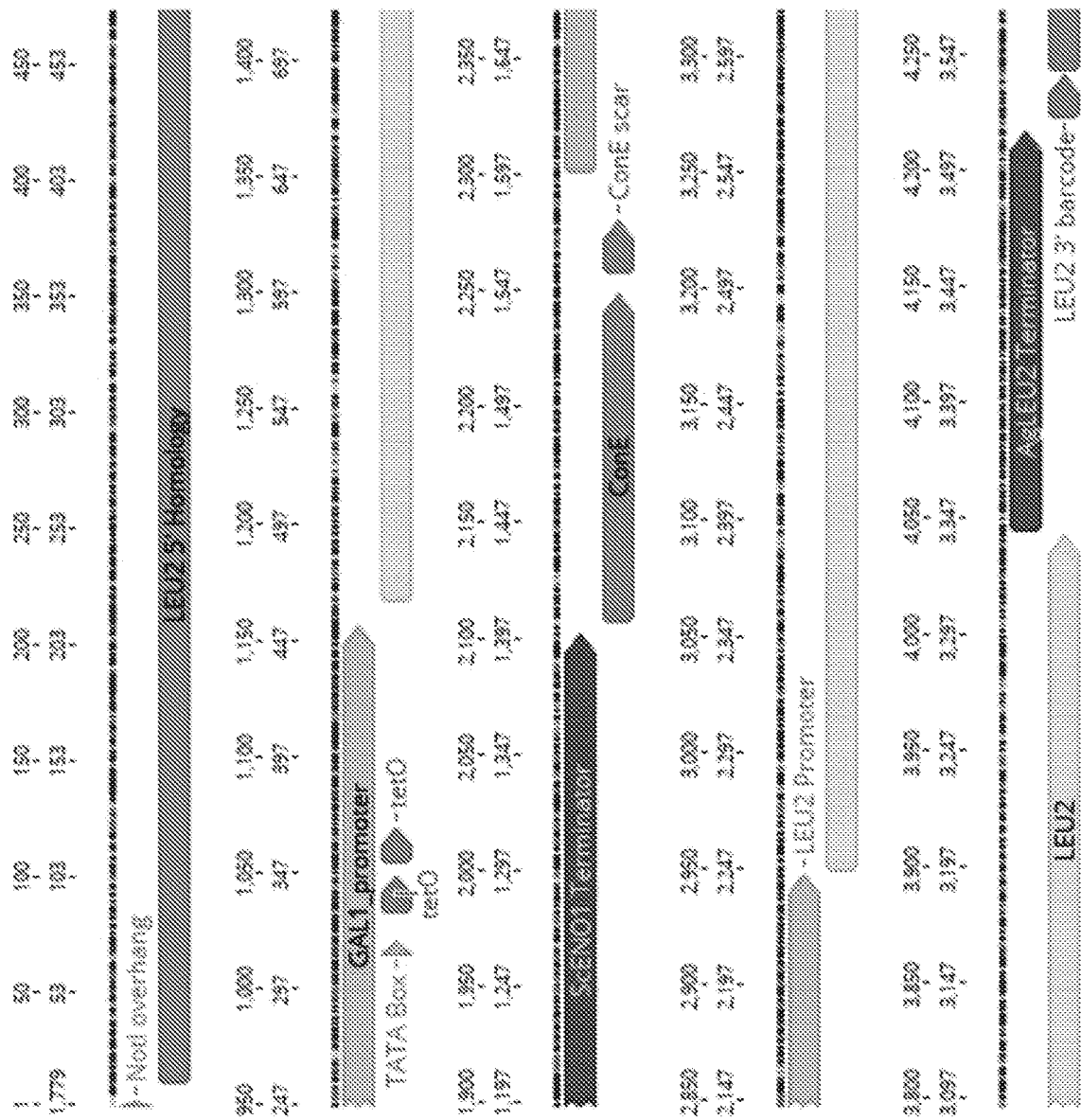
FIG. 26 shows inverter circuit reporter depicted. The construct was inserted into the Leu2 site by supplying an auxotrophic marker. The reporter, zsGreen1, is driven by a modified Gal1 promoter. Two tetO sites are located downstream of the TATA box and prevent transcription when bound by tetR.
Figure 26:
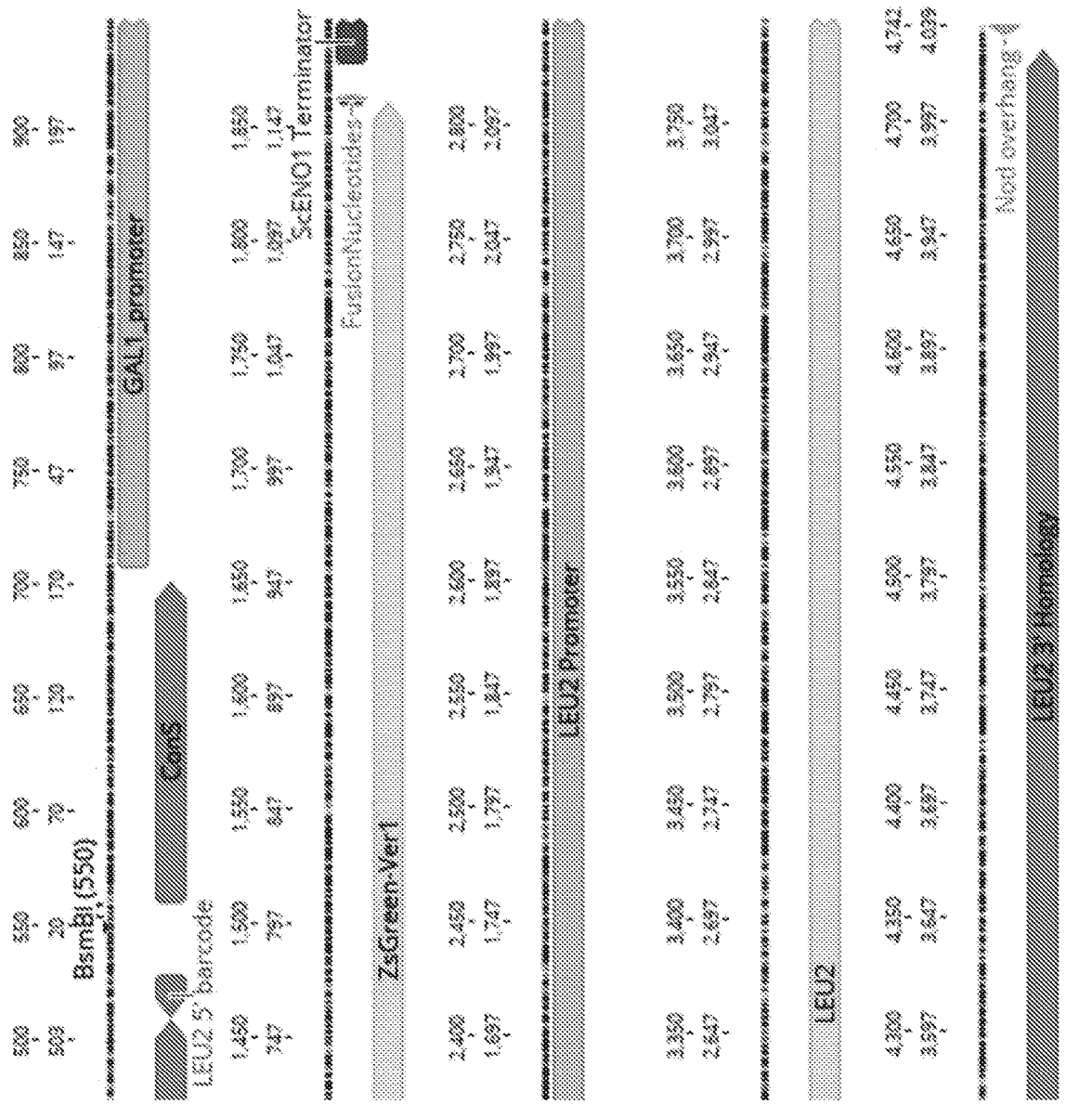

While strains exist with each of the necessary modifications, they are difficult to obtain, and markerless versions using Cas9 were built. Benchling was used to identify potential sgRNAs for each of the targeted genes. 3 sgRNAs were built for each of the targets (Table 4) and tested the efficiency of knockouts (Ste2p, SSt2p, and Far1p), gene replacements (reporters), and site directed mutagenesis of the carboxy terminus of the native yeast Ga subunit (Table 5). For gene disruptions or knockouts, repair DNA was designed that inserted an in-frame stop codon towards the 5' end of the gene along with a barcode that was useful with qPCR probes for multiplex detection of genomic alterations (FIG. 25). For gene replacements at pFig1 or pFus1, the native gene was targeted and inserted either: (1) the archaeal Family B DNA polymerase KOD for use in agonist-driven CPR circuits; (2) the fluorescent reporter zsGreen1; or (3) the bacterial tetracycline repressor (tetR) to be used in inverter circuits for coupling antagonism of a GPCR to CPR circuits. To change the Ga subunits the codon usage at the Cas9 cut site was changed along with changing the terminal 5 amino acids at the carboxy terminus for coupling to heterologous GPCRs. Strains were constructed in BY4741ΔGal2 to enable dose-response activity of the pGal1 and pGal10 promoters (Table 6). In total, 49 strains were constructed for GPCR-dependent experiments. The sequence-validated strains constructed here can now be used for GPCR-CPR in agonist and antagonist mode as well as in FACS-based selections. Further, the zsGreen1 strains can be used in plate-based fluorescence assays. In addition, the tetR strains can be coupled with any reporter under the control of a hybrid pGal1-tetOx2 promoter (FIG. 26). Each of the alterations were made without using common auxotrophic or antibiotic resistance markers, making them easier to manipulate, engineer, or customize.

Functional Expression of Human 5HT1A

Figure 27:
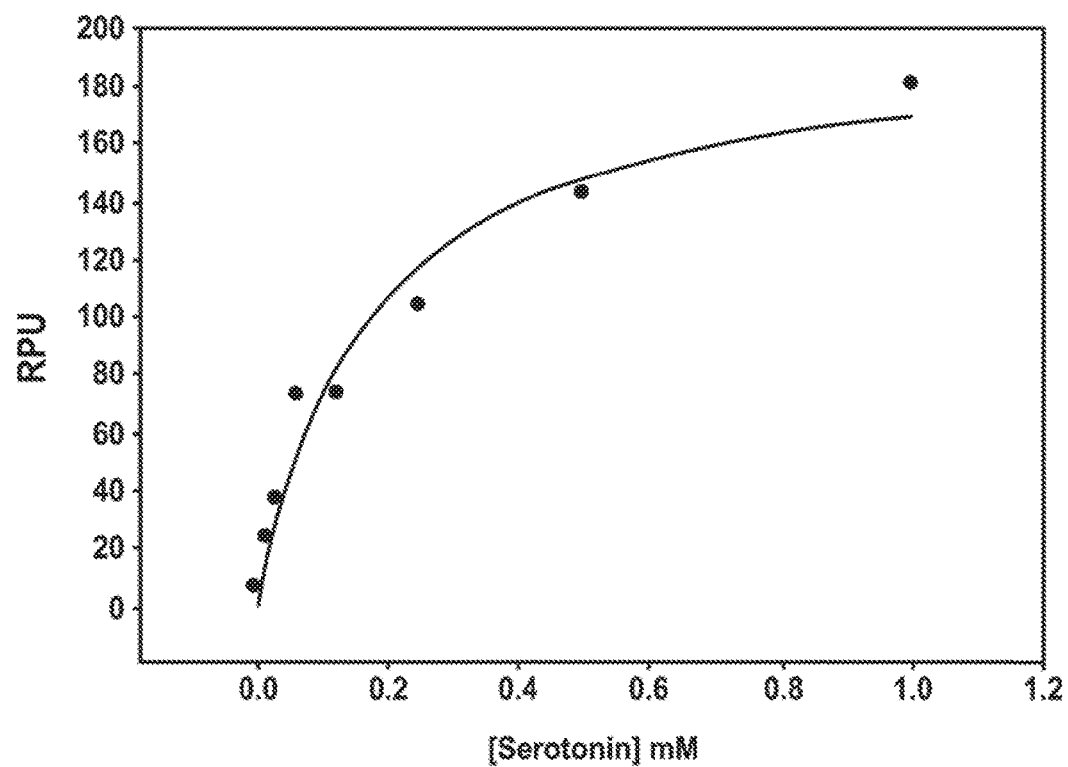
FIG. 27 shows 5HT1A dose-response to serotonin. Dose-response of JG05-2.0 expressing human 5HT1AR from a 2 micron plasmid. Each point is the average of replicates. EC50=171.6 μM.

The human serotonin receptor (5HT1A) has been previously shown to function in yeast using strains similar to those outlined above (Nakamura et al., 2015). To test newly created strains, expression vectors were constructed containing human 5HT1A under the control of the strong, constitutive pTDH3 promoter. A single integration was tested vector along with a high-copy plasmid (2 micron) in JG05 strains. It was found that reporter strains using the pFus1 promoter had high levels of background. Strains utilizing pFig1 showed a good dose-response relationship with the 2 micron plasmid (high-copy), exhibiting far superior signal:noise (FIG. 27).

Figure 28:
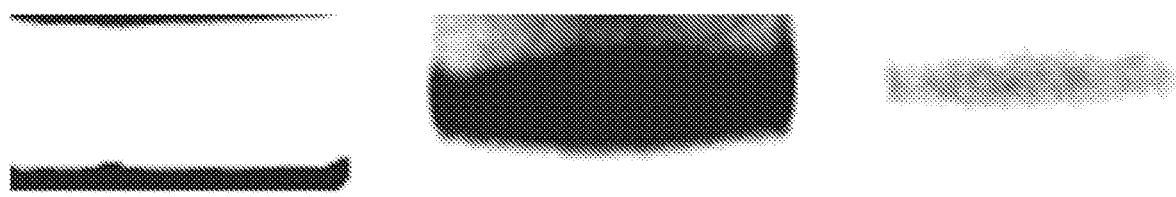
FIG. 28 shows initial proof-of-concept GPCR-CPR. Human 5HT1A was constitutively expressed from a single-copy integration vector inserted at the HO site. Lane 1 is a 1 kb ladder. Lane 2 is the amplification product of cells treated with 250 μM serotonin. Lane 3 represents the negative control. There is a 20-fold increase in signal with cells treated with the ligand.

Having shown functionality of the 5HT1A receptor, CPR strains (JG05-1.0) were constructed using this receptor. Initial coupling to CPR circuits showed a high level of background. However, background was mitigated by increasing the pH of the CPR master mix to pH 8.8 and lowering the number of cycles from 35 to 20 during the emulsion PCR. This resulted in a 20-fold increase in signal:noise and marked the first example of a CPR circuit functioning in a eukaryotic organism (FIG. 28). Further optimization of expression parameters can greatly increase the signal:noise. For example, a much more pronounced difference can be seen when expressing the receptor from a high-copy plasmid. The experiments outlined here were also performed with cells growing with the ligand for 18 hours. By concentrating the cells and limiting the time of induction, a decrease in background signal can be seen.

Inverter Circuit Design, Construction, and Validation

In order to couple antagonism to CPR, an inverter circuit was devised. In this scheme, activation of the GPCR triggers the expression of bacterial tetR, which then in turn inhibits the inducible expression of a modified Gal1 promoter containing 2 tet operator sequences downstream of the TATA box. The details of this hybrid promoter have been discussed elsewhere (Nevozhay et al., 2009). If the GPCR is inhibited, then tetR is not produced, and the promoter is inducible with galactosidase. This circuit could also be used in the engineering of receptors. Often, GPCRs show a low level of constitutive activity. Using the inverter circuit described here, it should prove possible to select against constitutive activity or receptor activation by off-target ligands, thereby increasing sensitivity and selectivity.

Figure 29:
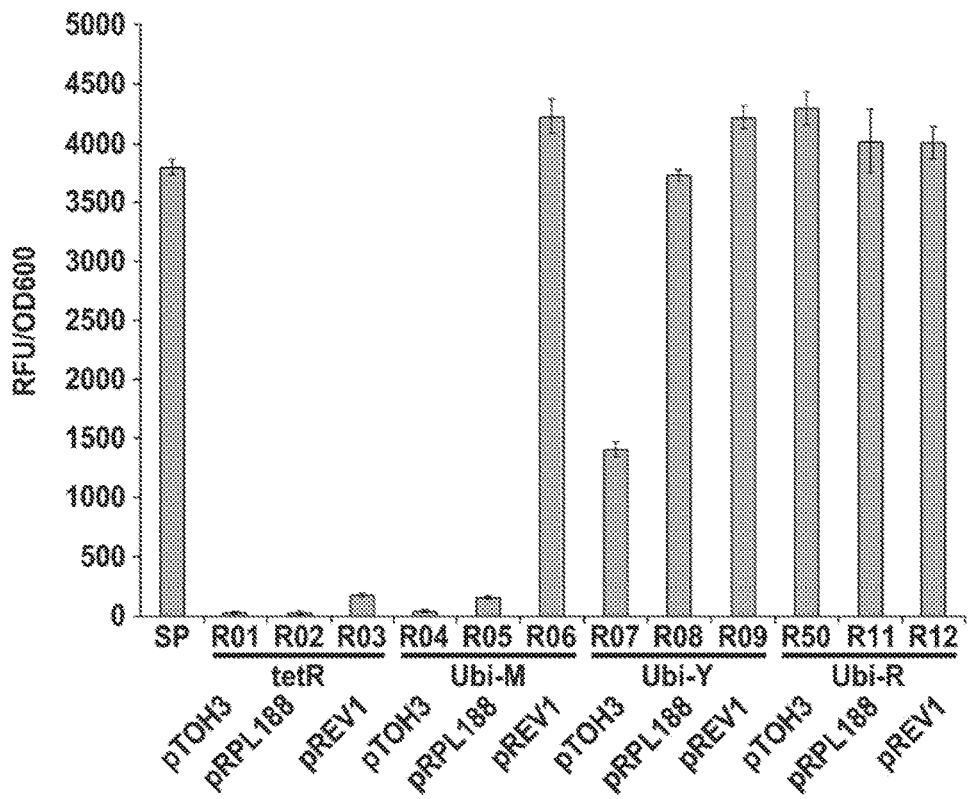
FIG. 29 shows inverter circuit proof of concept. Normalized fluorescent measurements were taken after 18 hrs of galactosidase induction. SP refers to a spacer and does not contain any form of tetR. Ubi-M/Y/R are degradation tags added to the N-terminus of tetR. They are ordered in range of strength. Promoters driving the expression of tetR variants are listed below. They are arranged in order of high to low.
Figure 30:
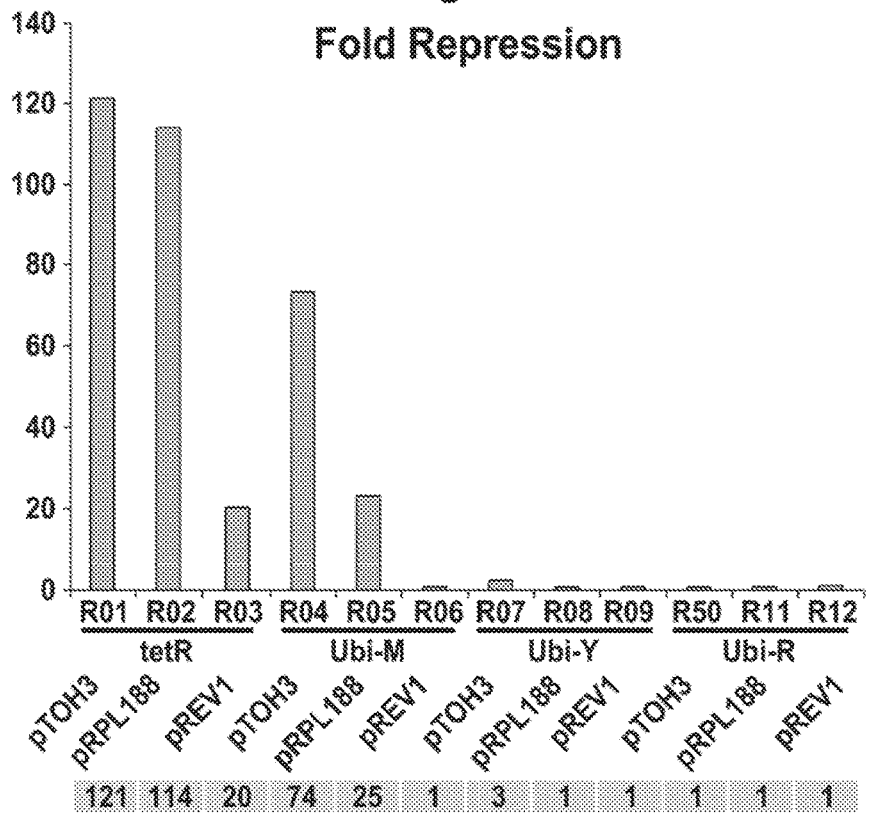
FIG. 30 shows inverter circuit fold repression. Normalized fluorescent measurements were taken after 18 hrs of galactosidase induction. SP refers to a spacer and does not contain any form of tetR. Ubi-M/Y/R are degradation tags added to the N-terminus of tetR. They are ordered in range of strength. Promoters driving the expression of tetR variants are listed below. They are arranged in order of high to low.

To test the feasibility of this approach, strains were constructed with the fluorescent reporter zsGreen1 under the control of the hybrid Gal1-2×tetO promoter in single-copy integration vectors. Integration vectors were also created containing tetR with a nuclear localization signal and tetR variants with degradation tags of varying strengths (Lee et al., 2015). Expression of the tetR was tuned with low, medium, and high strength constitutive promoters. The idea was to gauge the dynamic range of the system and potentially mimic the range of induction strengths of receptor activation. After an 18 hour galactosidase induction, the fluorescent output of each of the strains was measured. Without a degradation tag, 121-fold repression was observed when expressing tetR with a high strength promoter (FIGS. 29 and 30). In contrast, low-level expression of tetR resulted only 20-fold repression in comparison to the control strain lacking tetR expression. The addition of a weak degradation tag (Ubi-M) displayed ranges of 1-73-fold repression when comparing low-high strength expression. The Ubi-Y degradation tag was only able to show low-levels of repression under high expression conditions, and Ubi-R did not show repression under any expression condition, due to the repressor being rapidly degraded. CPR strains, JGXX-3.0, have now been constructed.

Figure 31:
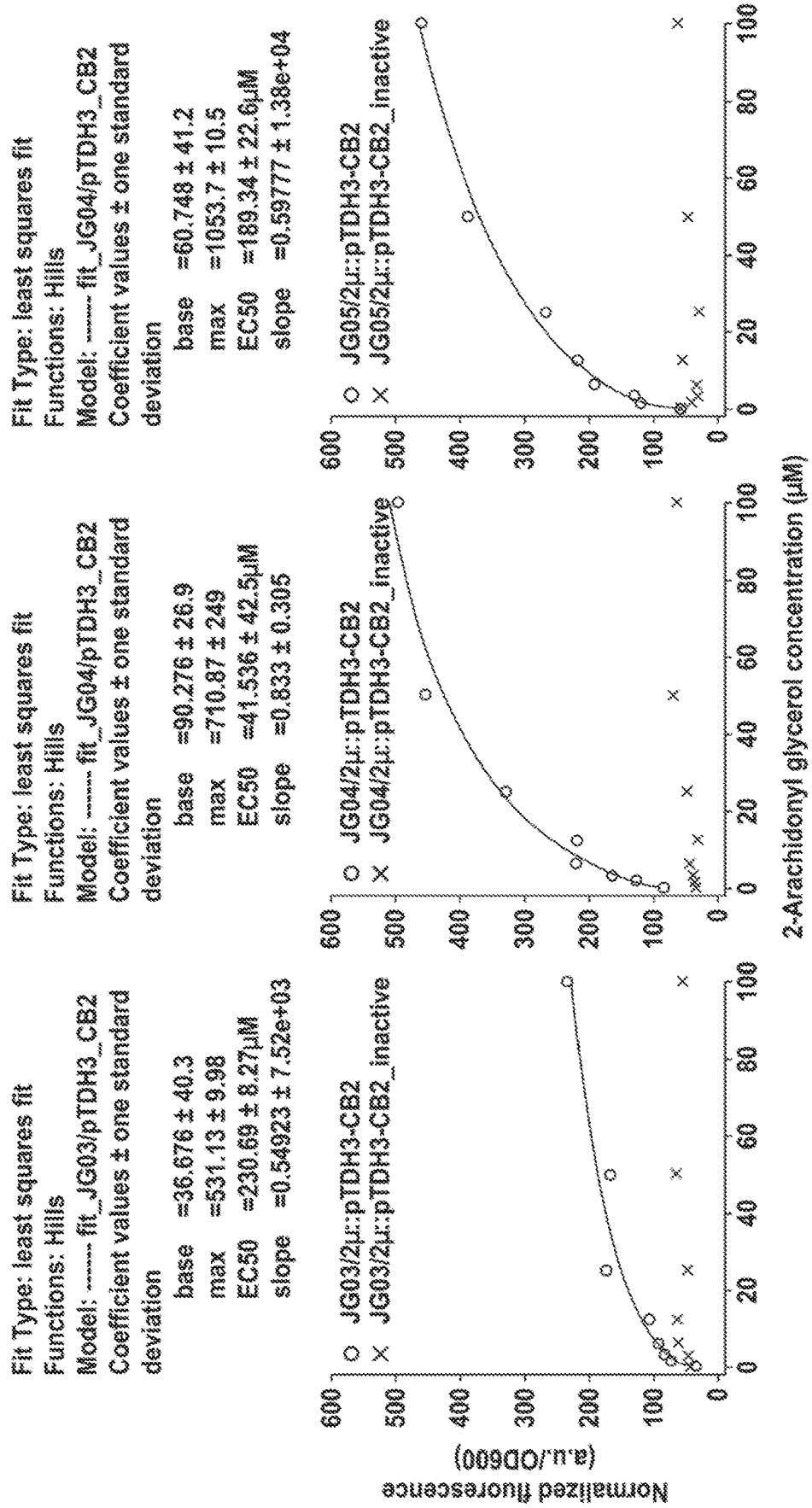
FIG. 31 shows dose response with native ligand. Dose-response of CB2 to 2-arachidonyl glycerol. Each point on the graph represents the average of replicate measurements. Strain JG04-2.0 was selected to be the preferred strain due to the superior EC50.

Functional Expression of Human CB2 and Autoactivation by Biosynthesis of β-Caryophyllene The ability of three of strains to couple to the human CB2 receptor expressed on a high-copy number plasmid was tested. Ga subunits that were predicted to couple to the receptor (Shim et al., 2013) were used. The dose-response of 2-arachidonyl glycerol, the native endocannabinoid, in strains differing only in the terminal 5 amino acids of the $G_\alpha$ protein. Control receptors were built that contained stop codons in the middle of the gene. These are referred to as 'broken' receptors. Using zsGreen1 as a reporter, each of the three strains was capable of responding to the ligand in a dose-dependent manner only in the presence of a fully functional receptor (FIG. 31). Strains containing broken receptors did not produce a signal at any concentration tested.

Figure 32:
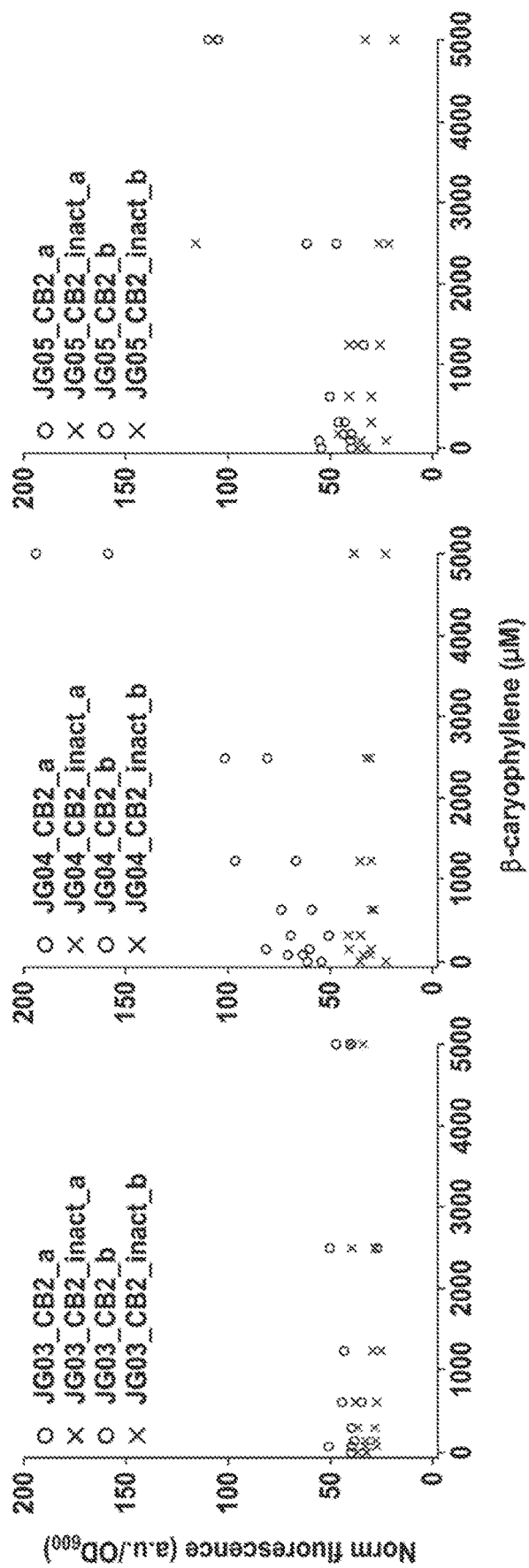
FIG. 32 shows dose-response of CB2 to β-caryophyllene. Each point on the graph represents the average of replicate measurements. We later found that our standard was mostly a degradation product, possibly explaining the large amounts of β-caryophyllene needed to activate the receptor.

A powerful pathway engineering method involves coupling the biosynthesis of a compound to a CPR circuit using a GPCR. This allows for the directed evolution of the pathway as well as the organism with the addition of more complex CPR circuitry. It was found that JG04-2.0 and JG05-2.0 both responded to high concentration of β-caryophyllene (FIG. 32).

To produce β-caryophyllene in yeast, the native isoprenoid pathway for the production of farnesyl diphosphate (FPP) was augmented by the heterologous expression of QHS1 β-caryophyllene synthase from A. annua. To increase yields, the UCP2-1 transcription factor was inserted to upregulate expression of enzymes HMG-CoA synthase (ERG13), mevalonate kinase (ERG12), and phosphomevalonate kinase (ERG8).

Figure 33A:
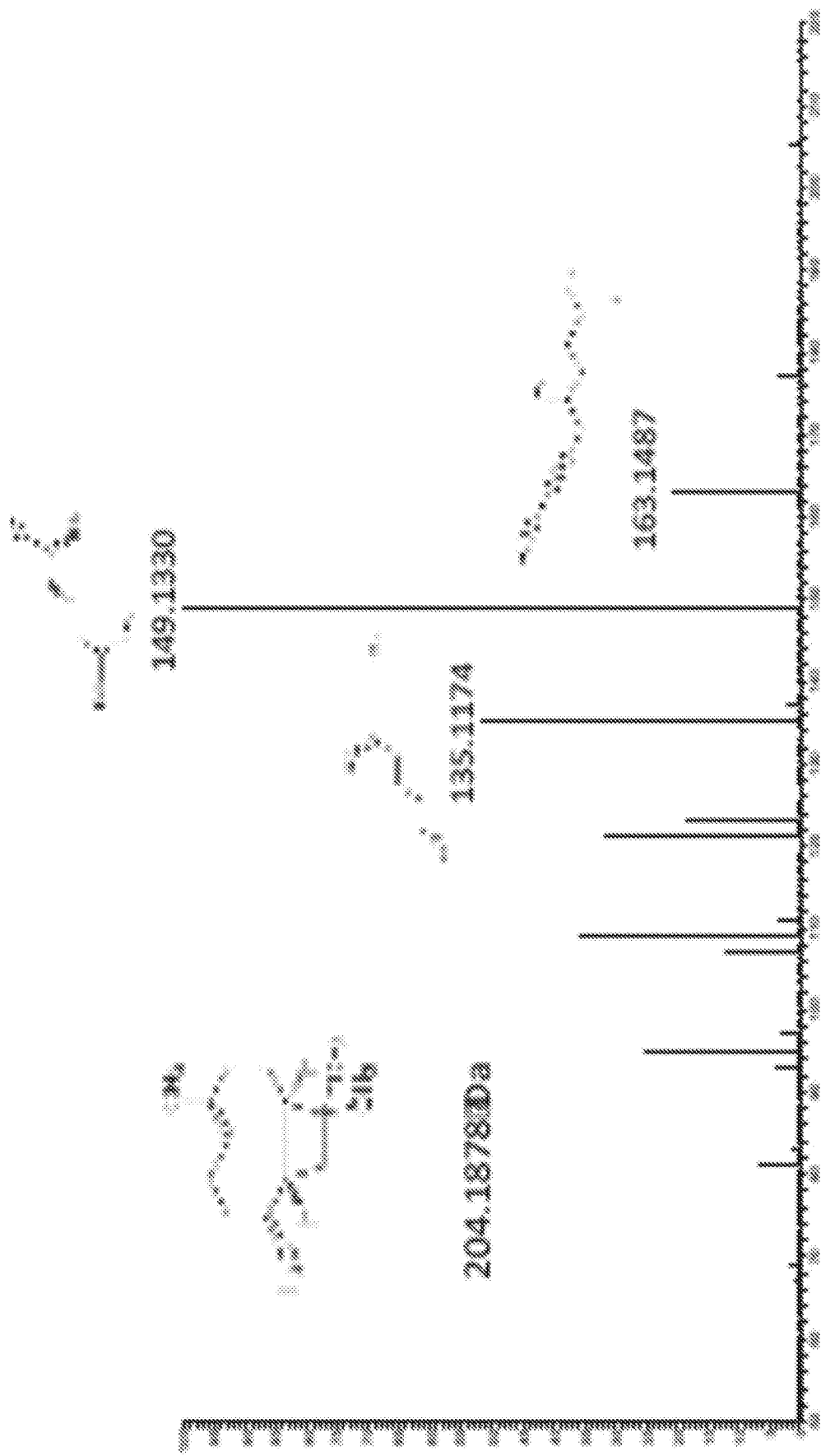
FIGS. 33A and 33B shows MS ANALYSIS OF β-caryophyllene production.
Figure 33B:
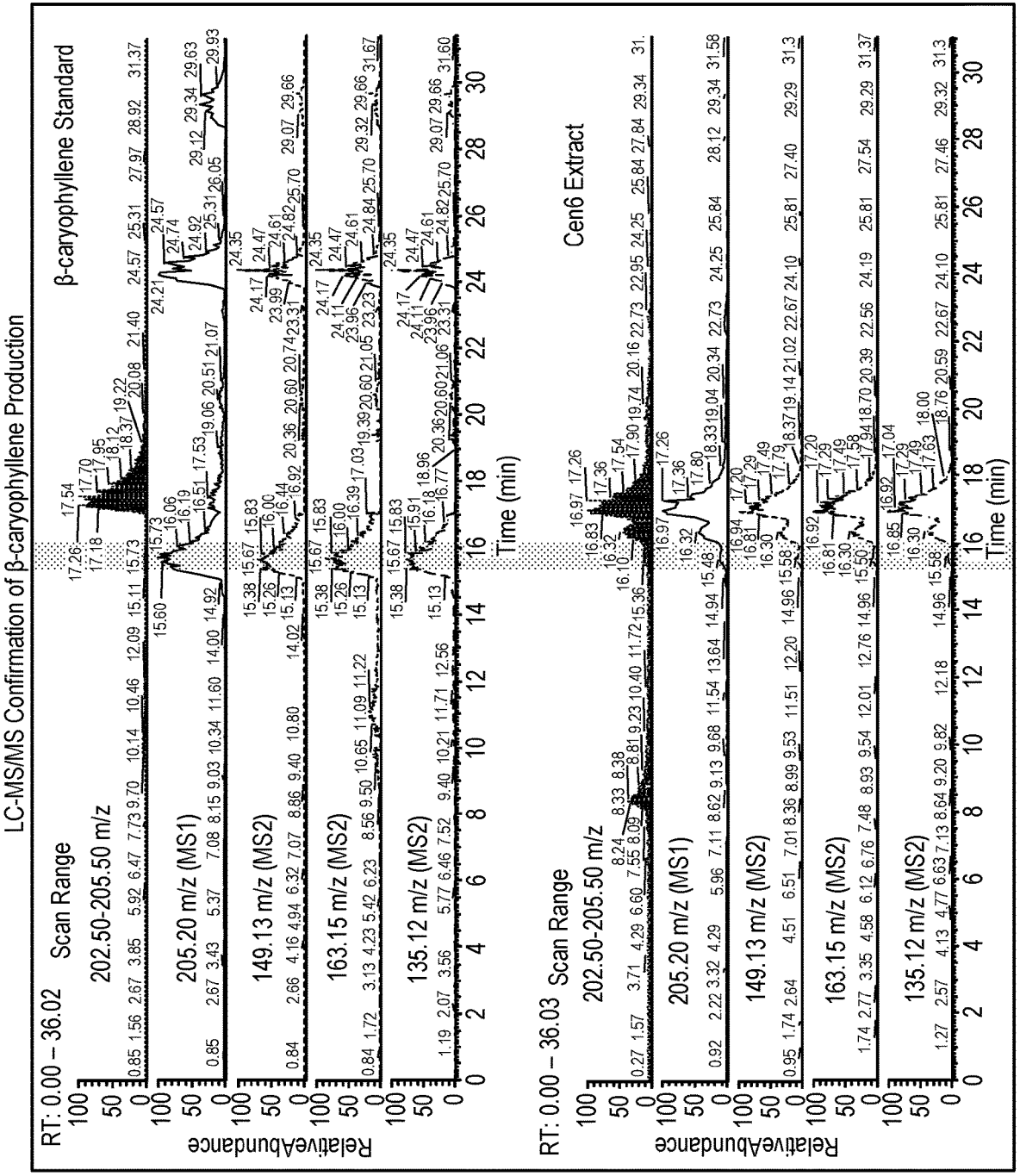

In addition, extra copies of the enzymes isopentenyl diphosphate isomerase (IDI1), the truncated HMG-CoA reductase (tHMG1), and farnesyl diphosphate synthase (ERG20) were constructed into expression vectors. Fragmentation mass spectrometry of extract was used to validate production (FIG. 33). Next, β-caryophyllene production vectors were inserted into a GPCR strain expressing the human CB2. When compared to a strain lacking the pathway, GPCR was activated with β-caryophyllene producing strains (FIG. 34). The pathway has been inserted into CPR strains (KOD reporter) to evolve the QHSI β-caryophyllene synthase.

Biosynthesis of Cannabidiol

The natural biosynthesis of cannabinoids in *Cannabis sativa* can be roughly divided into four distinct metabolic pathways: hexanoate, 2-C-methyl-D-erythritol 4-phosphate (MEP), geranyl diphosphate (GPP), and the penultimate cannabinoid production center. A total of 20 enzymes constitute the complete pathway; intermediates and flux relationships have been identified, providing a framework for alternative biological chassis development. The yeast *Saccharomyces cerevisiae* is an attractive organism in which to port the production of cannabinoids because many of the precursors needed are present, mitigating the need to recreate the pathway wholesale. Existing strains have been engineered to overproduce GPP, which reduces the complexity of the complete pathway from 20 enzymes to 10. Coupled with the ability to add hexanoate exogenously while still obtaining substantial levels of key intermediates, only 5 enzymes are left to optimize to create minimal cannabinoid production strains (Stout et al., 2012).

Figure 36:
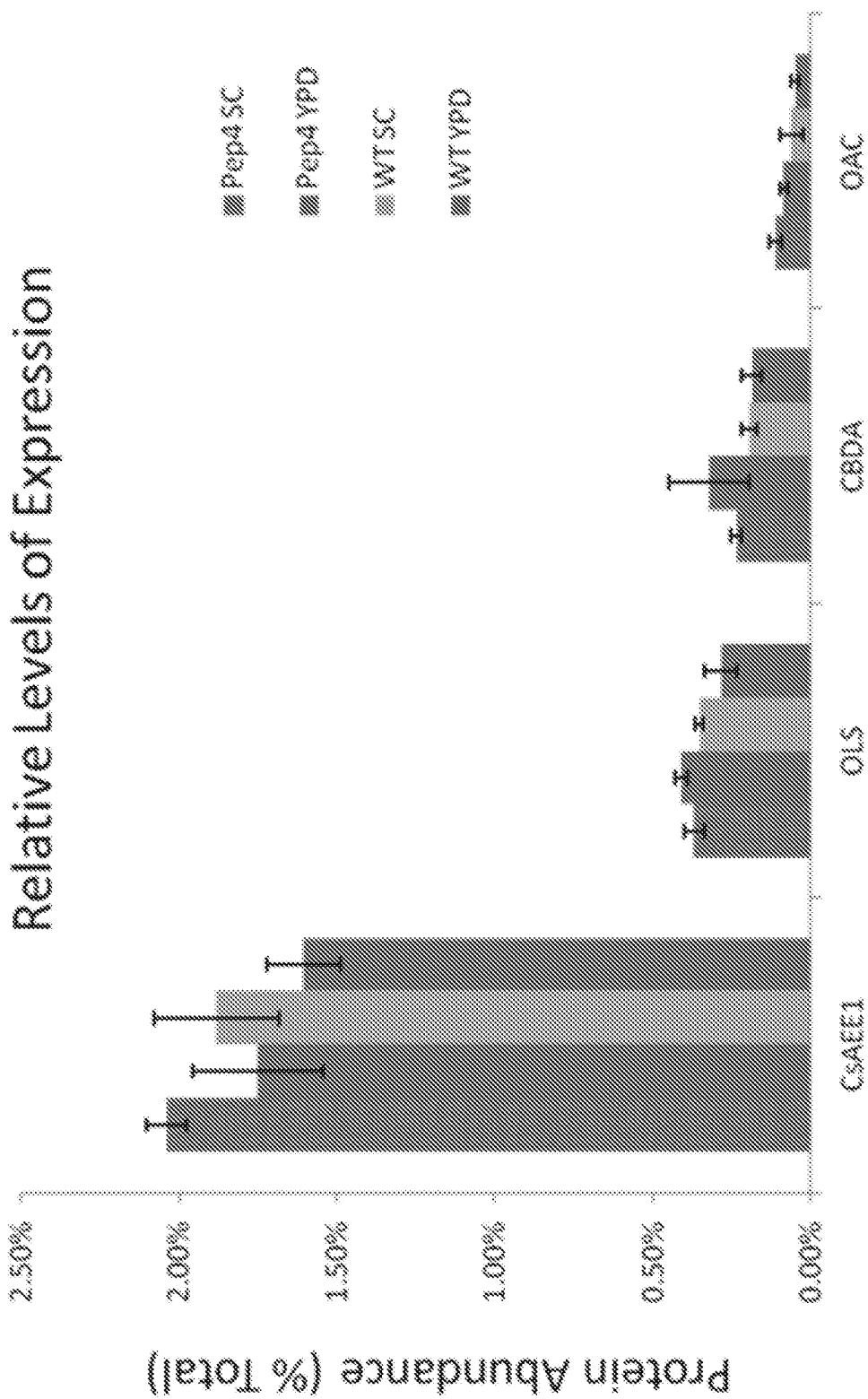
FIG. 36 shows protein abundance by strain. Relative abundance of each of the soluble CBD pathway enzymes are shown (A-D). Enzymes were expressed in BY4747 (wt) and ΔPep4 strains in both SC and YPD. Percentages are relative to total protein abundances from their respective strain and growth condition.

The genes for hexanoyl-CoA synthetase (CsAEE1), 3,5,7 trioxododecanoyl-CoA synthase (OLS), olivetolic acid cyclase (TKS), geranyl-pyrophosphate-olivetolic acid geranyltransferase (CsPTI), and cannabidiolic acid synthase (CBDA) were codon optimized for expression in *S. cerevisae*. These five enzymes were cloned under the control of endogenous yeast promoters: ScTDH3, ScCCW12, ScPGK1, ScHHF2, and ScTEF11, respectively. Promoters were chosen based on published expression profiles and kinetics (Table 7). Each enzyme was also given a unique terminator to mitigate the potential ejection of pathway enzymes via recombination. All five were assembled along with the Ura3 gene into a single integration vector via a restriction-digestion reaction and cloned into *E. coli* (DH10B). The complete pathway was stably integrated into the ΔUra3 locus of *S. cerevisiae* BY4741 and a BY4741 ΔPep4 knockout (FIG. 35). To determine if the enzymes were being produced, proteomics were performed and it was found that each of the cytosolic enzymes was present in great abundance (FIG. 36). A fluorescent reporter was fused and it was determined that the enzyme was expressed. There were no significant differences observed in protein abundance between BY4741 and the ΔPep4 knockout, leading us to continue with BY4741.

Figure 37:
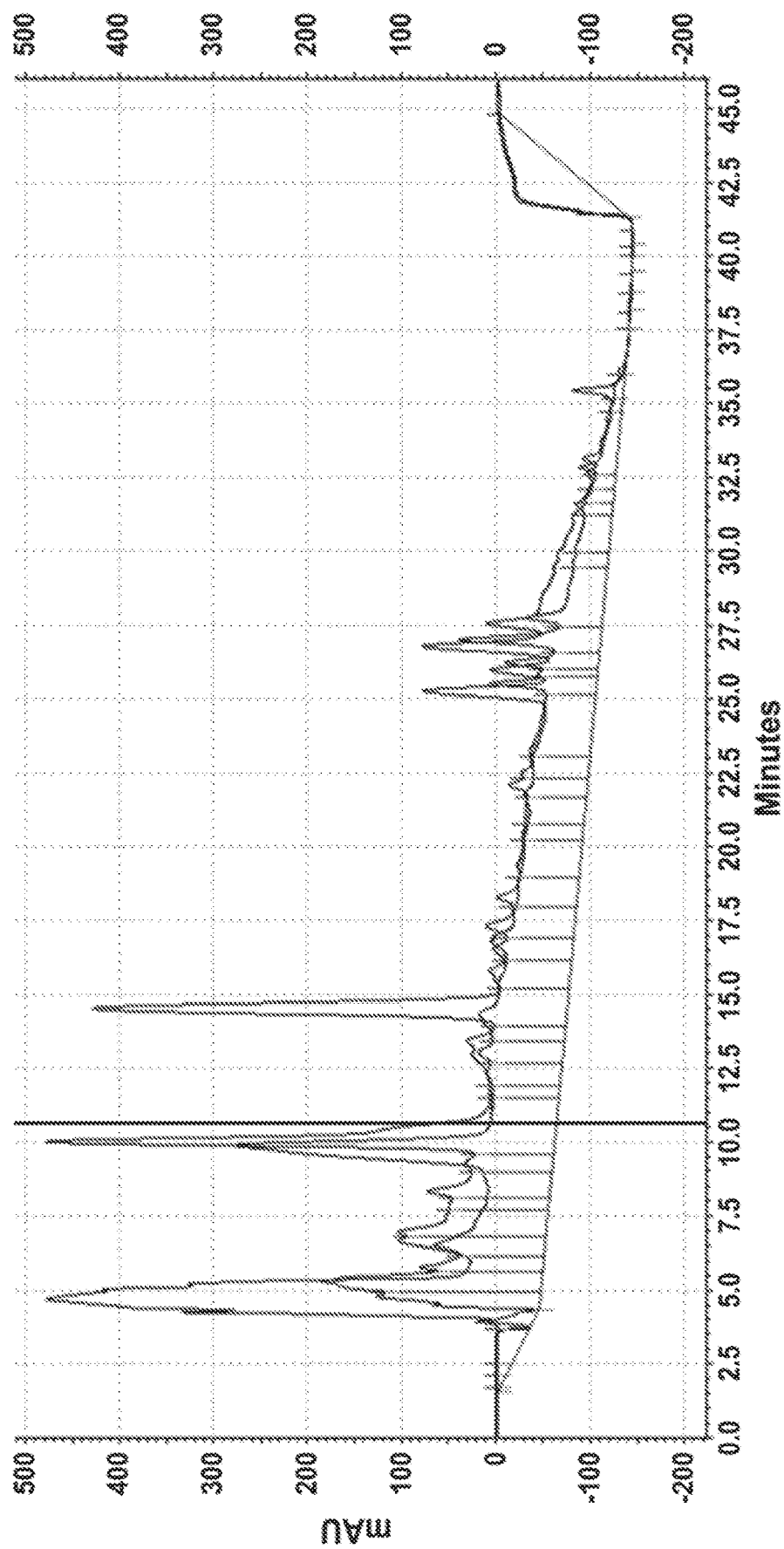
FIG. 37 shows HPLC of CBD from supernatant and cell pellets. Total ethyl acetate extractions from the supernatant as well as cell pellet are shown. CBD is primarily found in the cell pellet extraction (14.9 min peak).

Using this initial strain, CBD was produced with supplementation of 1 mM hexanoate in the growth medium after 7 days of growth. The production of CBD was confirmed by HPLC (FIG. 37). Control strains, lacking pathway enzymes at the URA3 locus, did not produce CBD.

Figure 38:
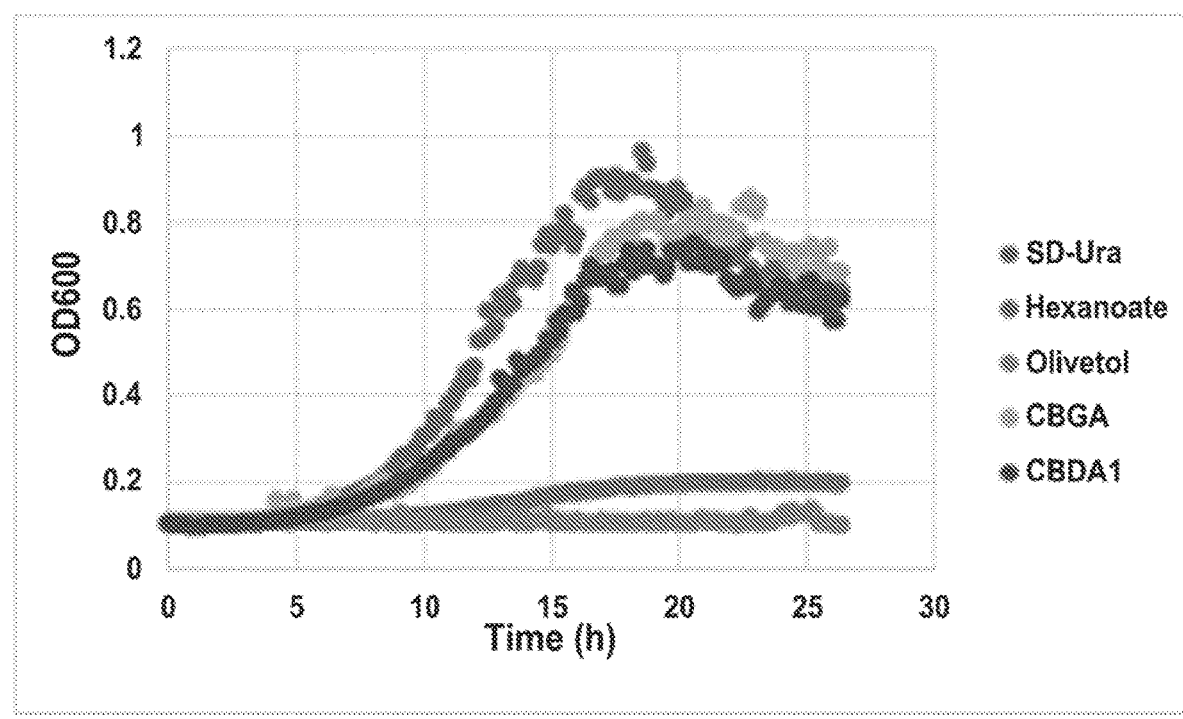
FIG. 38 shows metabolite toxicity determined by growth assays. BY4741 with a spacer sequence inserted into the URA3 locus were grown in 4 mM of each intermediate. Hexanoate and olivetol severely inhibit growth. CBGA and CBD were far less inhibitory when compared to growth in synthetic media only (SD-URA).

Growth assays were performed with BY4741 cells in the presence of each of the intermediates (FIG. 38). Hexanoic acid and olivetolic acid, the first two molecules in the pathway, were shown to strongly inhibit growth. CBGA and CBD were indistinguishable from one another. However, they produced a modest growth defect. From these data, it was concluded that growth would be a suitable surrogate for determining optimal conditions or guiding engineering efforts. Increasing the growth rate would likely correlate to the production of at least CBGA. Due to the abundance of CBDA synthase in the proteomics analyses, one would not expect the conversion of CBGA to CBDA to be problematic unless compartmentalization of enzymes caused partitioning.

Figure 39:
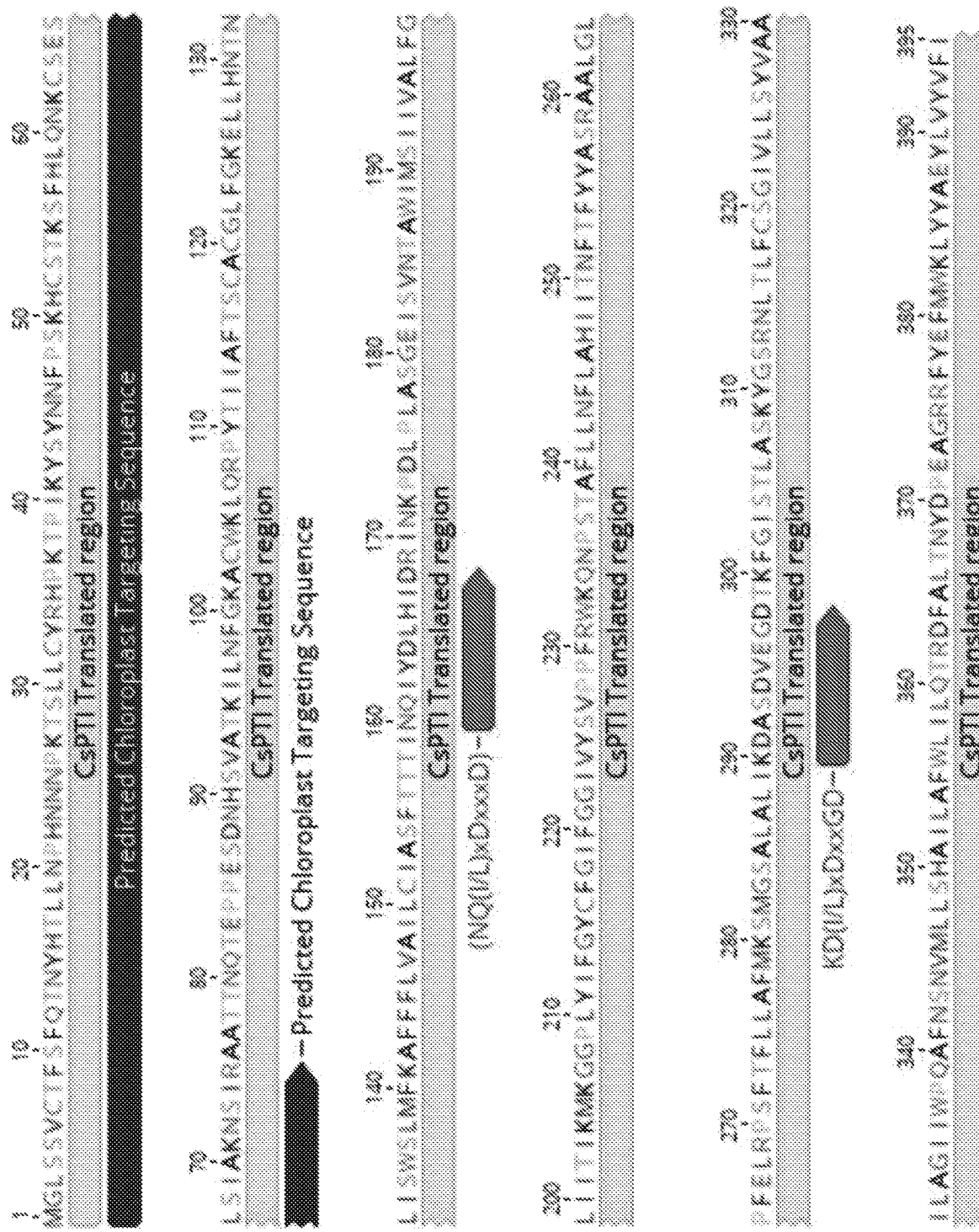
FIG. 39 shows predicted chloroplast targeting sequence by prenyltransferase. The SignalP and ChloroP-predicted signal sequence is depicted in black. The two common aromatic prenyltransferase active site loops are highlighted in pink.
Figure 40A:
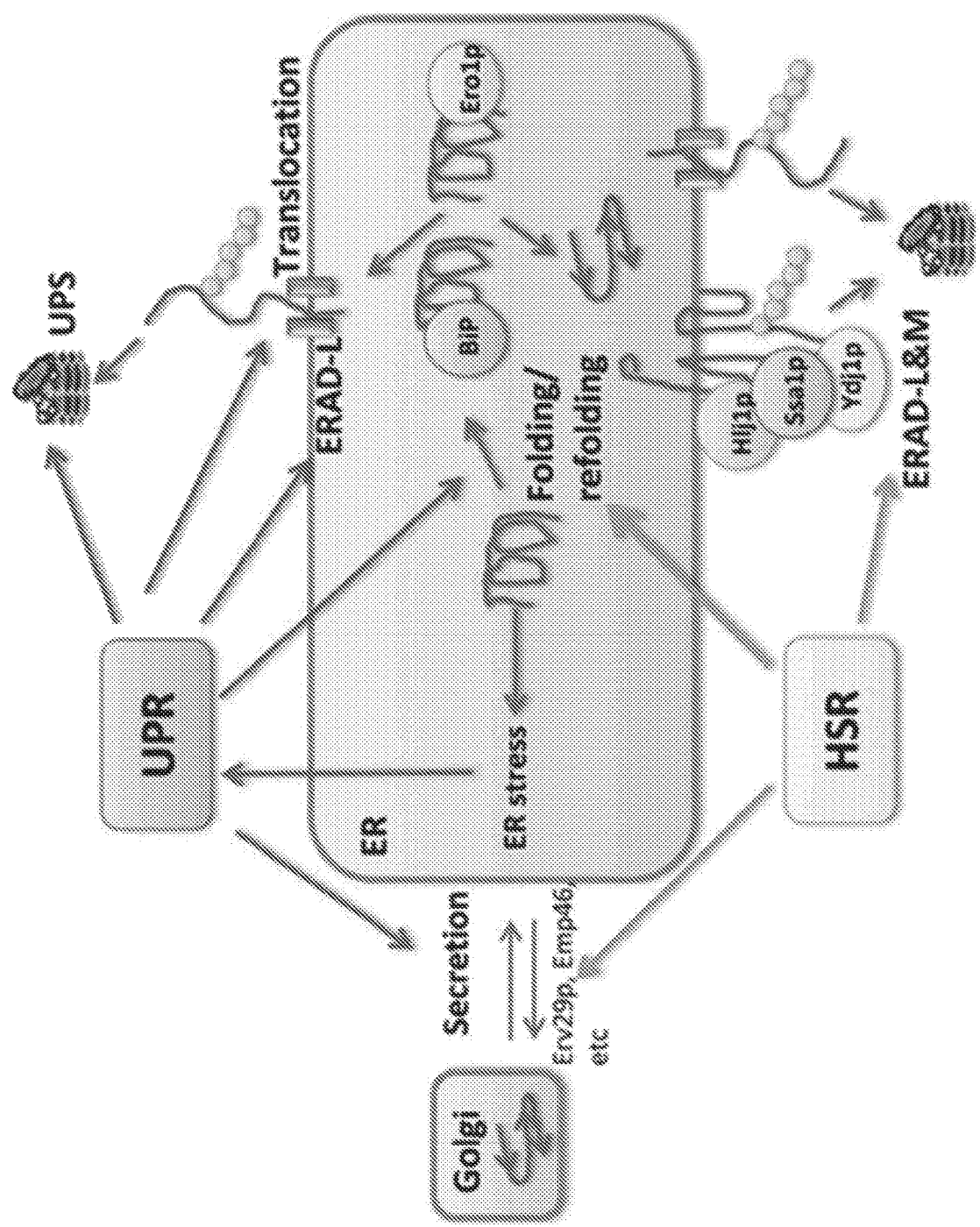

The inability to observe fragments of the aromatic prenyltransferase in the proteomics analyses and the strain's poor growth in hexanoic acid led to hypothesize that increasing the availability of the aromatic prenyltransferase would lead to robust growth and production of CBD. The aromatic prenyltransferase resides on the outer membrane of chloroplast in the plant. Using the bioinformatics tools TargetP and ChloroP, it was predicted that the first 74 amino acids of the integral membrane enzyme were a part of a chloroplast targeting sequence (FIG. 39), which yeast do not contain. The inability of the organism to interpret the plant signal sequence more than likely triggers degradation, which was observed in the upregulation of the unfolded protein response (UPR) in our proteomics experiments (FIG. 40).

Figure 41:
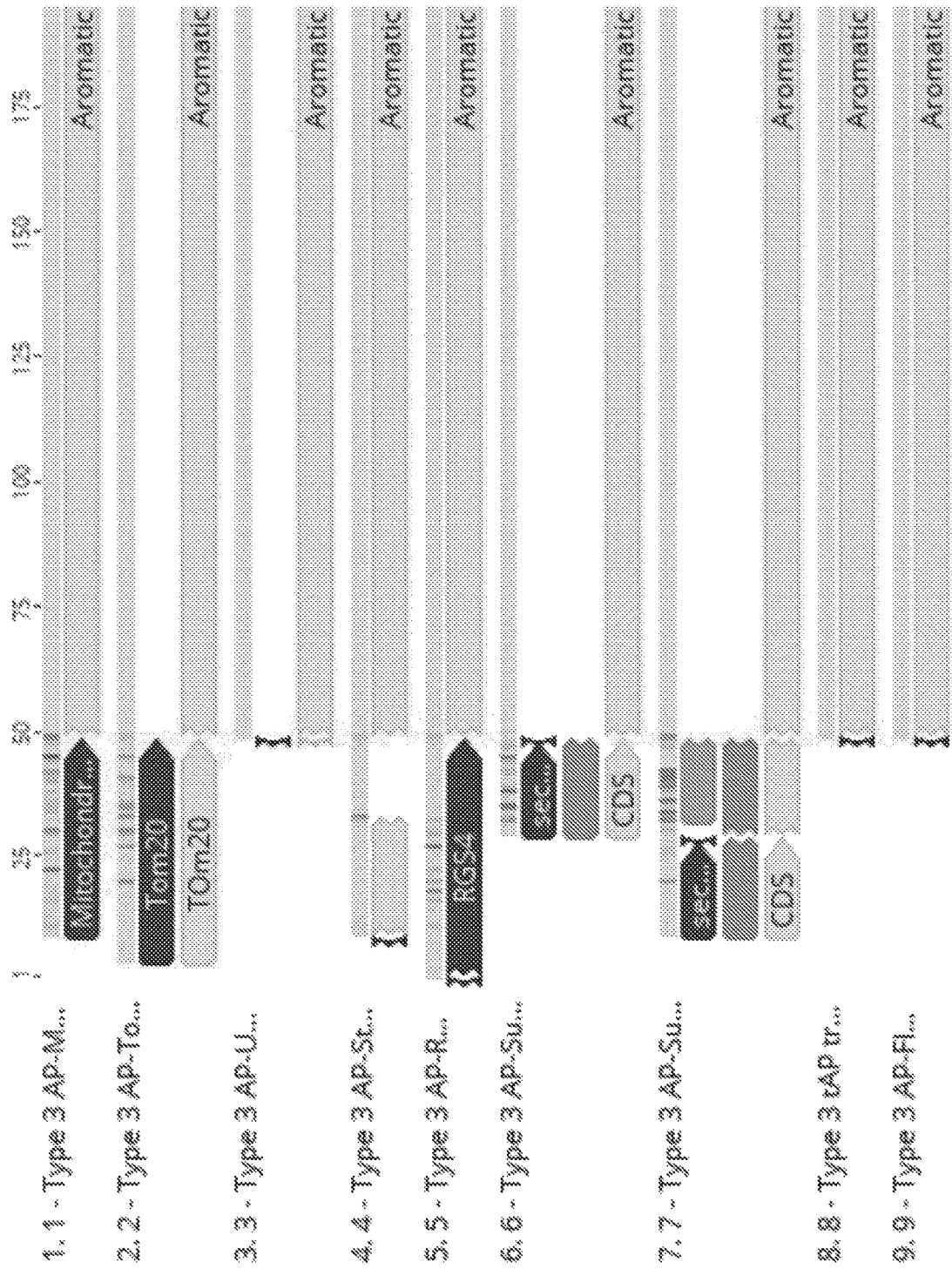
FIG. 41 shows rational design of prenyltransferase variants. For each of the designs, the predicted chloroplast targeting sequence was removed. 1-3 represent mitochondrial variants. 4-7 target the plasma membrane. 8 is the wildtype without the signal peptides, and 9 contains a C-terminal domain with the last 42 amino acids of Flo1p. This domain has been shown to anchor to the plasma membrane.
Figure 41:
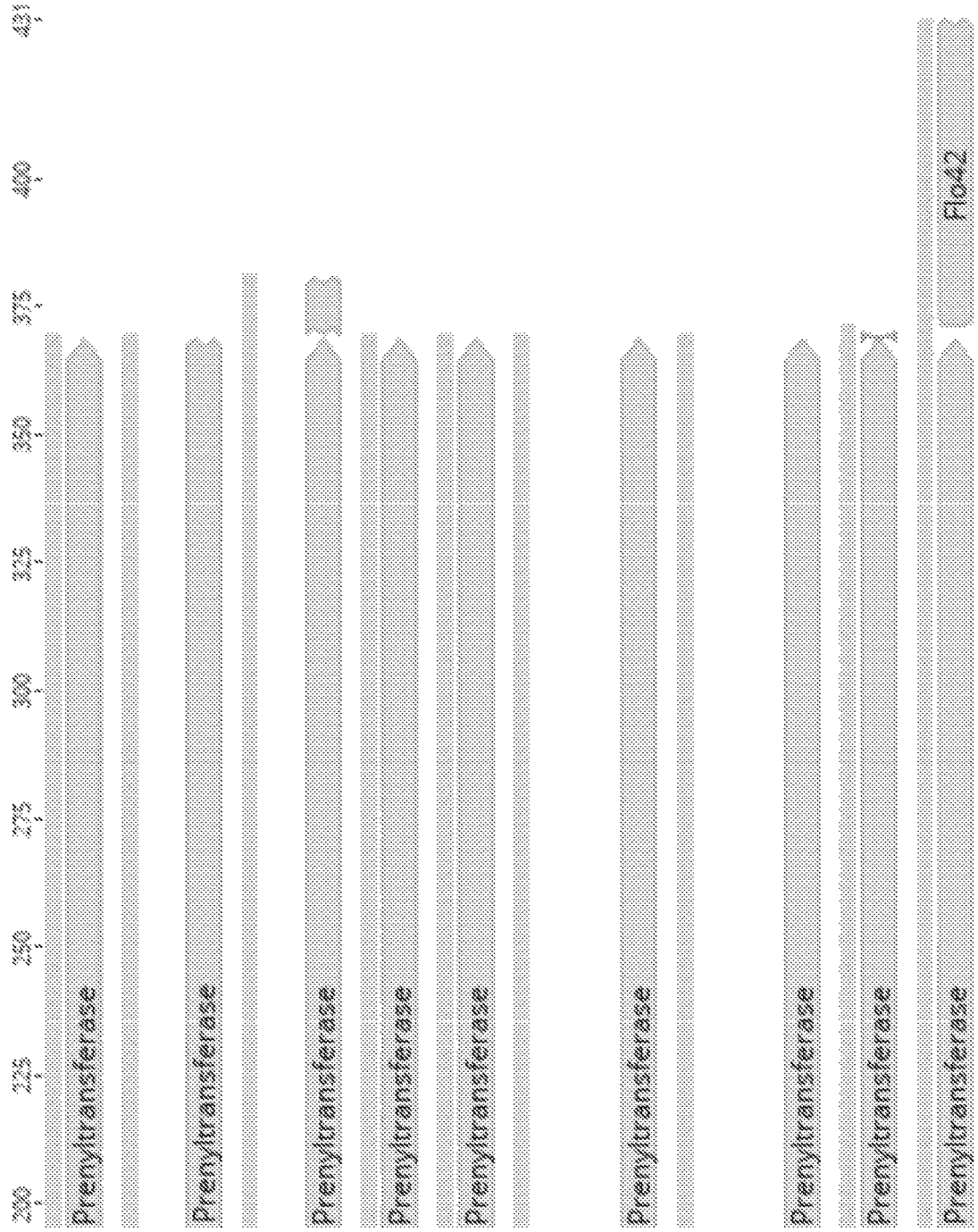

In an effort alleviate the growth defect and increase CBD production, a number of aromatic prenyltransferases variants were rationally designed. The inner mitochondrial membrane was targeted, the outer mitochondrial membrane, and the plasma membrane using common signal peptides and motifs (FIG. 41). Growth assays in hexanoic acid of these variants did little to distinguish optimal targeting of the aromatic prenyltransferase (FIG. 42).

Figure 43:
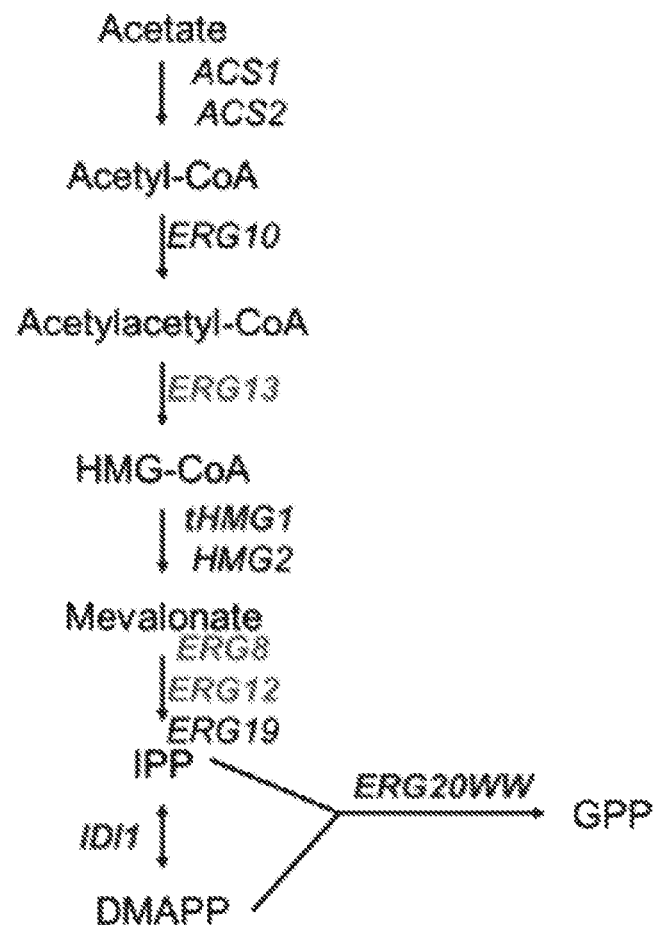
FIG. 43 shows the GPP pathway. The genes involved in GPP production from acetate in yeast are depicted. Additional enzymes added to CBD strains are depicted in red. Erg20WW is a mutant form of the native Erg20 and has been shown to primarily produce GPP. Enzymes shown in orange are upregulated with the addition of the mutant UPC2-1 transcription factor.

The two substrates for the aromatic prenyltransferase are olivetolic acid and GPP. Given that CsAEE1, OLS, and the OAC had all been shown to be functional in yeast cells and lysates (Gagne et al., 2012), it was concluded that the toxic molecule olivetolic acid was being made at this point. While yeast are able to synthesize GPP, it is in low abundance and a side product of Erg20, an essential gene in yeast that makes farnesyl pyrophosphate (FPP) as a part of the mevalonate and isoprenoid pathways. Others have shown that the expression of a mutant from of this enzyme (Erg20WW) can increase the amount of GPP available in the cell. With an additional copy of IDI1, a truncated HMG1 (tHMG1), and a mutant transcription factor (UPC2-1), large amounts of GPP can be produced in the cytosol of *S. cerevisiae* (FIG. 43) (Zhao et al., 2016).

Figure 44:
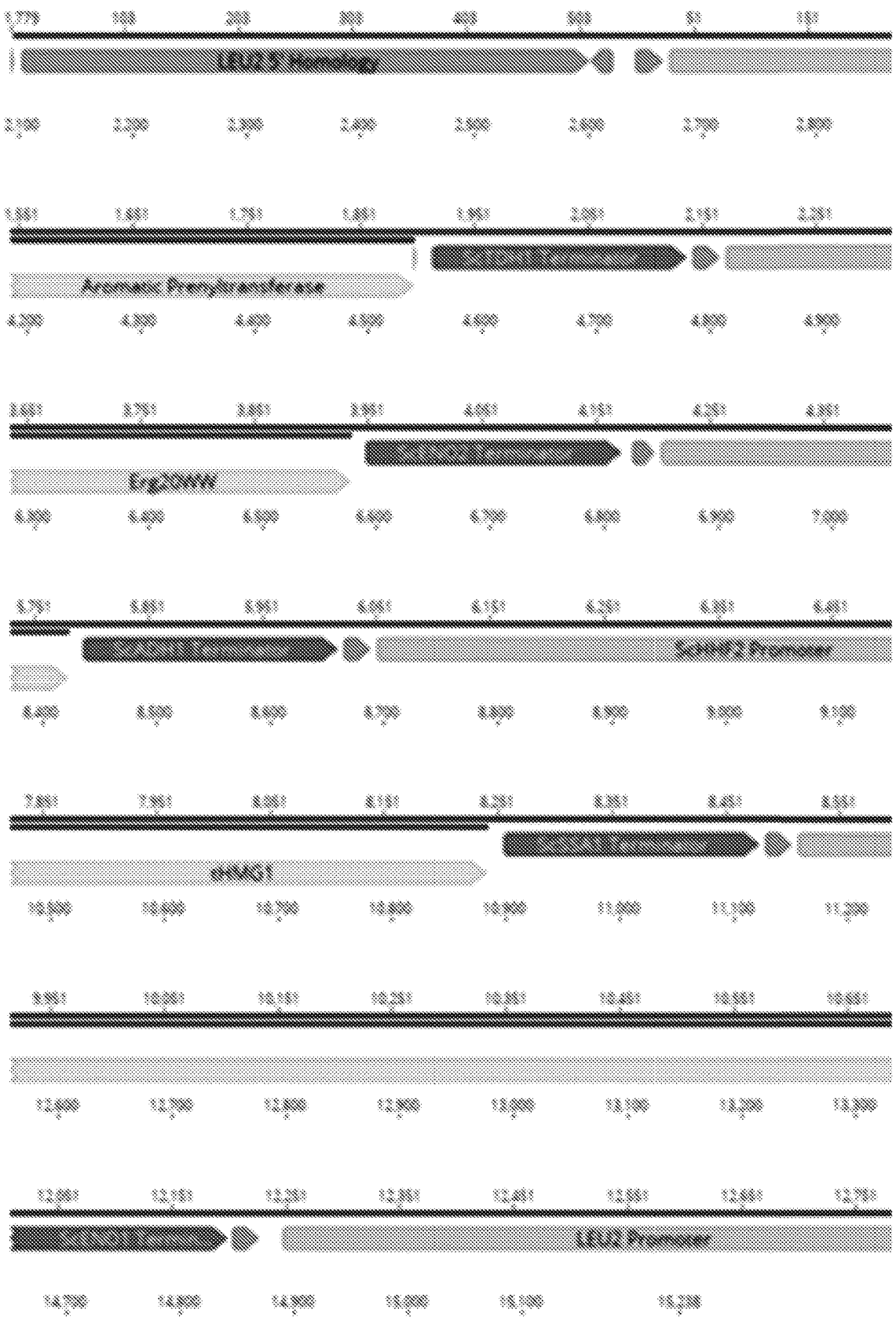
FIG. 44 shows an integration vector constructed to increase GPP. Pathway enzymes are shown in yellow. Promoters are green, and terminators are denoted in orange.
Figure 44:
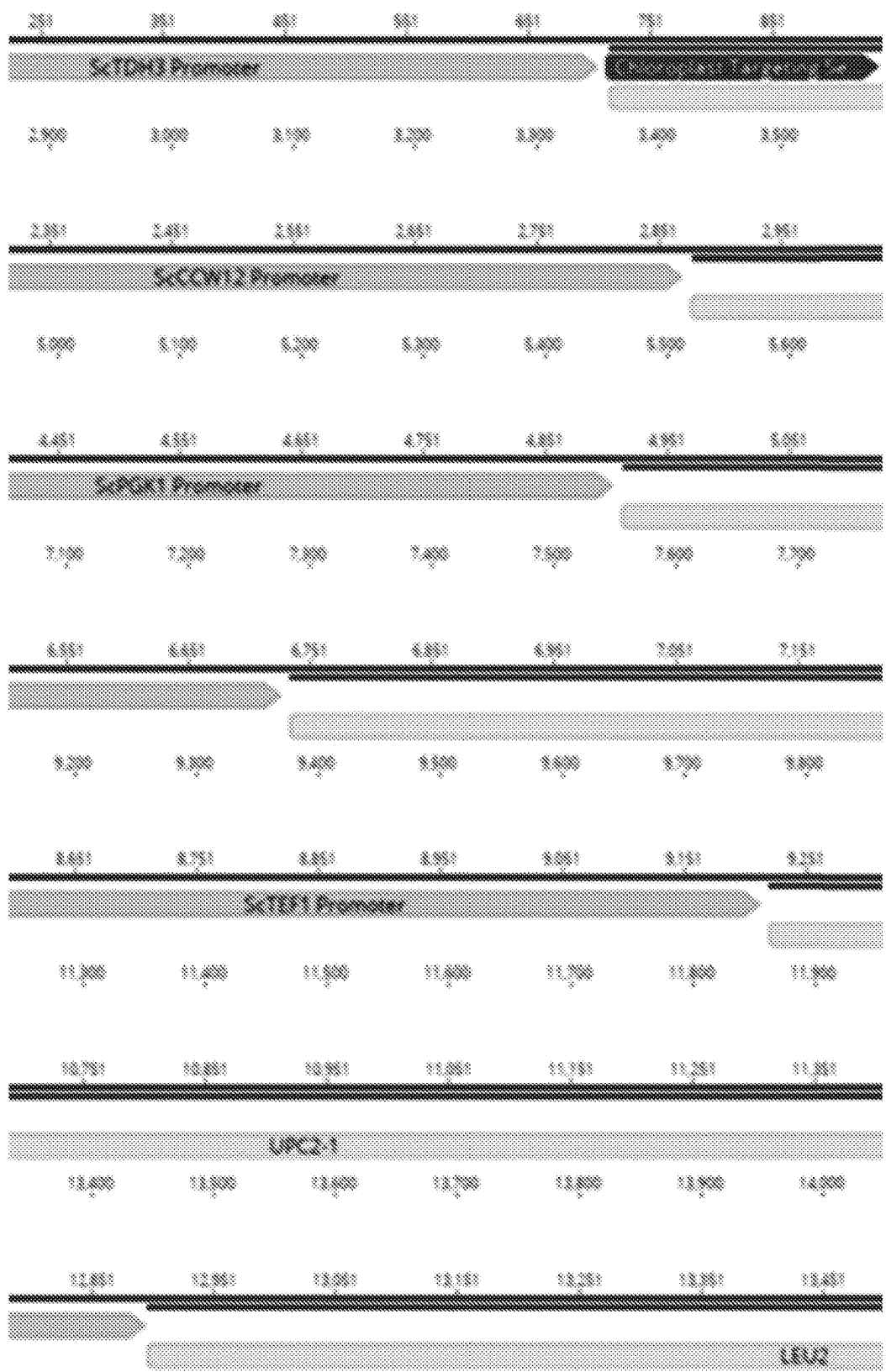
Figure 44:
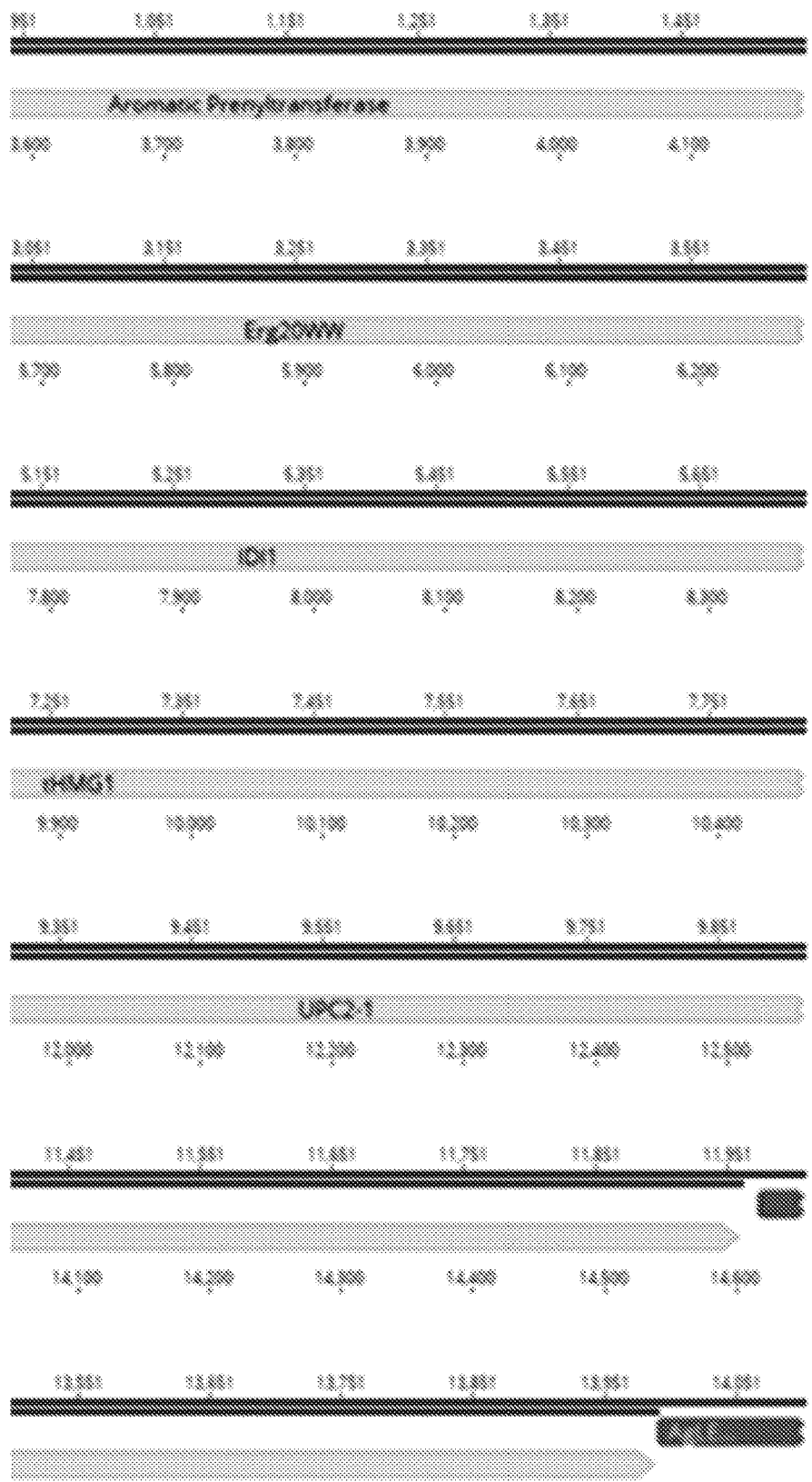
Figure 45:
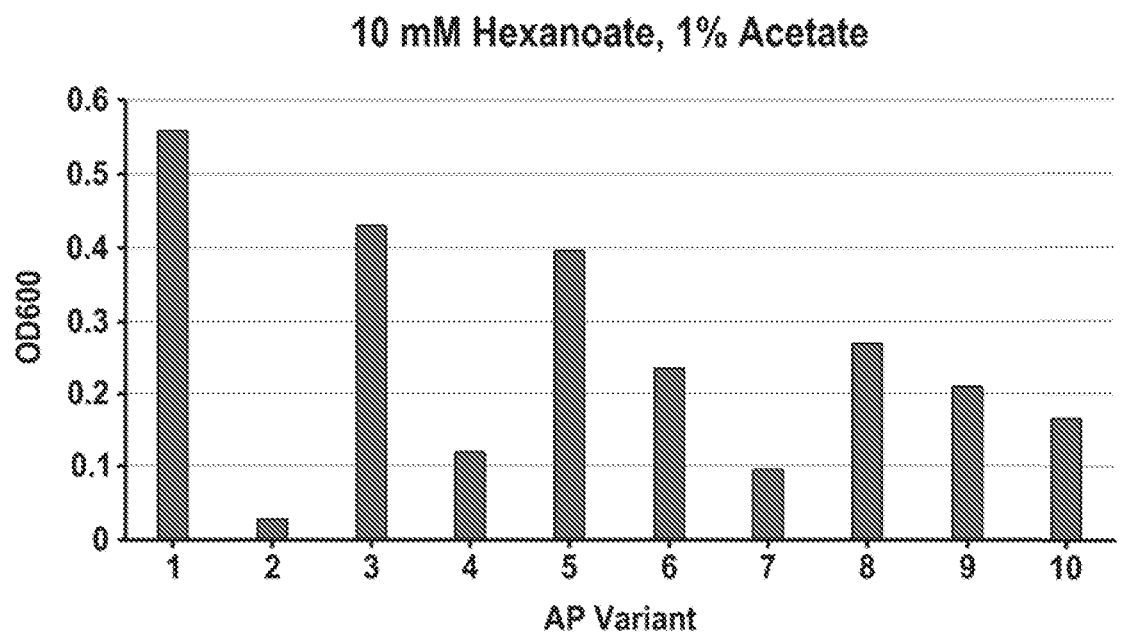
FIG. 45 shows increasing GPP enables robust growth in the presence of hexanoic acid.

It was reasoned that including these proteins along with an additional copy of the aromatic prenyltransferase might alleviate the growth defect if GPP was the limiting factor in growth assays in hexanoic acid. Integration vectors targeting the Leu2 and HO sites within BY4741 with each of the aromatic prenyltransferase variants being expressed under the control of the pTDH3 promoter (FIG. 44). Preliminary screening of strains harboring the CRC and GPP integration vectors in 10 mM hexanoic acid and 1% acetate revealed noticeable differences in growth (FIG. 45). These strains have subsequently been grown in 1 L batches.

The establishment of a robust CBDA-producing strain enables the production of other natural cannabinoids as well as the capability to further engineer pathways for more exotic, tailor-made molecules. Natural derivatives can result from plugging in key enzymes at pathway branch points. For example, CBGA is a common intermediate in the synthesis of CBCA, CBDA, and THCA. By replacing CBDAS with CBC synthase or THC synthase, CBC or THC can be readily accessed biosynthetically. Another natural branch point occurs upstream of olivetolic acid, which produces the shorter chain divarinic acid derivatives (CBDV, THCV, and CDCV). Additionally, a number of other cannabinoid branch points from *C. sativa* and other cannabinoid producing plants should be amenable to the plug-and-play platform to create a vast array of combinatorial variants. The addition of other hexanoate and GPP derivatives should provide yet another avenue to create novel compounds not otherwise found in nature.

The ability to examine signal transduction pathways in yeast further leads to the ability to identify drugs that can modulate signal transduction pathways. In this instantiation, a drug would be co-expressed with the pathway or added exogenously. Pathways for the production of small molecules can be co-expressed in yeast with a given GPCR or other signal transduction partner. The pathways lead to the production of drugs, some of which may activate (or inhibit) the GPCR. The production of cannabidiol, a 5HT1A receptor agonist and CB1/CB2 receptor antagonist, and β-caryophyllene, a CB2 receptor agonist, has been shown. By including primers that can amplify the pathways that created the small molecule, emulsion PCR can lead to the selective amplification of those pathways or pathway variants that produce the most functional effector molecule. Using CPR for drug-discovery should now be possible by creating libraries of human receptors and screening drugs in either the agonist or antagonist CPR circuits. This is an especially powerful technique when one considers the ability to screen for off-target hits in a high-throughput manner by sequencing activated or inactivated receptors.

Therapeutic Antibody Selections Using CPR

The ability to screen small molecules is only one possibility. Using CPR, one can select for human antibodies that activate (Agonist CPR) or inactivate (Antagonist CPR) GPCRs. To do so, libraries of antibodies can be co-expressed in GPCR-expressing strains. Rather than tethering the antibody to the outside of the cell, as done in yeast display, antibodies are anchored inside the periplasmic space with a GPI-domain fusion (Flo42). Preliminary experiments with the human Glp1R using a fluorescent reporter suggest that this may be possible. Antibodies that can activate a given GPCR will lead to the production of the DNA polymerase, which leads to amplification of the antibody variants capable of triggering the receptor. The implementation of the inhibitory pathway requires the inverter circuit, in which the repression of a repressor led to KOD polymerase production. This method of antibody discovery is especially important since therapeutic antibodies identified will be identified not only on basis of the strength of interaction (affinity), but also on functionality, such as whether the antibody is an antagonist or agonist of the GPCR. Such functional selections cannot be carried out in almost any other way and would mark the first directed evolution platform capable of producing human therapeutic antibodies.

Methods & Materials

GPCR Strain Creation and Genetic Manipulation

Strains BY4741 and BY4741ΔGal2 were obtained from the Marcotte laboratory. Cas9 plasmids were constructed as previously described (Lee et al., 2015). To cure the Cas9 plasmid, we patch plated 15 colonies that were grown on rich media. Human receptor sequences were procured from Uniprot, codon optimized for expression in *S. cerevisiae*, and ordered as GeneBlocks from IDT. Entry vector stocks (YTK001) were made to allow for shuttling between integration, low-copy, and high-copy plasmids. Promoters and terminators were taken from the Yeast Toolkit. A list of GPCR strains is contained in Table 6. The copy number of receptor plasmids are indicated where necessary. Integration vectors were digested with NotI. All transformations were done using the EZ Yeast Transformation Kit (Zymo Research). For pathway engineering, vectors were constructed with the same procedures. Plasmid maps and sequences are available upon request.

Dose-Response of Human Receptors Expressed in Yeast

For 5HT1A, overnight cultures of receptor transformants of JG05-2.0 and JG05-0.2 were washed and diluted 1:1000 in media containing varying amounts of serotonin. Cells were washed 3 times and resuspended in PBS. Fluorescent (485 nm/515 nm) and cell density (600 nm) measurements were taken on a Cytation 5. Data were plotted and analyzed using SigmaPlot10. For CB2, strains JG03-, JG04-, and JG05-2.0 were transformed and treated the same. Broken receptor (stop codons) were also included in these assays.

CPR in Yeast

JG05-1.0-5HT1A were grown overnight and diluted into media containing 250 μM serotonin. Control cells were not induced. Cells (3 mL total) were collected after 18 hours of induction and spun in a tabletop centrifuge at 3,000×g for 5 minutes. The supernatant was discarded and the cell pellet was washed in water and then resuspended in 1 M sorbitol, 25 mM EDTA, 50 mM DTT. Cells were collected again and washed in 1 M sorbitol. After another wash with water, cells were resuspended in 500 μL PCR mastermix (pH 8.0 or pH 8.8). The resuspended cells were placed into a 2 mL tube with a 1 mL rubber syringe plunger and 1200 μL of oil mix (876 Tegosoft DEC, 84 Gransurf W9, and 240 μL light mineral oil (Sigma-Aldrich)). The emulsion was created by placing the cell and oil mix on a TissueLyser LT (Qiagen) with a program of 37 Hz for minutes. The emulsified cells were incubated at 37° C. for 15 minutes, followed by 10 minutes at 95° C., and then thermal-cycled for 35 cycles (Appendix II). Emulsions were broken by spinning the reaction (20,000×g) for 15 minutes, removing the top oil phase, adding 750 μL chloroform, vortexing vigorously, and finally phase separating in a phase lock tube (5Prime). The aqueous phase was cleaned using a Promega PCR purification column. Products of the CPR amplification were visualized using agarose gel electrophoresis.

Proteomics Analysis

Cells harboring pathways or empty integration vectors were grown at 30'C for 24-48 hrs in selective media and diluted 1:25 for 6 hours. Cell pellets were collected by centrifugation and given to the Marcotte laboratory for analysis. Dr. Dan Boutz performed all of the proteomics experiments.

Metabolite Toxicity and Growth Curves

BY4741 transformed with a spacer sequence at the URA3 locus were grown for 48 hours and diluted 1:25 in media containing 4 mM of each metabolite (hexanoate, olivetol, CBGA, and CBD). Measurements of cell density (OD600) were taken in 10 min intervals. Each condition was tested in triplicate. For hexanoate growth conditions of aromatic prenyltransferase variants, transformed cells were seeded for 48 hrs and diluted 1:25 in 96-well grow-blocks in media containing 1-5 mM hexanoate. Measurements of cell density were taken in 24 hr intervals using an F500 plate reader. Final screening was performed with 10 mM hexanoate, 1% acetate supplemented synthetic complete media in 50 mL culture volumes.

Metabolite Extraction and Analysis

Supernatant and cell pellets were extracted with 40 mL ethyl acetate, dried under vacuum and resuspended in 250 μL ethanol or methanol. To decarboxylate metabolites, resuspensions were incubated at 65° C. for 24 hrs on a tabletop incubator. 200 μL of the decarboxylated product was then run on a C18 column equilibrated with 25% water, 75% ACN, 0.1% TFA. Metabolites were eluted along a gradient with 100% CAN, 0.1% TFA. Standards were run after samples. We recorded the full spectrum between 0-600 nm and monitored 228 nm for CBD production. Chromatograms were produced and analyzed within the Beckman System Gold 32 Karat software package.

Example 6: A Robust Ionotropic Activator for Brain-Wide Manipulation of Neuronal Function Disclosed herein are methods for the rational design, directed evolution, and characterization of novel neuronal actuators based on the purinergic P2X receptor. For nearly a decade, analysis of brain circuitry has relied on methods that allow neuronal activity to be perturbed in an intact brain with cell type-specificity. Genetically-encoded neural actuators have ranged from chimeric G-protein coupled receptors (GPCRs) with orthogonal ligands to light-gated ionotropic channels. While these tools have helped uncover cellular substrates of cognitive and behavioral states, significant limitations remain. Optical fiber implantation is destructive, and illumination is limited by mechanical constraints and the requirement that the target site be identified in advance. GPCRs are often inefficient, display poor temporal control, and often produce long-term functional changes in neurons. Disclosed herein are computational and directed evolution methods needed to engineer a neuronal activator that embodies the strongest features of existing approaches, ligand-dependent gating of a channel with high unitary conductance and a negligible desensitization profile. Disclosed is the computational work, the functional expression of P2X subtypes in yeast, and validation of CPR selection components that lead to the engineering of orthogonal receptor:ligand pairs. Also discussed is the development of a drug screening platform using yeast to express P2X receptor subtypes.

The ability to manipulate defined neuron populations has revolutionized in vivo investigations of brain circuitry (Alexander et al., 2009; Boyden et al., 2005; Zemelman et al., 2002). The main requirement for a genetically encoded neuronal actuator is that it normally be absent from the central nervous system, so that only neurons expressing the actuator are sensitized to an orthogonal ligand added in trans. While many actuators that stimulate or silence neurons have been devised, each has its own set of drawbacks, providing a significant opportunity for improvement. Building on lessons learned from modeling and directed evolution, disclosed herein are strategies for the engineering of orthogonal receptor:ligand pairs that can enable restricted activation of neurons. Based on the P2X nucleotide receptor, this activator can incorporate the strongest features of existing tools, while avoiding many of their limitations.

There are two varieties of actuators: (1) pharmacogenetic, such as metabotropic G-protein coupled receptors (GPCRs), and (2) optogenetic, mostly ligand-gated ion channels. Hence, actuator triggers have been either small molecules or pulses of light. For in vivo use, light delivery is inefficient and requires potentially destructive optical fiber implantation. In this respect, pharmacogenetic tools have an advantage over optogenetic ones: (1) neurons of interest may be distributed throughout the brain, making optical methods impractical; and (2) cell locations may not be known ahead of time. However, while systemically administered small molecule ligands can theoretically reach sensitized neurons throughout the brain, they must cross first cross the blood-brain barrier. In addition, GPCRs are more difficult to regulate, but can be induced for hours; meanwhile, ionotropic channels offer precise temporal control, but are inadequate for long-term activity management either due to rapid desensitization or because the required ligand is metabolized. Currently, the most widely used actuator is channelrhodopsin2 (Chr2), a light-gated algal cation channel (Nagel et al., 2003). The tradeoff for its very rapid on/off kinetics is poor single channel conductance (estimated at 150 fS) and fast desensitization. These features have limited the use of Chr2 for prolonged or localized stimulation, such as of axonal fibers and terminals.

The functional mapping of neuronal circuits in the brain can be performed anatomically or behaviorally. For anatomical circuit analysis, it is necessary to choose an initial population of neurons within a brain region of interest and sensitize those neurons to activation. Genetically encoded activators that are otherwise absent from the central nervous system can be targeted to a selected subset of neurons using spatially confined viral infection and cell type-specific promoters. When the neurons are subsequently stimulated, their post-synaptic partners can be identified on the basis of elevated activity, using post hoc staining for elevated immediate-early gene (IEG) products (Bahrami and Drabløs, 2016), or in transgenic animals where IEG activation is coupled to the synthesis of a fluorescent protein tag. In both instances the pre- and post-synaptic neurons become labeled. Behavioral circuit mapping relies on a change in animal performance (DiBenedictis et al., 2017; Krakauer et al., 2017). Stimulation or silencing of cells in an anatomical domain produces a measurable behavioral outcome. When the manipulation is regional, akin to a lesion, cell types contributing to task performance cannot be readily deduced. When the activity of defined cell types is perturbed and a behavioral phenotype detected, inferences can be made about cell function.

In both cases, experimental success is predicated on the efficiency of cellular perturbations. In direct circuit mapping, post-synaptic neurons will not be detected if the stimulus is too weak. Likewise, a behavioral change may not be apparent when the target cell population is only partially affected. As a result, pharmacogenetic methods have a slight advantage over optogenetic ones: (1) light guides produce spatially restricted illumination, potentially missing many cells of interest, and can damage neuronal connections—both drawbacks for behavioral analyses of cell function; (2) where the experimental readout is optical or the behavioral assay incorporates a visual component, light stimulation can confound outcomes; and (3) optical methods are often hampered by low conductances and rapid desensitization. Likewise, pharmacogenetic techniques that rely on neuromodulatory second messenger cascades can increase the sensitivity of pre-synaptic neurons to stimulation, but may not reliably activate their post-synaptic partners. Finally, for both pharmacological and optical methods, control over multiple, potentially intermingled cell populations has proven elusive.

A family of pharmacogenetic ionotropic activators addresses the enumerated limitations listed above. The absence of a light requirement ensures comprehensive stimulation of sensitized neurons irrespective of their location; the gating of a non-specific cation channel produces rapid membrane depolarization followed by sustained cell firing; and the availability of multiple actuators that can be used in parallel provides experimental access to several cell populations.

An activator based on the P2X receptor represents the ideal alternative for robust and selective stimulation of neurons. P2X channels support currents of 10-20 pS (exceeding that of Chr2 by nearly 100 fold). Stimulation is tunable, controlled by ligand concentration. Several members of this receptor family (P2X2 and P2X4) display negligible desensitization. Nucleotide analogs can be administered systemically or fitted with a photolabile caging group to enable localized activation using visible light (Zemelman et al., 2003). Their stability can also vary, regulating stimulus duration. Since P2X receptors are abundant in the central nervous system, it is necessary to design synthetic variants of P2X, based on published crystal structures, along with matching ligands. These modified P2X receptors will be unresponsive to endogenous nucleotides, but instead be controlled by the orthogonal small molecule ligands. Fundamentally, three main tasks must be accomplished to effectively control neurons with the resulting orthogonal receptor-ligand pairs: (1) validation of the disclosed computational methodology in the design of receptors and agonists; (2) optimization of conditions for the directed evolution of receptors; and (3) ensure orthogonality of engineered channels and small molecule ligands before functionally testing them in an organism.

Using structural information of P2X4, candidate mutagenesis sites and designs for complementary ligands are discussed. By extending the directed evolution technique, Compartmentalized Partnered Replication (CPR), to yeast, there exists a platform to engineer orthogonal purinergic receptor-ligand pairs in parallel with a computational approach. Using alternating rounds of positive and negative selection, libraries that converge on a small number of unique solutions for each new ligand can be used.

Medicinal and computational chemists have developed virtual tools for in silico screening of compounds against targets of interest and algorithms for guiding small molecule design based on structure-activity relationships (Doupnik et al., 2015; Giacomini et al., 2015). Quantitative structure activity relationship (QSAR) data are then used to build numerical models for predicting and interpreting experimental results. Refinement by computational fragment-based drug design has also garnered experimental support for use with receptors and enzymes (Bohm et al., 1999; Mueller et al., 2002; Stürzebecher et al., 1995). Finally, techniques to generate molecules with improved drug-like properties have recently emerged (Pierce et al., 2004). This work compounds these methodologies for the development of drug-like molecules to engineered receptors using computational and directed evolution methods.

In drug development, the refinement of ligand binding through target modification is impossible because targets cannot be altered. In the present case, however, both the ligand and receptor are amenable to engineering. Protein design tools have benefited from better, more robust force fields and scoring methods (Barnoud and Monticelli, 2015; Vanommeslaeghe and MacKerell, 2015). In conjunction with quantum mechanical geometry optimizations (Cho et al., 2005; Fu et al., 2011) and molecular dynamics simulations, protein-by-design strategies are widely displaying their effectiveness. Methodologies laid out below melds protein and ligand design strategies together to create a system to engineer truly orthogonal receptors and tailor-made small molecules.

Structure-Based Design Approach

An iterative process of computational design was employed to design orthogonal P2X receptor-ligand pairs. Using crystal structures of the zebrafish P2X4 in both bound-open and unbound-closed states and homology models of the other receptor subtypes, a fragment-based design approach (Guarnieri, 2015; Ludington, 2015) was utilized to design receptors and corresponding ATP-analogs using a suite of computational tools described below. While the ATP binding motif of P2X family receptors is not otherwise found in nature (FIG. 47), the U-shaped binding orientation is only crudely observed in Type II amino-acyl tRNA synthetases (Hattori and Gouaux, 2012). Additionally, several agonists/antagonists have been identified for each of the receptor subtypes (P2X1-7) (Dal Ben et al., 2015; North, 2002). Together these facts offered a unique opportunity for engineering custom receptors to ATP-analogs and the potential to design novel drug-like molecules to engineered receptors.

Computational Design of Receptors

Using the Molecular Operating Environment (MOE09.2014) suite of protein design and medicinal chemistry tools, NAMD Scalable Molecular Dynamics (Phillips et al., 2005), and resources at the Texas Advanced Computing Center, amino acid substitutions were computationally derived that enhance binding to one of a number of ATP-analogs (FIG. 48). 20 P2X4 receptor variants were designed to bind to 2-Chloro-ATP (2-Cl-ATP), 20 receptors that bind to 2'3'-O-(4-benzoyl-benzoyl)-adenosine 5'-triphosphate (BzATP), and an additional 20 receptors that bind adenylyl-imidodiphosphate (AmpPNP), a non-hydrolysable analog. The sets of designs independently focused on the three structural motifs bound by the receptor (base, sugar and phosphate) in an effort to minimize computational load and potentially allow design modularity. In silico selections were scored on binding energy, stability of the mutations in relation to the protein, and the overall potential energy of the agonist bound in the open state using an all atom force field with reaction field treatment of electrostatics. Candidate receptors were refined by rotamer exploration (Lovell et al., 2000), low-mode molecular dynamics (Labute, 2010b), and nanosecond timescale full molecular dynamics simulations in a 6 Å explicit solvent cage. Representative data for an in silica selection against 2-Cl-ATP (FIGS. 49A and B).

In Silico Screening of ATP-Analogs and in Cleft Design of Drug-Like Molecules

Homology models of each of the human and zebrafish P2X receptor subtypes were used in template-based docking studies to ensure the orthogonality of receptor-ligand pairs. To this end, a database of ATP-analogs was compiled that can be used to virtually screen candidate molecules for binding using a template-forced screening methodology, which restricts conformational rearrangements of docked ligands to those more closely matching empirically derived structures. Binding energies of these analogs were calculated for each of the receptor subtypes. Common motifs that resulted in productive binding found across multiple receptor types are eliminated from the design process. Unique compounds or rare functional groups can be identified using this process, and the ability to create tailored molecules to abolish binding to wild-type (unaltered) receptors by disrupting hydrogen bonding networks and introducing additional, sterically unfavorable transformations in the cleft can be used. Once candidate receptor-ligand pairs have been identified and validated, the scaffold of the ATP-analog can be replaced with components that are more drug-like in nature (Maass et al., 2007; Stewart et al., 2006). Further refinement of receptor design at this stage should create the first orthogonal P2X receptors and provide molecules that are usable in vivo (FIG. 51).

Directed Evolution of Orthogonal Receptor-Ligand Pairs

Selection Scheme Overview

The directed evolution approach to engineer receptor-ligand pairs builds on Compartmentalized Partnered Replication (CPR). In this selection scheme, the function of a genetic circuit drives the production of a DNA polymerase during an in vivo stage. After the initial expression of the circuit, individual cells are compartmentalized in emulsions and thermal cycled in the presence of nucleotides and primers specific to the component of interest. Libraries of individual components of the circuit are easily made by site saturation or error-prone PCR; variants that produce the most DNA polymerase will subsequently be more efficiently amplified (FIG. 52). Following multiple rounds of selection, the most active variants predominate, and can be further analyzed by sequencing and assay. The power of CPR as a selection tool derives from the decoupling of host fitness from circuit function and its ability to screen >$10_8$ variants in a single day. The production of thermostable polymerase in vivo is short-lived, negating fitness effects that hamper other selection methodologies, and the PCR amplification of functional genes allows for the ability to quickly and efficiently turn multiple rounds of selection. To date, CPR has been used to engineer: tRNAs, amino-acyl tRNA synthetases, orthogonal T7 RNA polymerase variants (Ellefson et al., 2014), transcription factors, and components of biosynthetic pathways (in preparation).

Positive Selection Design & Construction

Positive circuits were engineered in *S. cerevisiae* to generate DNA polymerase upon binding designed agonists from a semi-synthetic promoter, consisting of 4 tandem repeats of a 24-bp calcium-dependent response element (CDRE), a small fragment of the FKS2 promoter, joined to a truncated version of the Cyc1 promoter (Stathopoulos and Cyert, 1997). In the presence of agonist, polymerase is made in response to receptor function, which will in turn allow emulsion-based amplification of functional receptor variants (FIG. 51). Functional testing of the CDRE using a fluorescent reporter showed calcium dependent activation (FIG. 52).

Negative Selection Design & Construction

To select against constitutively active receptors, activation by ATP, the native ligand, or other off-target molecules, a counterselection circuit was used where channel opening in the absence of the target molecule results in death of the cell. A URA3-deficient strain of yeast was designed and replaced the polymerase in the construct outlined above with a functional URA3 under the control of a slightly weaker 2×CDRE synthetic promoter. Cells are then incubated in rich media with the addition of 5-Fluoroorotic acid (5-FOA). Off-target or constitutively active receptors will drive the expression of URA3, which converts 5-FOA to 5-Fluorouracil (5-FU), a highly toxic compound (FIG. 53). Modulation between rounds of positive selection (CPR) and a life/death negative selection allow for the selection of highly specific receptor variants to target molecules.

Functional Expression and Testing of P2X Subtypes in *S. cerevisiae* wt-hP2X4 receptors were expressed under the control of TDH3 and Gal promoters in wildtype *S. cerevisiae* (BY4741) and a ΔCne1p mutant, which has been shown to mitigate endoplasmic reticulum-mediated degradation of heterologously expressed transmembrane proteins (Prinz et al., 2003). By fusing Citrine, a fluorescent reporter, to the carboxy terminus of the receptor, a modest increase in expression was observed using the ΔCne1p mutant (FIG. 54). However, microscopy revealed large differences in localization patterns between the two strains. As predicted, the wild-type BY4741 cells were unable to traffic the receptor out of the ER, presumably explaining the modest decrease in signal during expression testing.

The results indicated that the receptor escaped the ER in the ΔCne1p mutant; however, the receptor was largely trapped within vacuoles or pits, leaving very few, if any, at the plasma membrane—likely due to tyrosine-mediated endocytosis. At this point the carboxy terminus of hP2X4 harbors a well-characterized non-canonical endocytic motif (YXXGO) (Royle et al., 2002), which is recognized by specific machinery in mammalian systems. Somewhat unsurprisingly, the clatherin-associated receptor recycling system is conserved in yeast (Chapa-y-Lazo et al., 2014; Weinberg and Drubin, 2012). These facts led to the truncation of the C-terminus of the receptor by 11 and 14 residues (ΔC11, ΔC14), which has been shown to increase plasma membrane localization in certain mammalian cell types without substantial effects on gating (Royle et al., 2005). Confocal microscopy revealed hP2X4ΔC14 was more efficiently trafficked and largely absent in the vacuoles compared to the wildtype receptor (FIG. 55).

To determine whether or not this truncated channel gated in yeast, an aequorin-based functional assay was used. Here aequorin, a bioluminescent protein, emits a photon upon binding calcium. This is done with the aid of coelenterazine, which must be added exogenously to yeast. The reaction is not catalytic, and the off-rate of calcium is too slow to observe on the timescales utilized in our assays. To optimize conditions for expression of both the receptor and reporter, a combination of integration, low-copy, and high-copy vectors was used. At this point, it was only possible to produce a signal upon addition of ATP, the native ligand, when both the receptor and reporter were expressed on high-copy plasmids (FIG. 56).

While encouraging, the amount of activation was small and unlikely to trigger the CDRE. Visual inspection of the primary sequence revealed that the truncated receptor now contained canonical C-terminal KKXX (SEQ ID NO: 1) ER retention signals (Gaynor et al., 1994). In an effort to increase the amount of receptor at the plasma membrane, we engineered a version with the ER export signal from Kir2.1 (FCYENEV, SEQ ID NO: 2) (Stockklausner et al., 2001). Confocal microscopy verified that the receptor largely escaped intracellular aggregation. Functional testing of this variant expressed from a single-copy integration vector revealed almost a full order of magnitude increase in signal when compared to the truncated version of the receptor (FIG. 57).

Next, all 7 P2X subtypes were built and integrated into the genome of BY4741ΔCne1p under the control of the GAL1 promoter. After verification of the integrations, these strains were transformed with high-copy plasmids expressing aequorin. Interestingly, many of the receptors were shown to be functional in assays when expressed from single-copy integration vectors (FIG. 57).

Surprisingly, the ligand-dependent signal generated by P2X2 was several orders of magnitude higher than any of the other subtypes. This is more than likely due to efficient trafficking and a lack of desensitization of the receptor to ATP. Of the 7 subtypes, P2X2 is considered to be 'non-desensitizing' and displays the highest single-channel conductance of the P2X receptor family (North, 2002). Due to the superior signal observed in our aequorin assay, a full kinetic analysis was performed to determine if the receptor expressed in yeast matched data from mammalian hosts. In an ATP dose-response assay, the $EC_{50}$ was calculated to be 6.7±1.5 µM—perfectly matching reported values (FIG. 58) (Lynch et al., 1999). Next, the P2X2 dose-response to 2-Cl-ATP (FIG. 59) and BzATP (FIG. 60) was characterized and it was found that the receptor was agonized by these compounds with nearly identical $EC_{50}$ values (26.7±3.6 and 29.1±6.0 µM, respectively) and in good agreement with published reports (Coddou et al., 2011; Jarvis and Khakh, 2009). Of particular interest, BzATP has been previously shown to lower the magnitude of response while increasing the time the channel is open (less desensitizing). The plate-based aequorin assay recapitulated this phenomenon. The amplitude of the BzATP generated signal is 3 orders of magnitude lower than either ATP or 2-Cl-ATP, and the duration that the channel remains open is almost 10-fold longer in the assays. AMP-PNP, a non-hydrolyzable ATP analog, did not gate P2X2. This negative result was expected because AMP-PNP has not been reported to activate P2X2. Suramin is a known P2X2 antagonist. To determine if our assay could detect inhibition, yeast cells were equilibrated expressing P2X2 with varying concentration of suramin. It was found that suramin inhibited P2X2 with an $IC_{50}$ of 31.6±1.4 µM (FIG. 61), well within the range of reported values (2-48 µM) (Baqi et al., 2011; Lambrecht et al., 2002). Finally, a non-functional double-mutant (K8 IC, K83C) (Roberts et al., 2008) was shown to be completely non-functional in the assay (FIG. 62), giving confidence that the results were robust and adequately accounted for known P2X2 properties.

This plate-based aequorin assay can be used in high-throughput drug discovery platforms. P2X2 can be used to build chimeric receptors with the N- or C-termini of P2X2 affixed to the extracellular and transmembrane portions of the other receptor subtypes. Doing so can allow more robust signal generation of the other receptors. It can also be useful to construct known 'desensitizing' mutations of the other receptors and test their activity using our yeast-based assay.

P2X2 Selections

Having built and proofed the individual components of the selection scheme, libraries of P2X2 are now under construction. To initially change the ligand specificity of P2X2 receptors, positions in the ATP binding pocket were saturated and selected for gating to AMP-PNP. Those circuits that can respond most readily to AMP-PNP can be readily identified within a few cycles of emulsion and amplification in the presence of primers specific for the P2X2 receptor. Another avenue to proof the selection methodology outlined above is to evolve the 'broken' double mutant back to wildtype function using ATP or 2-Cl-ATP.

CONCLUSIONS

Disclosed herein is a methodology to engineer robust, orthogonal receptor:ligand pairs. By combining rational design and directed evolution approaches, it is possible to engineer both the receptor and ligand. The ability to make complementary modifications in channel and ligand structure can help generate a family of orthogonal receptor-ligand pairs for independent control over multiple cell populations within the brain while eliminating crosstalk with endogenous factors. The strength of this and other pharmacogenetic approaches is that the locations of target neurons need not be known a priori; however, should precise temporal regulation be needed, the ligands could be chemically disabled, enabling brief localized photoactivation. A synthetic purinergic activator (SPArk) can advance functional brain mapping, provide robust control over discrete neuronal populations that represent known neurochemical classes or are selected using pioneering activity-based molecular-genetic methods.

Methods & Materials
Molecular Modeling of P2X Receptors

Homology models of human P2X subtypes were constructed using two reference structures (PDB: 4DW1 and 3H9V). The templates were prepared using the Molecular Operating Environment (MOE.09.2015) software package from Chemical Computing Group. The structure was inspected for anomalies and protonated/charged with the Protonate3D subroutine (310K, pH 7.4, 0.1 M salt). The protonated structure was then lightly tethered to reduce significant deviation from the empirically determined coordinates and minimized using the Amber10:EHT forcefield with R-field treatment of electrostatics to an RMS gradient of 0.1 kcal $mol_{-1}$ $Å_{-1}$. Homology models of the other P2X subtypes were prepared by creating 25 main chain models with 25 sidechain samples at 298K (625 total) within MOE. Intermediates were refined to an RMS gradient of 1 kcal $mol_{-1}$ $Å_{-1}$, scored with the GB/VI methodology, minimized again to an RMS gradient of 0.5 kcal $mol_{-1}$ $Å_{-1}$, and protonated. The final model for each variant was further refined by placing the protein within a 6 Å water sphere and minimizing the solvent enclosed structure to an RMS gradient of 0.001 kcal $mol_{-1}$ $Å_{-1}$. Models were evaluated by calculating Phi-Psi angles and superimposed against the reference structure. Agonist structures were created in cleft, and LigandInteractions subroutine was used to calculate binding energies. ResidueScan was used to identify potential amino acid substitutions for a given analog. Interactions were scored based on stability, affinity, and potential energy of the system.

Cloning and Expression of P2X Subtypes in Yeast

Sequences for the wild-type receptors and aequorin were obtained from Uniprot. Amino acid sequences were codon optimized for expression in *S. cerevisiae* and purchased as GeneBlocks from IDT. The Yeast Toolkit was then used for the Golden Gate Assembly of all vectors. Aequorin was expressed under the control of the pPGK2 promoter. P2X variants were expressed under the control of the GAL1 promoter. Fluorescently-tagged (Venus) constructs of receptor variants were also constructed for confocal microscopy and flow cytometry analyses.

Confocal Microscopy

Overnight cultures harboring fluorescently tagged (Venus) receptors were diluted 1:20 in fresh media. After 6 hours of growth, cells were washed 3 times with PBS. A total of 3 mL of cells were concentrated into 100 µL. 5 µL of the concentrated cells were placed on a slide. A coverslip was added and sealed with clear nail polish.

Aequorin Assays

BY4741ΔCne1p cells were transformed with vectors containing P2X variants. Transformants were validated and made competent for a subsequent transformation with a vector containing aequorin under the expression of the constitutive PGK2 promoter. Overnight cells were induced with 2% galactosidase for 20 hours. Following receptor expression, cells were collected by centrifugation and concentrated to 500 µL. The concentrated cells were then incubated with 5 µL of 1 mg/mL coelenterazine for 30 minutes at room temperature. Washed cells were then resuspended in softening buffer (1 M Sorbitol, 25 mM EDTA, 50 mM DTT), followed by washes in 1 M sorbitol and water. Cells were then resuspended in 50 mM MES/Tris pH 6.5 and aliquoted into a 96-well plate. Using an F500, 25 µL of cells were monitored for luminescence for 5 seconds. Upon addition of ligand or buffer (100 µL), cells were monitored for luminescence for varying times. Cell lysis was performed with the addition of 100 µL Tween20. For inhibition, varying concentrations of suramin were incubated with cells. Luminescence was monitored before and after the addition of 100 µL of 10 µM ATP. Areas under the curve were calculated and plotted against a negative control to determine the IC50.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

TABLE 1

Emulsion Parameters

| Parameter | Original (*E. coli*) | Optimal Yeast |
|---|---|---|
| Surfactant | 84 uL Abil | 84 uL Gransurf |
| Frequency of Tissuelyzer (Hz) | 42 | 37 |
| Time (min) | 4 | 5 |
| Cells (uL) | 300 | 500 |
| Mineral oil:Tegosoft (uL) | 240:876 | 240:876 |

TABLE 2

Yeast CPR/CSR Master Mix

| Component | Volume (μL) |
|---|---|
| 10X Buffer (pH 8.0) | 50 |
| 4 mM Stock dNTPs | 37.5 |
| F Primer (20 μM) | 20 |
| R Primer (20 μM) | 20 |
| TMAC | 5 |
| Zymolyase (5 mg/mL) | 80 |
| RNAse | 1.75 |
| diH$_2$0 | 285.75 |

TABLE 3

G-alpha Subunits

| Name | Strain Code | Terminal AA |
|---|---|---|
| Gpa1p | 00 | KIGII |
| Gαq | 01 | EYNLV |
| Gαs | 02 | QYELL |
| Gαo | 03 | GCGLY |
| Gαi2 | 04 | DCGLF |
| Gαi3 | 05 | ECGLY |
| Gαz | 06 | YIGLC |
| Gα12 | 07 | DIMLQ |
| Gα13 | 08 | QLMLQ |
| Gα14 | 09 | EFNLV |
| Gα16 | 10 | EINLL |

TABLE 4

SEQ ID NOS: 3-20 represent sgRNA oligos used for genomic knockouts

| Oligo | Sequence |
|---|---|
| EG.sgRNA.Far1.A.F | GACTTTACCAAGTTTGAAGAAAACAG |
| EG.sgRNA.Far1.A.R | AAACCTGTTTTCTTCAAACTTGGTAA |
| EG.sgRNA.Far1.B.F | GACTTTCCACCGAAGAAATTTCTAAG |
| EG.sgRNA.Far1.B.R | AAACCTTAGAAATTTCTTCGGTGGAA |
| EG.sgRNA.Far1.C.F | GACTTTATAGGCTTGGAAAGATTCAG |
| EG.sgRNA.Far1.C.R | AAACCTGAATCTTTCCAAGCCTATAA |
| EG.sgRNA.SSt2.A.F | GACTTTCAGTTCATCAGTAGAGGTGA |
| EG.sgRNA.Sst2.A.R | AAACTCACCTCTACTGATGAACTGAA |
| EG.sgRNA.Sst2.B.F | GACTTTTCAGGAAGCTATTAAAGCAA |
| EG.sgRNA.Sst2.B.R | AAACTTGCTTTAATAGCTTCCTGAAA |
| EG.sgRNA.Sst2.C.F | GACTTTACATAAATAATGTAAGAAGG |
| EG.sgRNA.Sst2.C.R | AAACCCTTCTTACATTATTTATGTAA |
| EG.sgRNA.Ste2.A.F | GACTTTACATAAATAATGTAAGAAGG |
| EG.sgRNA.Ste2.A.R | AAACCCTTCTTACATTATTTATGTAA |
| EG.sgRNA.Ste2.B.F | GACTTTTCAGTGACTTACGCTCTCAC |
| EG.sgRNA.Ste2.B.R | AAACGTGAGAGCGTAAGTCACTGAAA |
| EG.sgRNA.Ste2.C.F | GACTTTTTGCAACTCATCGAAAGTGA |
| EG.sgRNA.Ste2.C.R | AAACTCACTTTCGATGAGTTGCAAAA |

TABLE 5 sgRNA knockout efficiency

| Gene | Guide | KO | % effective sgRNA per gene | total % effective sgRNA |
|---|---|---|---|---|
| Ste2 | A | n | 67% | 67% |
| Ste2 | B | KO | | |
| Ste2 | C | KO | | |
| Sst2 | A | n | 33% | |
| Sst2 | B | n | | |
| Sst2 | C | KO | | |
| Far1 | A | KO | 100% | |
| Far1 | B | KO | | |
| Far1 | C | KO | | |

TABLE 6

Constructed GPCR Strains

| CODE | Parental | Resistance/Aux | Alterations |
|---|---|---|---|
| JG00-0.0 | BY4743ΔGal2 | G418 | ΔFar1-KO, ΔSte2-KO, ΔSSt2-KO |
| AM00-0.0 | BY4741 | None | ΔFar1-KO, ΔSte2-KO, ΔSSt2-KO |
| JG00-1.0 | JG00-0.0 | G418 | ΔpFig1-KOD |
| JG00-0.1 | JG00-0.0 | G418 | ΔpFus1-KOD |
| JG00-2.0 | JG00-0.0 | G418 | ΔpFig1-zsGreen1 |
| JG00-0.2 | JG00-0.0 | G418 | ΔpFus1-zsGreen1 |
| JG00-3.0 | JG00-0.0 | G418 | ΔpFig1-tetR |
| JG01-0.0 | JG00-0.0 | G418 | ΔGpa1-hGαq |
| JG01-1.0 | JG01-0.0 | G418 | ΔpFig1-KOD |

TABLE 6-continued

Constructed GPCR Strains

| CODE | Parental | Resistance/Aux | Alterations |
|---|---|---|---|
| JG01-2.0 | JG01-0.0 | G418 | ΔpFig1-zsGreen1 |
| JG01-3.0 | JG01-0.0 | G418 | ΔpFig1-tetR |
| JG02-0.0 | JG00-0.0 | G418 | ΔGpa1-hGαs |
| JG02-1.0 | JG02-0.0 | G418 | ΔpFig1-KOD |
| JG02-2.0 | JG02-0.0 | G418 | ΔpFig1-zsGreen1 |
| JG02-3.0 | JG02-0.0 | G418 | ΔpFig1-tetR |
| JG03-0.0 | JG00-0.0 | G418 | ΔGpa1-hGαi2 |
| JG03-1.0 | JG03-0.0 | G418 | ΔpFig1-KOD |
| JG03-2.0 | JG03-0.0 | G418 | ΔpFig1-zsGreen1 |
| JG03-3.0 | JG03-0.0 | G418 | ΔpFig1-tetR |
| JG04-0.0 | JG00-0.0 | G418 | ΔGpa1-hGαo |
| JG04-1.0 | JG04-0.0 | G418 | ΔpFig1-KOD |
| JG04-2.0 | JG04-0.0 | G418 | ΔpFig1-zsGreen1 |
| JG04-3.0 | JG04-0.0 | G418 | ΔpFig1-tetR |
| JG05-0.0 | JG00-0.0 | G418 | ΔGpa1-hGαi3 |
| JG05-1.0 | JG05-0.0 | 0418 | ΔpFig1-KOD |
| JG05-0.1 | JG05-0.0 | G418 | ΔpFus1-KOD |
| J005-2.0 | JG05-0.0 | G418 | ΔpFig1-zsGreen1 |
| JG05-0.2 | JG05-0.0 | G418 | ΔpFus1-zsGreen1 |
| JG05-2.2 | JG05-2.0 | G418 | ΔpFig1-zsGreen1, ΔpFus1-zsGreen1 |
| JG05-3.0 | JG05-2.0 | G418 | ΔpFig1-tetR |
| JG06-0.0 | JG00-0.0 | G418 | ΔGpa1-hGαz |
| JG06-1.0 | JG06-0.0 | G418 | ΔpFig1-KOD |

TABLE 7

Kinetics of CBD Enzymes

| EC # | Enzyme | Constitutive | kcat | Km | kcat/Km | Substrate |
|---|---|---|---|---|---|---|
| | CsAAE1 [O-succinylbenzoate-CoA ligase) Hexanoyl CoA Synthase TKS/OLS | pTDH3 | 2.0s-1 | 3.7 + 0.7 mM | 540.5s-1M1 1013s-1M-1 | Hexanoic acid +CoA |
| 2.3.1.206 | 3,5,7-trioxododecanoyl-CoA synthase (OLS) | pCCW12 | 2.96 (min-1) | .0608 (mM) | 811s-1M-1 | Hexanoyl-CoA |
| | | | 1.06 (min-1) | .0631 (mM) | 280s-1M-1 | Hexanoyl-CoA |
| | | | 3.46 (min-1) | .0569 (mM) | 1013s-1M-1 | 3,5,7-trioxodo-decanoyl-CoA |
| 4.4.1.26 | olivetolic acid cyclase (TKS) | pPGK1 | None available | None available | None available | Olicetolic acid* |
| 2.5.1.102 | CsPTI (Aromatic prenyl-transferase) geranyl-pyrophosphate-olivetolic acid gernyltransferase | pHHF2 | None available | 2 mM | None available | Mg2 ++ |
| 1.21.3.8 | cannabidiolic acid synthase (CBDA synthase) | pTEF11 | 0.19 (s-1) | .137 (mM) | 1386s-1M-1 | Cannabigerolic acid |
| 1.21.3.7 | Tetrahydrocannabinolic acid synthase (THCA synthase) WT | | .201 (s-1) | .134 (mM) | 556s-1M-1 | Cannabigerolic acid |

REFERENCES

1. Coward P, Wada H G, Falk M S, Chan S D, Meng F, Akil H, Conklin B R. Controlling signaling with a specifically designed Gi-coupled receptor. Proc Natl Acad Sci USA. 1998; 95(1):352-7. PubMed PMID: 9419379; PMCID: PMC18222.
2. Alexander G M, Rogan S C, Abbas A I, Armbruster B N, Pei Y, Allen J A, Nonneman R J, Hartmann J, Moy S S, Nicolelis M A, McNamara J O, Roth B L. Remote control of neuronal activity in transgenic mice expressing evolved G protein-coupled receptors. Neuron. 2009; 63(1):27-39. doi: 10.1016/j.neuron.2009.06.014. PubMed PMID: 19607790; PMCID: PMC2751885.
3. Armbruster B N, Li X, Pausch M H, Herlitze S, Roth B L. Evolving the lock to fit the key to create a family of G protein-coupled receptors potently activated by an inert ligand. Proc Natl Acad Sci USA. 2007; 104(12):5163-8. doi: 10.1073/pnas.0700293104. PubMed PMID: 17360345; PMCID: PMC1829280.
4. Guettier J M, Gautam D, Scarselli M, Ruiz de Azua I, Li J H, Rosemond E, Ma X, Gonzalez F J, Armbruster B N, Lu H, Roth B L, Wess J. A chemical-genetic approach to study G protein regulation of beta cell function in vivo. Proc Natl Acad Sci USA. 2009; 106(45):19197-202. doi: 10.1073/pnas.0906593106. PubMed PMID: 19858481; PMCID: PMC2767362.
5. Nakajima K, Wess J. Design and functional characterization of a novel, arrestin-biased designer G protein-coupled receptor. Mol Pharmacol. 2012; 82(4):575-82. doi: 10.1124/mol.112.080358. PubMed PMID: 22821234; PMCID: PMC3463219.
6. Vardy E, Robinson J E, Li C, Olsen R H, DiBerto J F, Giguere P M, Sassano F M, Huang X P, Zhu H, Urban D J, White K L, Rittiner J E, Crowley N A, Pleil K E, Mazzone C M, Mosier P D, Song J, Kash T L, Malanga C J, Krashes M J, Roth B L. A New DREADD Facilitates the Multiplexed Chemogenetic Interrogation of Behavior. Neuron. 2015; 86(4):936-46. doi: 10.1016/j.neuron.2015.03.065. PubMed PMID: 25937170; PMCID: PMC4441592.
7. Ellefson J W, Meyer A J, Hughes R A, Cannon J R, Brodbelt J S, Ellington A D. Directed evolution of genetic parts and circuits by compartmentalized partnered replication. Nature biotechnology. 2014; 32(1):97-101. doi: 10.1038/nbt.2714. PubMed PMID: 24185096.
8. Meyer A J, Ellefson J W, Ellington A D. Directed Evolution of a Panel of Orthogonal T7 RNA Polymerase Variants for in Vivo or in Vitro Synthetic Circuitry. ACS synthetic biology. 2015; 4(10):1070-6. doi: 10.1021/sb500299c. PubMed PMID: 25279711.
9. Iwamura H, Suzuki H, Ueda Y, Kaya T, Inaba T. In vitro and in vivo pharmacological characterization of JTE-907, a novel selective ligand for cannabinoid CB2 receptor. J Pharmacol Exp Ther. 2001; 296(2):420-5. PubMed PMID: 11160626.
10. Ibrahim M M, Porreca F, Lai J, Albrecht P J, Rice F L, Khodorova A, Davar G, Makriyannis A, Vanderah T W, Mata H P, Malan T P, Jr. CB2 cannabinoid receptor activation produces antinociception by stimulating peripheral release of endogenous opioids. Proc Natl Acad Sci USA. 2005; 102(8):3093-8. doi: 10.1073/pnas.0409888102. PubMed PMID: 15705714; PMCID: PMC549497.
11. Dong S, Rogan S C, Roth B L. Directed molecular evolution of DREADDs: a generic approach to creating next-generation RASSLs. Nat Protoc. 2010; 5(3):561-73. doi: 10.1038/nprot.2009.239. PubMed PMID: 20203671.
12. Hagen D C, McCaffrey G, Sprague G F, Jr. Pheromone response elements are necessary and sufficient for basal and pheromone-induced transcription of the FUS1 gene of *Saccharomyces cerevisiae*. Mol Cell Biol. 1991; 11(6): 2952-61. PubMed PMID: 1903837; PMCID: PMC360123.
13. Brown A J, Dyos S L, Whiteway M S, White J H, Watson M A, Marzioch M, Clare J J, Cousens D J, Paddon C, Plumpton C, Romanos M A, Dowell S J. Functional coupling of mammalian receptors to the yeast mating pathway using novel yeast/mammalian G protein alpha-subunit chimeras. Yeast. 2000; 16(1):11-22. doi: 10.1002/(SICI)1097-0061(20000115)16:1<11::AID-YEA502>3.0.CO;2-K. PubMed PMID: 10620771.
14. Lee M E, DeLoache W C, Cervantes B, Dueber J E. A Highly Characterized Yeast Toolkit for Modular, Multipart Assembly. ACS synthetic biology. 2015; 4(9):975-86. doi: 10.1021/sb500366v. PubMed PMID: 25871405.
15. Tanaka S, Miyazawa-Onami M, Iida T, Araki H. iAID: an improved auxin-inducible degron system for the construction of a 'tight' conditional mutant in the budding yeast *Saccharomyces cerevisiae*. Yeast. 2015; 32(8):567-81. doi: 10.1002/yea.3080. PubMed PMID: 26081484.
16. Gertsch J, Leonti M, Raduner S, Racz I, Chen J Z, Xie X Q, Altmann K H, Karsak M, Zimmer A. Beta-caryophyllene is a dietary cannabinoid. Proc Natl Acad Sci USA. 2008; 105(26):9099-104. doi: 10.1073/pnas.0803601105. PubMed PMID: 18574142; PMCID: PMC2449371.
17. Pertwee R G. The diverse CB1 and CB2 receptor pharmacology of three plant cannabinoids: delta9-tetrahydrocannbinol, cannabidiol and delta9-tetrahydrocannabivarin. Br J Pharmacol. 2008; 153(2):199-215. doi: 10.1038/sj.bjp.0707442. PubMed PMID: 17828291; PMCID: PMC2219532.

What is claimed is:

1. A method of determining an association of a signal transduction pathway or receptor and an effector molecule of the signal transduction pathway or receptor, the method comprising: a) providing a eukaryotic cell comprising a recombinant molecule encoding a naturally occurring or functional variant of a eukaryotic signal transduction pathway or receptor and a polymerase, and further providing an effector molecule, wherein when the effector molecule interacts with the signal transduction pathway or receptor, transcription of the signal transduction pathway or receptor and polymerase takes place; b) isolating the eukaryotic cell; c) exposing the recombinant molecule to primers capable of amplifying the signal transduction pathway or receptor and polymerase under conditions sufficient for amplification of the recombinant molecule; and d); detecting interaction between the signal transduction pathway or receptor and an effector molecule by detecting that amplification occurred.

2. The method of claim 1, wherein said eukaryotic cell is a yeast cell.

3. The method of claim 1, wherein said polymerase is thermostable polymerase.

4. The method of claim 1, wherein the polymerase is coupled with bar-coding.

5. The method of claim 1, wherein said receptor or signal transduction pathway is non-naturally occurring in the organism to which it is exposed.

6. The method of claim 5, wherein said receptor or signal transduction pathway is naturally occurring in the organism to which it is exposed, or a functional variant of a naturally occurring eukaryotic receptor or signal transduction pathway in the organism to which it is exposed.

7. The method of claim 6, wherein said receptor is an orthogonal receptor.

8. The method of claim 1, wherein said method is used for selection of an effector molecule produced by a metabolic pathway that activates the receptor or signal transduction pathway.

9. The method of claim 1, wherein said method is used for the co-identification of metabolic pathways and receptors that functionally interact.

10. The method of claim 1, wherein said organisms are emulsified prior to exposure to the recombinant molecule.

11. The method of claim 1, wherein the polymerase is a DNA or RNA polymerase.

12. The method of claim 11, wherein detecting interaction between the signal transduction pathway or receptor and an effector molecule comprises sequencing a component of the signal transduction pathway or receptor, or the effector molecule.

13. The method of claim 12, wherein said sequencing utilizes RNASeq.

14. The method of claim 1, wherein the effector molecule is an agonist or antagonist.

15. The method of claim 1, wherein the receptor is a P2X receptor.

16. The method of claim 1, wherein the recombinant molecule is a plasmid.

17. The method of claim 1, wherein the recombinant molecule is introduced to a cell.

18. The method of claim 1, wherein the isolated cell is trapped in oil-in-emulsion.

* * * * *

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

Lys Lys Xaa Xaa
1

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Phe Cys Tyr Glu Asn Glu Val
1               5

<210> SEQ ID NO 3
<211> LENGTH: 26
<212> TYPE: DNA
<213> ORGANISM: Saccharomyces cerevisiae

<400> SEQUENCE: 3
gactttacca agtttgaaga aaacag                                      26

<210> SEQ ID NO 4
<211> LENGTH: 26
<212> TYPE: DNA
<213> ORGANISM: Saccharomyces cerevisiae

<400> SEQUENCE: 4

```
aaacctgttt tcttcaaact tggtaa                                              26

<210> SEQ ID NO 5
<211> LENGTH: 26
<212> TYPE: DNA
<213> ORGANISM: Saccharomyces cerevisiae

<400> SEQUENCE: 5
gactttccac cgaagaaatt tctaag                                              26

<210> SEQ ID NO 6
<211> LENGTH: 26
<212> TYPE: DNA
<213> ORGANISM: Saccharomyces cerevisiae

<400> SEQUENCE: 6
aaaccttaga aatttcttcg gtggaa                                              26

<210> SEQ ID NO 7
<211> LENGTH: 26
<212> TYPE: DNA
<213> ORGANISM: Saccharomyces cerevisiae

<400> SEQUENCE: 7
gactttatag gcttggaaag attcag                                              26

<210> SEQ ID NO 8
<211> LENGTH: 26
<212> TYPE: DNA
<213> ORGANISM: Saccharomyces cerevisiae

<400> SEQUENCE: 8
aaacctgaat ctttccaagc ctataa                                              26

<210> SEQ ID NO 9
<211> LENGTH: 26
<212> TYPE: DNA
<213> ORGANISM: Saccharomyces cerevisiae

<400> SEQUENCE: 9
gactttcagt tcatcagtag aggtga                                              26

<210> SEQ ID NO 10
<211> LENGTH: 26
<212> TYPE: DNA
<213> ORGANISM: Saccharomyces cerevisiae

<400> SEQUENCE: 10
aaactcacct ctactgatga actgaa                                              26

<210> SEQ ID NO 11
<211> LENGTH: 26
<212> TYPE: DNA
<213> ORGANISM: Saccharomyces cerevisiae

<400> SEQUENCE: 11 gactttcag gaagctatta aagcaa                                               26

<210> SEQ ID NO 12
<211> LENGTH: 26
<212> TYPE: DNA
<213> ORGANISM: Saccharomyces cerevisiae

<400> SEQUENCE: 12
```

-continued aaacttgctt taatagcttc ctgaaa                                    26

<210> SEQ ID NO 13
<211> LENGTH: 26
<212> TYPE: DNA
<213> ORGANISM: Saccharomyces cerevisiae

<400> SEQUENCE: 13
gactttacat aaataatgta agaagg                                    26

<210> SEQ ID NO 14
<211> LENGTH: 26
<212> TYPE: DNA
<213> ORGANISM: Saccharomyces cerevisiae

<400> SEQUENCE: 14
aaacccttct tacattattt atgtaa                                    26

<210> SEQ ID NO 15
<211> LENGTH: 26
<212> TYPE: DNA
<213> ORGANISM: Saccharomyces cerevisiae

<400> SEQUENCE: 15
gactttacat aaataatgta agaagg                                    26

<210> SEQ ID NO 16
<211> LENGTH: 26
<212> TYPE: DNA
<213> ORGANISM: Saccharomyces cerevisiae

<400> SEQUENCE: 16
aaacccttct tacattattt atgtaa                                    26

<210> SEQ ID NO 17
<211> LENGTH: 26
<212> TYPE: DNA
<213> ORGANISM: Saccharomyces cerevisiae

<400> SEQUENCE: 17 gactttcag tgacttacgc tctcac                                     26

<210> SEQ ID NO 18
<211> LENGTH: 26
<212> TYPE: DNA
<213> ORGANISM: Saccharomyces cerevisiae

<400> SEQUENCE: 18
aaacgtgaga gcgtaagtca ctgaaa                                    26

<210> SEQ ID NO 19
<211> LENGTH: 26
<212> TYPE: DNA
<213> ORGANISM: Saccharomyces cerevisiae

<400> SEQUENCE: 19 gacttttgc aactcatcga aagtga                                     26

```
<210> SEQ ID NO 20
<211> LENGTH: 26
<212> TYPE: DNA
<213> ORGANISM: Saccharomyces cerevisiae

<400> SEQUENCE: 20
aaactcactt tcgatgagtt gcaaaa                                          26
```